United States Patent
Deng et al.

(10) Patent No.: US 10,660,828 B2
(45) Date of Patent: *May 26, 2020

(54) HYPERBRANCHED POLYGLYCEROL-COATED PARTICLES AND METHODS OF MAKING AND USING THEREOF

(71) Applicant: Yale University, New Haven, CT (US)

(72) Inventors: Yang Deng, Edison, NJ (US); Asiri Ediriwickrema, Cary, NC (US); William M. Saltzman, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,456

(22) Filed: Sep. 19, 2016

(65) Prior Publication Data

US 2017/0000737 A1   Jan. 5, 2017

Related U.S. Application Data

(63) Continuation-in-part of application No. PCT/US2015/030169, filed on May 11, 2015.

(60) Provisional application No. 61/991,025, filed on May 9, 2014.

(51) Int. Cl.

| | |
|---|---|
| *A61K 8/02* | (2006.01) |
| *C08G 83/00* | (2006.01) |
| *C07C 59/06* | (2006.01) |
| *C07C 59/08* | (2006.01) |
| *A61K 31/4178* | (2006.01) |
| *A61K 9/00* | (2006.01) |
| *A61K 9/50* | (2006.01) |
| *A61K 9/16* | (2006.01) |
| *A61K 31/427* | (2006.01) |
| *A61K 9/51* | (2006.01) |
| *A61K 31/4745* | (2006.01) |
| *A61K 47/34* | (2017.01) |
| *A61K 8/90* | (2006.01) |
| *A61Q 17/04* | (2006.01) |

(52) U.S. Cl.
CPC .............. *A61K 8/0241* (2013.01); *A61K 8/90* (2013.01); *A61K 9/0014* (2013.01); *A61K 9/0019* (2013.01); *A61K 9/0053* (2013.01); *A61K 9/1647* (2013.01); *A61K 9/5031* (2013.01); *A61K 9/5146* (2013.01); *A61K 9/5153* (2013.01); *A61K 31/4178* (2013.01); *A61K 31/427* (2013.01); *A61K 31/4745* (2013.01); *A61K 47/34* (2013.01); *A61Q 17/04* (2013.01); *C07C 59/06* (2013.01); *C07C 59/08* (2013.01); *C08G 83/005* (2013.01); *A61K 2800/412* (2013.01); *A61K 2800/413* (2013.01); *A61K 2800/624* (2013.01)

(58) Field of Classification Search
CPC .............. A61K 31/4178; A61K 31/427; A61K 9/1647; A61K 9/5031; A61K 8/0241; A61K 8/90; A61K 31/4745; A61K 9/0053; A61K 9/0019; A61K 47/34; A61K 9/5153; A61K 9/0014; A61K 9/5146; A61K 2800/624; A61K 2800/412; A61K 2800/413; A61Q 17/00; A61Q 17/04; C07C 59/06; C07C 59/08; C08G 83/005

See application file for complete search history.

(56) References Cited

U.S. PATENT DOCUMENTS

| | | | |
|---|---|---|---|
| 6,673,545 B2 | 1/2004 | Faris | |
| 6,677,157 B1 | 1/2004 | Cohen | |
| 6,699,475 B1 | 3/2004 | Panicali | |
| 8,206,747 B2 * | 6/2012 | Zale ........................ | A61K 9/10 424/489 |
| 8,715,736 B2 * | 5/2014 | Sachdeva ............. | A61K 31/192 424/400 |
| 9,492,382 B2 | 11/2016 | Türk | |
| 2005/0118252 A1 | 6/2005 | Bae | |
| 2006/0105026 A1 | 5/2006 | Fortune | |
| 2011/0060036 A1 | 3/2011 | Nie | |
| 2011/0200666 A1 | 8/2011 | Teichmueller | |
| 2012/0195957 A1 | 8/2012 | Sachdeva | |

FOREIGN PATENT DOCUMENTS

| | | |
|---|---|---|
| WO | 2000050900 | 8/2000 |
| WO | 2012151539 | 11/2012 |
| WO | 2013166487 | 11/2013 |
| WO | 2015172149 | 11/2015 |
| WO | 2015172153 | 11/2015 |
| WO | 2016183209 | 11/2016 |
| WO | 2016183217 | 11/2016 |

OTHER PUBLICATIONS

Biomateriais 34 (2013) 6058-6067 (Cholic acid-functionalized nanoparticles of star-shaped PLGA-vitamin E TPGS (Year: 2013).*

(Continued)

*Primary Examiner* — Snigdha Maewall
(74) *Attorney, Agent, or Firm* — Pabst Patent Group LLP

(57) ABSTRACT

Core-shell particles and methods of making and using thereof are described herein. The core is formed of or contains one or more hydrophobic materials or more hydrophobic materials. The shell is formed of or contains hyperbranched polyglycerol (HPG). The HPG coating can be modified to adjust the properties of the particles. Unmodified HPG coatings impart stealth properties to the particles which resist non-specific protein absorption and increase circulation in the blood. The hydroxyl groups on the HPG coating can be chemically modified to form functional groups that react with functional groups and adhere the particles to tissue, cells, or extracellular materials, such as proteins.

24 Claims, 17 Drawing Sheets

(56) References Cited

OTHER PUBLICATIONS

Materials 2010, 3, 1928-1980; doi:10.3390/ma3031928 (Year: 2010).*
Mugabe et al. (Paclitaxel incorporated in hydrophobically derivatized hyperbranched polyglycerols for intravesical bladder cancer therapy, BJUI International, 2008, vol. 103, pp. 978-986). (Year: 2008).*
An, et al., "ph-(low)-insertion-peptide (pHLIP) translocation of membrane impermeable phalloidin toxin inhibits cancer cell proliferation", PNAS, 107(47):20246-50 (2010).
Aoyagi, et al., "Current treatment options for colon cancer peritoneal carcinomatosis", World J Gastroenterol., 20(35):12493-12500 (2014).
Armstrong, et al., "A phase 1 trial of intraperitoneal sustained-release paclitaxel microspheres (Paclimer) in recurrent ovarian cancer: a Gynecologic Oncology Group study", Gynecologic Oncology, 103:391-6 (2006).
Bao, et al., "QX26 modified hyperbranched polylycerol-conjugated poly(lactic-co-glycolic acid) nanoparticles: synthesis characterization and evaluation of its brain delivery ability", J Mater Sci Mater Med., 23(8):1891-901 (2012).
Bobo, et al, "Convection-enhanced delivery of macromolecules in the brain", PNAS, 91:2076-80 (1994).
Bourges, et al., "Ocular drug delivery targeting the retina and retinal pigment epithelium using polylactide nanoparticles", Invest. Ophthalmol. Vis Sci., 44:3562-9(2003).
Colombo, et al., "Randomized, open-label, phase III study comparing patupilone (EPO906) with pegylated liposomal doxorubicin in platinum-refractory or -resistant patients with recurrent epithelial ovarian, primary fallopian tube, or primary peritoneal cancer", J Clinl Oncol., 30: 3841-7 (2012).
Daniele, et al., "Modulation of A1 and A2B adenosine receptor activity: a new strategy to sensitise glioblastoma stem cells to chemotherapy", Cell Death Dis., 5:e1539. doi: 10.1038/cddls.2014. 487 (2014).
De Bree, et al., "Intraperitoneal chemotherapy for prevention and treatment of peritoneal carcinomatosis from colorectal origin", Ann Gastroenterology, 16:20-33 (2003).
De Kozak, et al., "Intraocular injection of tamoxlfen-loaded nanopanicles: a new treatment of experimental autoimmune uveoretinitis", Eur. J. Immunol. 34(12):3702-12 (2004).
Deng, et al., "A sunblock based on bioadhesive nanoparticles", Nat Mater., 14(12):1278-85 (2015).
Deng, et al., "Improved i.p. drug delivery with bioadhesive nanoparticle", PNAS, 113(41): 11453-8 (2016).
Deng, et al., "The effect of hyperbranched polyglycerols coatings on drug delivery using degradable polymer nanoparticles", Btomaterials, 35:6595-6602 (2014).
Dong, et al., "Poly(glycoamidoamine) brushes formulated nanomaterials for systemic siRNA and mRNA delivery in vivo", Nano Lett, 16:842-8 (2016).
Engelman, "pHLIP, a novel technology to locate and treat tumors", Public release Yale University, http://www.eurrkalrrt.org/pub_release/2007-05/yu-pan050107, (2007).
Gao, et al., "Synthesis and physiohemical characterization of a novel amphiphilic polylactic acid-hyperbranched polyglycerol conjugate for protein delivery", J Cont Rel., 140:141-7 (2009).
Gaudin, et al., "Poly(Lec4cacid)" Hyperbranched Polyglycerol Nanopar4cles for Improved Drug Treatment of Gliomas by Convec4on—"Enhanced Delivery", Sno-Scidot Joint Conference on Therapeutic Delivery to the CNS, Marriot Rivercenter Hotel, San Antonio, TX Nov. 18-19, 2015.
Guzman, et al., "Local intraluminal infusion of biodegradable polymeric nanoparticles. A novel approach for prolonged drug delivery after balloon angioplasty", Circulation 94:1441-8 (1996).
International Search Report for PCT application PCT.US2005/030169 dated Aug. 4, 2015.
International Search Report for PCT application PCT/US2005/030187 dated Aug. 5, 2015.
International Search Report for PCT application PCT/US2016/031879 dated Jul. 22, 2016.
International Search Report for PCT application PCT/US2016/031890 dated Jul. 22, 2016.
Labhasetwar, et al., "Arterial uptake of biodegradable nanoparticles: effect of surface modifications", J Pharm Sci 87, 1229-34 (1998).
Lee, et al., "A1 adenosine receptor activation inhibits inflammation, necrosis, and apoptosis after renal ischemia-reperfusion injury in mice", J Am Soc Nephrol, 15:102-11 (2004).
Mainardes, et el., "Colloidal carriers for ophthalmic drug delivery", Curr. Drug Targets 6(3):363-71 (2005).
Saucier-Sawyer, et al., "Systemic delivery of blood-brain barrier-targeted polymeric nanoparticles enhances delivery to brain tissue", J Drug Target., 23(7-8):736-49 (2015).
Shu, et al., "Residue-specific structures and membrane locations of pH-low Insertion peptide by solid-state nuclear magnetic resonance", Nat Commun., 6:7787. doi: 10.1038/ncomms8787 (2015).
Song, et al., "Arterial uptake of biodegradable nanoparticles for intravascular local drug delivery: results with an acute dog model", J Control Release 54(2):201-11 (1998).
Steinbacher, et al., "Gd-labeled microparticles in MRI: in vivo imaging of microparticles after intraperitoneal injection", Small, 6(23):2678-82 (2010).
Synowitz, et al., "A1, adenosine receptors in microglia control glioblastoma-host interaction", Cancer Res., 66(17):8550-7 (2006).
Tsai, et al., "Effects of carrier on disposition and antitumor activity of intraperitoneal Paclitaxel", Pharmaceutical Research, 24, 1691-1701 (2007).
Yang, et al., "Intraperitoneal delivery of paclitaxel by poly(ether-anhydride) microspheres effectively suppresses tumor growth in a murine metastatic ovarian cancer model", Drug DelivTransllRe., 4, 203-209 (2014).
Andreev, et al., "pH-sensitive membrane peptides (pHILPs) as a novel class of delivery agents", Molecular Brain Biology, 2(7):341-352 (2010).
Solaro, et al., "Targeted delivery of protein drugs by nanocarriers", Materials, 3:1928-80 (2010).
Zeng, et al., "Cholic acid-functionalized nanoparticles of star-shaped PLGA-vitamin E TPCS copolymer for docetaxel delivery to cervical cancer", Biomaterials, 64:6058-67 (2013).

* cited by examiner

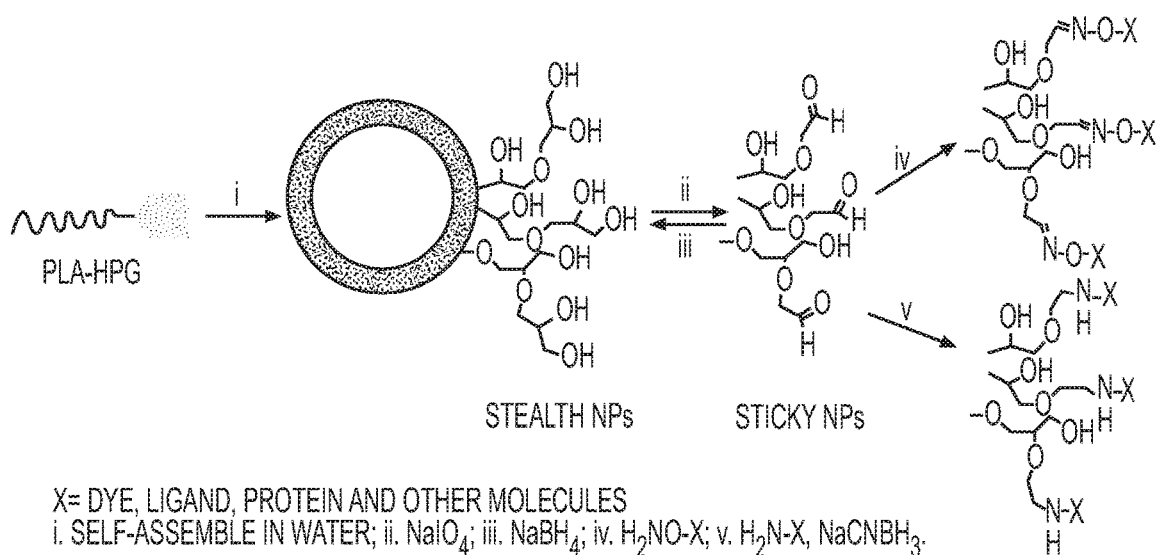
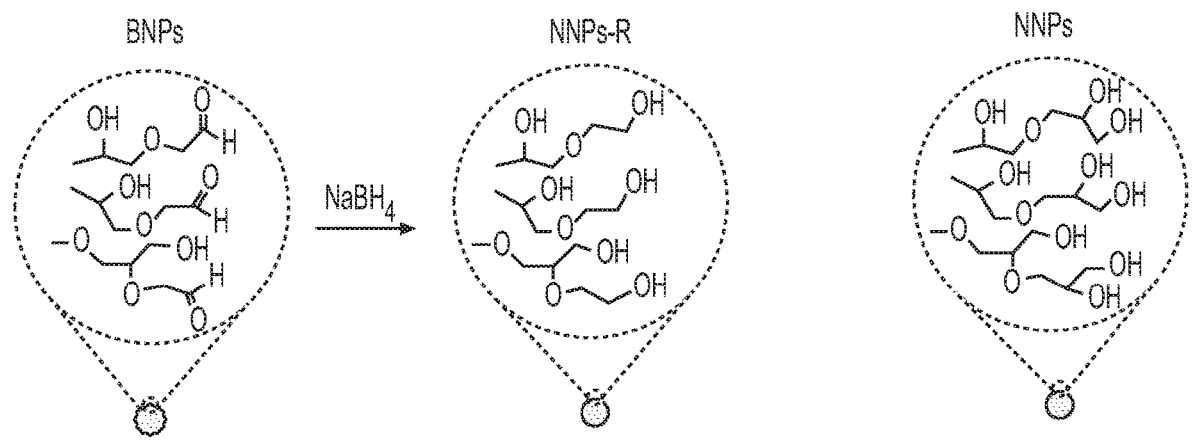
FIG. 1A
FIG. 1B
FIG. 1C

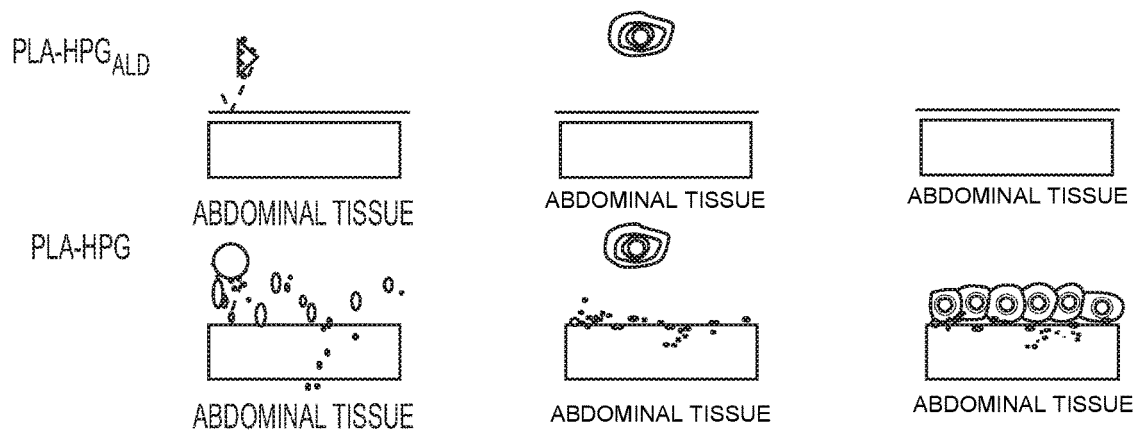
*FIG. 10A*  *FIG. 10B*  *FIG. 10C*
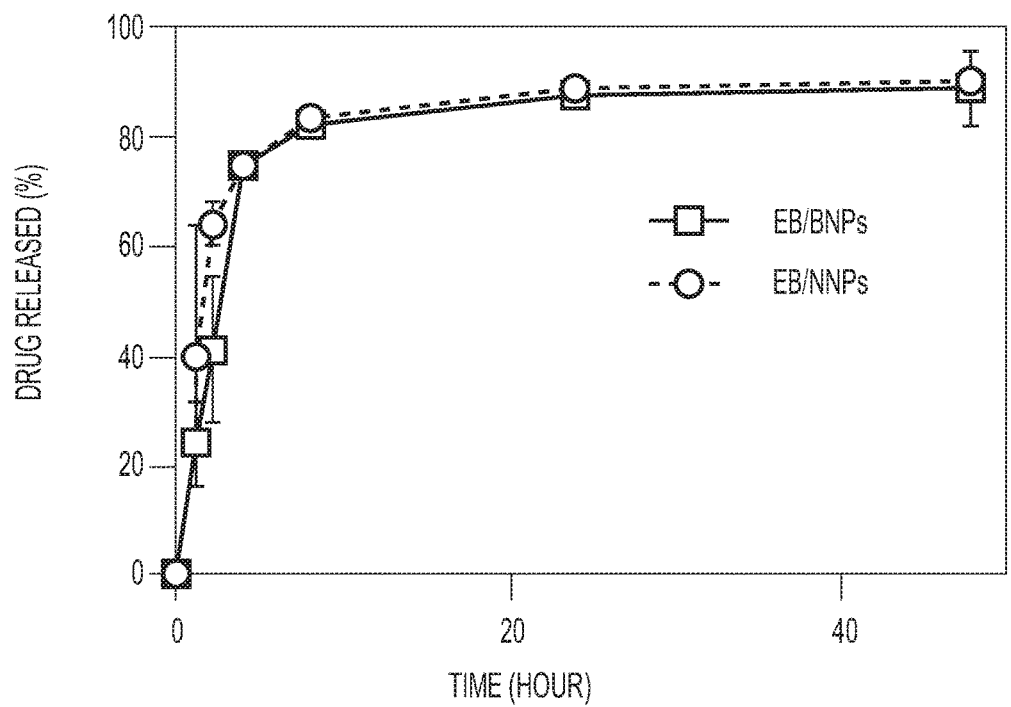
*FIG. 11A*

HYPERBRANCHED POLYGLYCEROL-COATED PARTICLES AND METHODS OF MAKING AND USING THEREOF

CROSS REFERENCE TO RELATED APPLICATIONS

This application is a continuation-in-part of International Application no. PCT/US2015/030169, filed on May 11, 2015, which claims priority to and benefit of U.S. Provisional Application No. 61/991,025 "Hyberbranched Polyglycerol-Coated Particles and Methods of Making and Using Thereof" filed on May 9, 2014, the disclosures of which are hereby incorporated herein by reference in their entirety.

STATEMENT REGARDING FEDERALLY SPONSORED RESEARCH

This invention was made with government support under Grant Nos. EB000487, CA149128, and CA154460 awarded by the National Institutes of Health. The government has certain rights in the invention.

FIELD OF THE INVENTION

This invention is in the field of particles, such as microparticles and/or nanoparticles, coated with hyperbranched polyglycerol, wherein the coating can be tuned to provide stealth or adhesive properties.

BACKGROUND OF THE INVENTION

Over the past decade, nanotechnology has been explored to improve bioavailability, lower side effects, and enhance targeting of therapeutic agents for a wide variety of diseases. When agents are administered systemically, the therapeutic effect is typically lowered by rapid clearance through enzymatic digestion, renal filtration, and mononuclear phagocytic system (MPS) uptake. Encapsulating the agent in nanoparticles (NPs) has been investigated to modulate these factors, as the precisely engineered NPs can protect the agent from rapid clearance but also help it reach the target site more efficiently and preferentially. Widely used materials for producing NPs include polymers, lipids and some inorganic materials. However, encapsulation of therapeutic agents in NPs does not ensure successful delivery. In fact, particulates are often more efficiently cleared from the blood by MPS uptake, particularly by phagocytic cells in the liver, leading to rapid loss of NPs and their associated drugs from circulation, which limits their ability to reach non-liver targets.

It is well-known that surface modification of NPs with substances that prevent non-specific adsorption can reduce their interaction with serum proteins and increase the blood circulation of the NPs. An ideal surface coating resists non-specific adsorption of proteins and facilitates the attachment of other functionalities, such as targeting ligands, to the particle. To resist non-specific adsorption in physiological conditions, materials for coating are usually charge neutral, hydrophilic, and stable in physiological environments. Among the few materials used as coating for NPs, PEG has become ubiquitous. The advantages of PEG as a coating of NPs for drug delivery include its low toxicity, low immunogenicity, and resistance to non-specific adsorption of biomolecules. PEG has so dominated the field of surface coatings that new approaches are rarely investigated.

However, PEG has considerable limitations. For instance, it is known that PEG chains can adopt a variety of configurations on the surface, depending on PEG surface density, and the most effective densities are often difficult to achieve.

There exists a need for particles with improved coatings, in which the coatings can be tuned to provide stealth or adhesive properties and can further be modified with targeting Moieties, and which overcome the limitations associated with polyethylene glycol coatings.

Therefore, it is an object of the invention to provide particles with coatings which can be made with stealth or adhesive properties.

It is a further object of the present invention to provide coatings that can be modified with targeting moieties.

It is a further object of the present invention to provide methods of making particles with the coatings.

It is another object of the present invention to provide methods of using particles with the coatings.

SUMMARY OF THE INVENTION

Core-shell particles, such as microparticles and nanoparticles, and methods of making and using, are formed of or contain a hydrophobic material or more hydrophobic material, such as a polymer. The shell is formed of or contains hyperbranched polyglycerol (HPG). The HPG can be covalently bound to the one or more materials that form the core such that, upon self-assembly, particles are formed in which the hydrophobic or more hydrophobic materials form the core and the HPG forms a coating on the particle.

The HPG coating can be modified to adjust the properties of the particles. For example, unmodified HPG coatings impart stealth properties to the particles which resist non-specific protein absorption and increase circulation in the blood. Alternatively, the hydroxyl groups on the HPG coating can be chemically modified to form functional groups that react with functional groups on tissue or otherwise interact with tissue to adhere the particles to the tissue, cells, or extracellular materials, such as proteins. Such functional groups include, but not limited to, aldehydes, amines, and O-substituted oximes.

Particles with an HPG coating chemically modified to form functional groups are referred to as bioadhesive nanoparticles (BNPs). Particles with chemically unmodified HPG coating are referred to as nonbioadhevise nanoparticles (NNPs). The chemically modified HPG coating of BNPs forms a bioadhesive corona surrounding the hydrophobic material forming the core.

The surface of the particles can further be modified with one or more targeting moieties or covalently bound to HPG via a coupling agent or spacer in organic solvents such as dichloromethane (DCM), dimethylformamide (DMF), dimethyl sulfoxide (DMSO) or tetrahydrofuran (THF). In some embodiments, the polymer is functionalized/modified before nanoparticle formation. Alternatively, the targeting moieties may be attached to NPs after the synthesis of NPs in aqueous solution or other protic solution such as alcohol. For example, HPG coated NPs can be transformed to aldehyde terminated NPs by $NaIO_4$ treatment (or carboxylic acid terminated by $NaIO_4$ treatment followed by sodium chlorite treatment) so the targeting moieties may be directly covalently attached to NPs via aldehyde (or carboxylic acid) groups on NPs and functional groups (amine, hydrazine, aminooxy and their derivatives) on the targeting moieties or indirectly attached to the NPs via coupling agents or spacers (such as aminooxy modified biotin and cysteine).

The particles can further contain one or more therapeutic agents, diagnostic agents, prophylactic agents, and/or nutraceuticals. The one or more agents can be covalently or non-covalently associated with the particles. The agents can be encapsulated within the particle, for example, dispersed within the core; non-covalently associated with the surface of the particles, covalently-associated with the surface of the particles, or combinations thereof.

The particles are useful in methods for delivery of therapeutic, nutraceutical, diagnostic and prophylactic agents.

HPG coatings can also be used to alter the surface properties of other moieties, such as delivery vehicles (liposomes, micelles, protein aggregates), metals and metal oxides, (thiolated gold conjugated to HPG). HPG can impart stealth properties to these materials. Alternatively, the vicinyl diol groups can be transformed to functional groups that promote adhesion of the vehicle to biological materials, such as tissue, cells, and/or proteins.

BRIEF DESCRIPTION OF THE DRAWINGS

FIG. 1A is a schematic showing the synthesis of stealth nanoparticles and sticky nanoparticles. FIG. 1B is a schematic showing modification of bioadhesive nanoparticles (BNPs) to reduced non-adhesive nanoparticles (NNP-Rs). FIG. 1C is a schematic of stealth nonadhesive nanoparticles (NNPs) for comparison with NNP-Rs. The conversion of BNPs to NNP-Rs is by $NaBH_4$ treatment. The surface structures of NNPs, BNPs, and NNP-Rs is shown.

FIG. 10A is a diagram of PLA-HPG$_{ALD}$ NPs adhered to the surface of abdominal tissues and PLA-HPG NPs diffused to all abdominal cavity and removed by lymphatic drainage. FIG. 10B is a diagram of metastasized tumor cells attached to the surface of abdominal tissues. FIG. 10C is a diagram showing tumor cell growth is suppressed by PLA-HPG$_{ALD}$/EB NPs on the abdominal tissues.

FIG. 11A is a graph of drug release in (%) from EB/PLA-HPG$_{ALD}$ NPs (EB/BNPs) and EB/PLA-HPG NPs (EB/NNPs) over time. Data are shown as mean±SD (n=4).

DETAILED DESCRIPTION OF THE INVENTION

I. Definitions

Figure 2A:
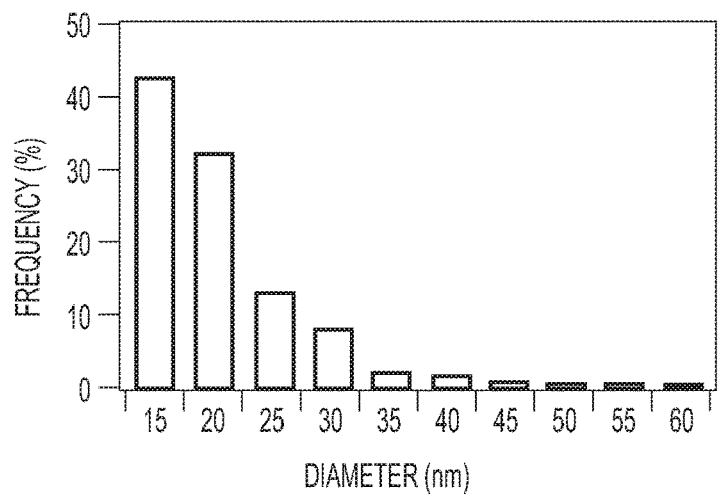
FIGS. 2A, 2B, 2C and 2D are graphs showing frequency (%) as a function of particle size for PLA-HPG nanoparticles.
Figure 2B:
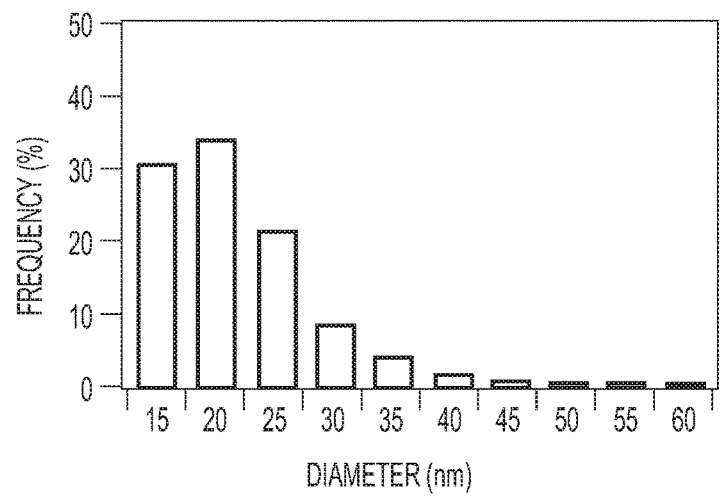
Figure 2C:
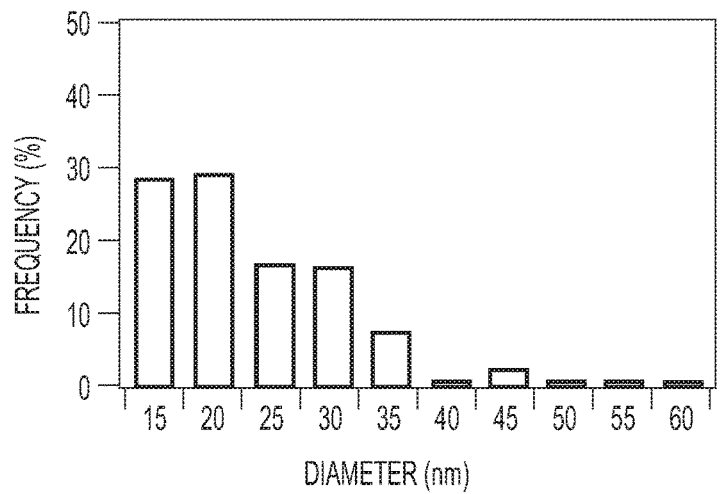
Figure 2D:
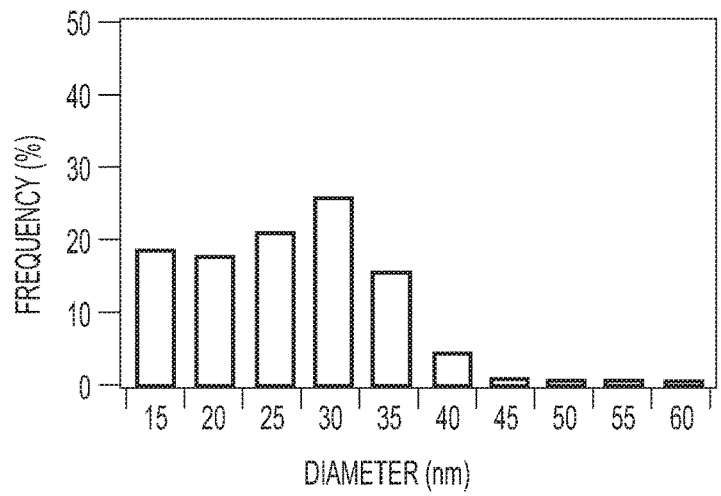

"Effective amount" or "therapeutically effective amount", as used herein, refers to an amount of drug effective to alleviate, delay onset of, or prevent one or more symptoms of a disease or disorder.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, subjunctivally, by injection, and by infusion.

"Enteral administration", as used herein, means administration via absorption through the gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "copolymer" as used herein, generally refers to a single polymeric material that is comprised of two or more different monomers. The copolymer can be of any form, such as random, block, graft, etc. The copolymers can have any end-group, including capped or acid end groups.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as, but not limited to, a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

The term "lipophilic", as used herein, refers to compounds having an affinity for lipids.

The term "amphiphilic", as used herein, refers to a molecule combining hydrophilic and lipophilic (hydrophobic) properties.

"Nanoparticle", as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle", as used herein, generally refers to a particle having a diameter, such as an average diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape are generally referred to as "microspheres".

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—NH$_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

"About" is intended to describe values either above or below the stated value in a range of approx. +/−10%. The ranges are intended to be made clear by context, and no further limitation is implied. The use of any and all examples, or exemplary language (e.g., "such as") provided herein, is intended merely to better illuminate the description and does not pose a limitation on the scope of the description unless otherwise claimed.

II. Core-shell Microparticles and Nanoparticles

A. Core

The core of the particles is formed of or contains one or more hydrophobic or more hydrophobic materials, such as one or more polymeric materials (e.g., homopolymer, copolymer, terpolymer, etc.). The material may be biodegradable or non-biodegradable. In some embodiments, the one or more materials are one or more biodegradable polymers.

In general, synthetic polymers are preferred, although natural polymers may be used and have equivalent or even better properties, especially some of the natural biopolymers which degrade by hydrolysis, such as some of the polyhydroxyalkanoates. Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof.

In certain embodiments, the hydrophobic polymer is an aliphatic polyester. In preferred embodiments, the hydrophobic polymer is a polyhydroxyester such as poly(lactic acid), poly(glycolic acid), or poly(lactic acid-co-glycolic acid).

The particles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. The hydrophobic poly (lactic acid) (PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

The core can be formed of copolymers including amphiphilic copolymers such as PLGA-PEG or PLURONICS® (block copolymers of polyethylene oxide-polypropylene glycol) but this may decrease the benefit of the polyglycerol molecules discussed below.

Other materials may also be incorporated including lipids, fatty acids, and phospholipids. These may be dispersed in or on the particles, or interspersed with the polyglycerol coatings discussed below.

B. Shell

The particles described herein contain a shell or coating containing hyperbranched polyglycerol (HPG).

Hyperbranched polyglycerol is a highly branched polyol containing a polyether scaffold. Hyperbranched polyglycerol can be prepared using techniques known in the art. It can be formed from controlled etherification of glycerol via cationic or anionic ring opening multibranching polymerization of glycidol. For example, an initiator having multiple reactive sites is reacted with glycidol in the presence of a base to form hyperbranched polyglycerol (HPG). Suitable initiators include, but are not limited to, polyols, e.g., triols, tetraols, pentaols, or greater and polyamines, e.g., triamines, tetraamines, pentaamines, etc. In one embodiment, the initiator is 1,1,1-trihydroxymethyl propane (THP).

A formula for hyperbranched polyglycerol as described in EP 2754684 is

Formula I

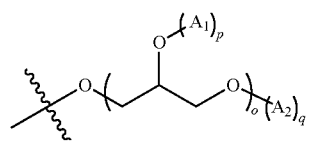

wherein o, p and q are independently integers from 1-100, wherein $A_1$ and $A_2$ are independently Formula II

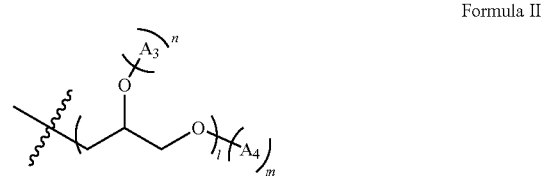

wherein l, m and n are independently integers from 1-100. wherein $A_3$ and $A_4$ are defined as $A_1$ and $A_2$, with the proviso that $A_3$ and $A_4$ are hydrogen, n and m are each 1 for terminal residues.

The surface properties of the HPG can be tuned based on the chemistry of vicinal diols. For example, the surface properties can be tuned to provide stealth particles, i.e., particles that are not cleared by the MPS due to the presence of the hydroxyl groups; adhesive (sticky) particles, i.e., particles that adhere to the surface of tissues, for example, due to the presence of one or more reactive functional groups, such as aldehydes, amines, oxime, or O-substituted oxime that can be prepared from the vicinal hydroxyl moieties; or targeting by the introduction of one or more targeting moieties which can be conjugated directly or indirectly to the vicinal hydroxyl moieties. Indirectly refers to transformation of the hydroxy groups to reactive functional groups that can react with functional groups on molecules to be attached to the surface, such as active agents and/or targeting moieties, etc. A schematic of this tunability is shown in FIGS. 1A, 1B, and 1C.

The hyperbranched nature of the polyglycerol allows for a much higher density of hydroxyl groups, reactive functional groups, and/or targeting moieties than polyethylene glycol. For example, the particles described herein can have a density of surface functionality (e.g., hydroxyl groups, reactive functional groups, and/or targeting moieties) of at least about 1, 2, 3, 4, 5, 6, 7, or 8 groups/nm².

The molecular weight of the HPG can vary. For example, in those embodiments wherein the HPG is covalently attached to the materials or polymers that form the core, the molecular weight can vary depending on the molecular weight and/or hydrophobicity of the core materials. The molecular weight of the HPG is generally from about 1,000 to about 1,000,000 Daltons, from about 1,000 to about 500,000 Daltons, from about 1,000 to about 250,000 Daltons, or from about 1,000 to about 100,000 Daltons. In those embodiments wherein the HPG is covalently bound to the core materials, the weight percent of HPG of the copolymer is from about 1% to about 50%, such as about 1, 2, 3, 4, 5, 10, 15, 20, 25, 30, 35, 40, 45 or 50%.

In some embodiments, the HPG is covalently coupled to a hydrophobic material or a more hydrophobic material, such as a polymer. Upon self-assembly, particles are formed containing a core containing the hydrophobic material and a shell or coating of HPG. HPG coupled to the polymer PLA is shown below:

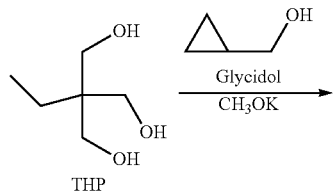

THP

-continued

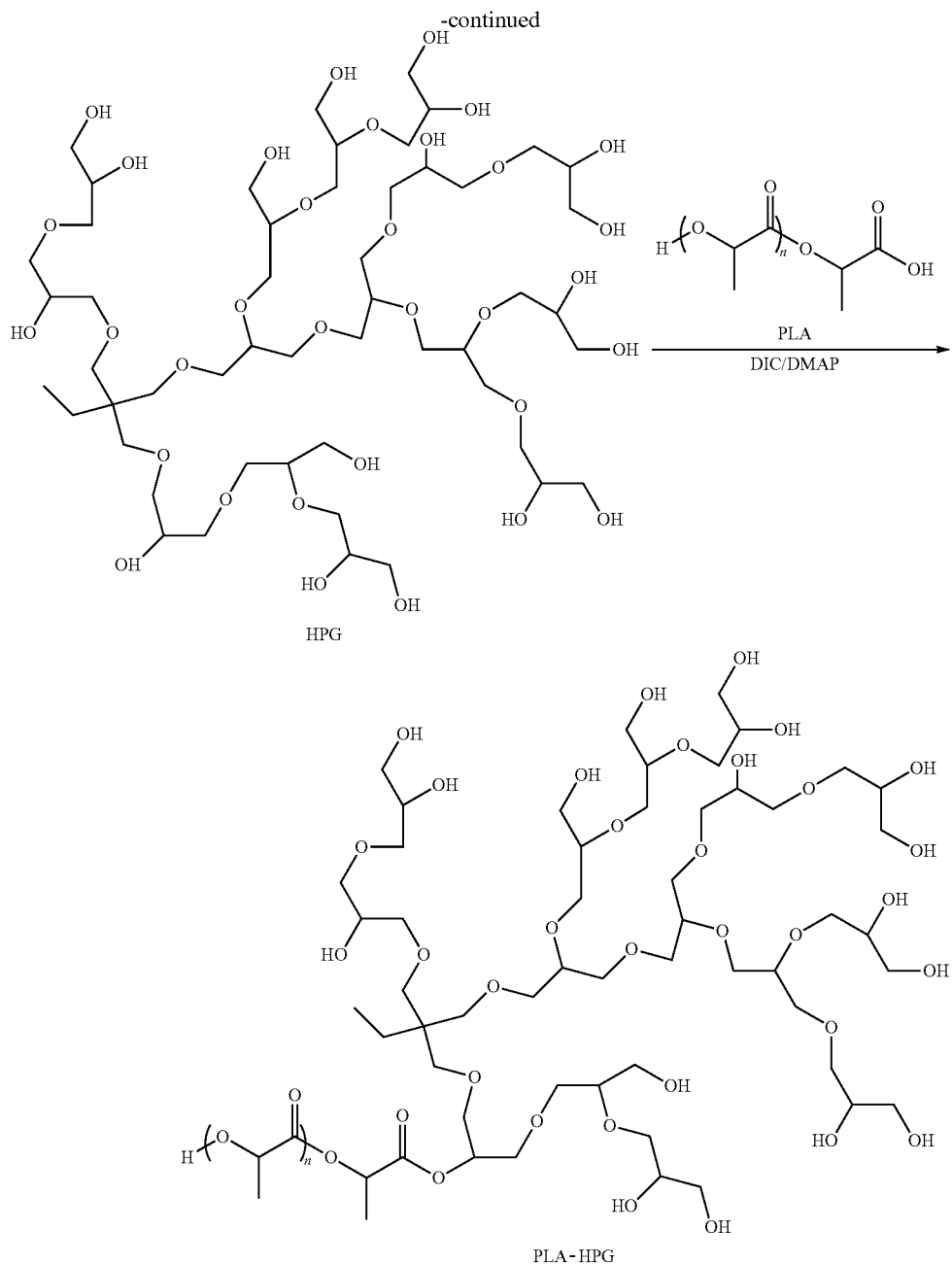

HPG

PLA-HPG

C. Molecules to be Encapsulated or Attached to the Surface of the Particles

The particles described herein may contain one or more molecules encapsulated within and/or attached to the surface of the particles. The molecules can be covalently or non-covalently associated with the particles. In some embodiments, the molecules are targeting moieties which are covalently associated with the particles. In particular embodiments, the targeting moieties are covalently bound to the HPG coating via the hydroxy groups on HPG. The targeting moieties can be bound directly to HPG or via a coupling agent. In other embodiments, the particles have encapsulated therein one or more therapeutic agents, diagnostic agents, prophylactic agents, and/or nutraceuticals. In some embodiments, the particles contain both targeting agents which are covalently or non-covalently associated with the particles and one or more therapeutic agents, diagnostic agents, prophylactic agents, and/or nutraceuticals which are covalently or non-covalently associated with the particles.

1. Covalently Bound Molecules

Molecules can be bound to the hydroxy groups on HPG before or after particle formation. Representative methodologies for conjugated molecules to the hydroxy groups on HPG are described below.

One useful protocol involves the "activation" of hydroxyl groups with carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Alternatively, the hydroxyl groups can be converted to reactive functional group that can react with a reactive functional group on the molecule to be attached. For example, the hydroxyl groups on HPG can be converted to aldehydes, amines, or O-substituted oximes which can react with reactive functional groups on molecules to be attached. Such transformations can be done before or after particle formation.

Any suitable coupling method known to those skilled in the art for the coupling of ligands and polymers with double bonds, including the use of UV crosslinking, may be used for attachment of molecules to the polymer.

Coupling is preferably by covalent binding but it may also be indirect, for example, through a linker bound to the polymer or through an interaction between two molecules such as streptavidin and biotin. It may also be by electrostatic attraction by dip-coating.

The coupling methods can be done before or after particle formation.

2. Therapeutic Agent, Diagnostic Agents, Prophylactic Agents, and/or Nutraceuticals Agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered. The preferred materials to be incorporated are drugs and imaging agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, epothilones A-F, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs, antisense, aptamers, ribozymes, external guide sequences for ribonuclease P, and triplex forming agents).

Particularly preferred drugs to be delivered include anti-angiogenic agents, antiproliferative and chemotherapeutic agents such as rampamycin. Incorporated into particles, these agents may be used to treat cancer or eye diseases, or prevent restenosis following administration into the blood vessels.

Representative classes of diagnostic materials include paramagnetic molecules, fluorescent compounds, magnetic molecules, and radionuclides. Exemplary materials include, but are not limited to, metal oxides, such as iron oxide, metallic particles, such as gold particles, etc. Biomarkers can also be conjugated to the surface for diagnostic applications.

One or more active agents may be formulated alone or with excipients or encapsulated on, in or incorporated into the microparticles or nanoparticles. Active agents include therapeutic, prophylactic, neutraceutical and diagnostic agents. Any suitable agent may be used. These include organic compounds, inorganic compounds, proteins, polysaccharides, nucleic acids or other materials that can be incorporated using standard techniques.

Active agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof. Suitable active agents have a size greater than about 1,000 Da for small peptides and polypeptides, more typically at least about 5,000 Da and often 10,000 Da or more for proteins. Nucleic acids are more typically listed in terms of base pairs or bases (collectively "bp"). Nucleic acids with lengths above about 10 bp are typically used in the present method. More typically, useful lengths of nucleic acids for probing or therapeutic use will be in the range from about 20 bp (probes; inhibitory RNAs, etc.) to tens of thousands of bp for genes and vectors. The active agents may also be hydrophilic molecules, preferably having a low molecular weight.

Examples of useful proteins include hormones such as insulin and growth hormones including somatomedins. Examples of useful drugs include neurotransmitters such as L-DOPA, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, synthetic hormones such as Android F from Brown Pharmaceuticals and Tes-tred® (methyltestosterone) from ICN Pharmaceuticals.

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel, epothilones A-F, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), and combinations thereof. Other suitable anti-cancer agents include angiogenesis inhibitors including antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (NEXAVAR®), erlotinib (TARCEVA®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Under the Biopharmaceutical Classification System (BCS), drugs can belong to four classes: class I (high permeability, high solubility), class II (high permeability, low solubility), class III (low permeability, high solubility) or class IV (low permeability, low solubility). Suitable active agents also include poorly soluble compounds; such as drugs that are classified as class II or class IV compounds using the BCS. Examples of class II compounds include: acyclovir, nifedipine, danazol, ketoconazole, mefenamic acid, nisoldipine, nicardipine, felodipine, atovaquone, griseofulvin, troglitazone glibenclamide and carbamazepine. Examples of class IV compounds include: chlorothiazide, furosemide, tobramycin, cefuroxmine, and paclitaxel.

For imaging, radioactive materials such as Technetium99 ($^{99m}$Tc) or magnetic materials such as $Fe_2O_3$ could be used. Examples of other materials include gases or gas emitting compounds, which are radioopaque.

Alternatively, the biodegradable polymers may encapsulate cellular materials, such as for example, cellular materials to be delivered to antigen presenting cells as described below to induce immunological responses.

Peptide, protein, and DNA based vaccines may be used to induce immunity to various diseases or conditions. For example, sexually transmitted diseases and unwanted pregnancy are world-wide problems affecting the health and welfare of women. Effective vaccines to induce specific immunity within the female genital tract could greatly reduce the risk of STDs, while vaccines that provoke anti-sperm antibodies would function as immunocontraceptives. Extensive studies have demonstrated that vaccination at a distal site—orally, nasally, or rectally, for example—can induce mucosal immunity within the female genital tract. Of these options, oral administration has gained the most interest because of its potential for patient compliance, easy administration and suitability for widespread use. Oral vaccination with proteins is possible, but is usually inefficient or requires very high doses. Oral vaccination with DNA, while potentially effective at lower doses, has been ineffective in most cases because 'naked DNA' is susceptible to both the stomach acidity and digestive enzymes in the gastrointestinal tract Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA-based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Biodegradable polymer particles offer several advantages for use as DNA delivery vehicles for DNA based vaccines. The polymer particles can be biodegradable and biocompatible, and they have been used successfully in past therapeutic applications to induce mucosal or humoral immune responses. Polymer biodegradation products are typically formed at a relatively slow rate, are biologically compatible, and result in metabolizable moieties. Biodegradable polymer particles can be manufactured at sizes ranging from diameters of several microns (microparticles) to particles having diameters of less than one micron (nanoparticles).

Dendritic cells (DCs) are recognized to be powerful antigen presenting cells for inducing cellular immunologic responses in humans. DCs prime both CD8+cytotoxic T-cell (CTL) and CD4+ T-helper (Th1) responses. DCs are capable of capturing and processing antigens, and migrating to the regional lymph nodes to present the captured antigens and induce T-cell responses. Immature DCs can internalize and process cellular materials, such as DNA encoding antigens, and induce cellular immunologic responses to disease effectors.

As used herein, the term "disease effector agents" refers to agents that are central to the causation of a disease state in a subject. In certain circumstances, these disease effector agents are disease-causing cells which may be circulating in the bloodstream, thereby making them readily accessible to extracorporeal manipulations and treatments. Examples of such disease-causing cells include malignant T cells, malignant B cells, T cells and B cells which mediate an autoimmune response, and virally or bacterially infected white blood cells which express on their surface viral or bacterial peptides or proteins. Exemplary disease categories giving rise to disease-causing cells include leukemia, lymphoma, autoimmune disease, graft versus host disease, and tissue rejection. Disease associated antigens which mediate these disease states and which are derived from disease-causing cells include peptides that bind to a MHC Class I site, a MHC Class II site, or to a heat shock protein which is involved in transporting peptides to and from MHC sites (i.e., a chaperone). Disease associated antigens also include viral or bacterial peptides which are expressed on the surface of infected white blood cells, usually in association with an MHC Class I or Class II molecule.

Other disease-causing cells include those isolated from surgically excised specimens from solid tumors, such as lung, colon, brain, kidney or skin cancers. These cells can be manipulated extracorporeally in analogous fashion to blood leukocytes, after they are brought into suspension or propagated in tissue culture. Alternatively, in some instances, it has been shown that the circulating blood of patients with solid tumors can contain malignant cells that have broken off from the tumors and entered the circulation. These circulating tumor cells can provide an easily accessible source of cancer cells which may be rendered apoptotic and presented to the antigen presenting cells.

In addition to disease-causing cells, disease effector agents include microbes such as bacteria, fungi, yeast, viruses which express or encode disease-associated antigens, and prions.

The disease effector agents are presented to the antigen presenting cells using biodegradable polymer particles as delivery vehicles. The loaded particles are exposed to immature antigen presenting cells, which internalize the particles and process the material within the particles. The particles may be administered to the patient and the interaction between the particles and the antigen presenting cells may occur in vivo. In a preferred embodiment, the particles are placed in an incubation bag with the immature antigen presenting cells, and the particles are phagocytosed by the antigen presenting cells during the incubation period. The resulting antigen presenting cells are then administered to the patient to induce an immune response to the disease causing agent.

Other agents include cell penetrating peptides, such as TAT, Antennapedia, polyarginine and poly-lysine analogues.

3. Targeting Moieties

The particles, such as the surface of the particles, can be modified to facilitate targeting through the attachment of targeting molecules.

Exemplary target molecules include proteins, peptides, nucleic acids, lipids, saccharides, or polysaccharides, or small molecules that bind to one or more targets associated with an organ, tissue, cell, or extracellular matrix, or specific type of tumor or infected cell. The degree of specificity with which the particles are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer*, 2:83-90 (2002). Targeting molecules can also include neuropilins and endothelial targeting molecules, integrins, selectins, and adhesion molecules.

Targeting molecules can be covalently bound to particles using a variety of methods known in the art. In some embodiments, the targeting moieties are covalently associated with the polymer, preferably via a linker cleaved at the site of delivery.

The nanoparticles can contain one or more polymer conjugates containing end-to-end linkages between the polymer and a targeting element or a detectable label. For example, a modified polymer can be a PLA-HPG-peptide block polymer.

Examples of targeting moieties include peptides such as iRGD, LyP1; small molecule such as folate, aptamers and antibodies or their combinations at various molar ratios.

The targeting element of the nanoparticle can be an antibody or antigen binding fragment thereof. The targeting elements should have an affinity for a cell-surface receptor or cell-surface antigen on the target cells and result in internalization of the particle within the target cell.

The targeting element can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

Additional targets that can be recognized by the targeting element include VEGF/KDR, Tie2, vascular cell adhesion molecule (VCAM), endoglin and $\alpha_5\beta_3$ integrin/vitronectin. The targeting peptides can be covalently associated with the polymer of the outer shell and the covalent association can be mediated by a linker.

Tumor-specific and Tumor-associated Antigens

In one embodiment the targeting element specifically binds to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al., *Int. J. Cancer*, 106:817-20 (2003); Kennedy, et al., *Int. Rev. Immunol.*, 22:141-72 (2003); Scanlan, et al. *Cancer Immun.*, 4:1 (2004)).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.*, 309:883 (1983); Lloyd, et al., *Int. J. Canc.*, 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.*, 36:755 (1997); Sarandakou, et al., *Eur. J. Gynaecol. Oncol.*, 19:73 (1998); Meier, et al., *Anticancer Res.*, 17(4B):2945 (1997); Kudoh, et al., *Gynecol. Obstet. Invest.*, 47:52 (1999)). Elevated serum CA125 may also accompany neuroblastoma (e.g., Hirokawa, et al., *Surg. Today*, 28:349 (1998), while elevated CEA and SCC, among others, may accompany colorectal cancer (Gebauer, et al., *Anticancer Res.*, 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.*, 52:181 (1992); Chang, et al., *Int. J. Cancer*, 50:373 (1992); Chang, et al., *Int. J. Cancer*, 51:548 (1992); Chang, et al., *Proc. Natl. Acad. Sci. USA*, 93:136 (1996); Chowdhury, et al., *Proc. Natl. Acad. Sci. USA*, 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer*, 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.*, 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature*, 366:473 (1993); GenBank Acc. Nos. L07868 and T64105), epidermal growth factor receptor (EGFR) (GenBank Acc. Nos. U48722, and KO3193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA*, 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA*, 86:7159 (1989); GenBank Acc. Nos. M65132 and M64928) NY-ESO-1 (GenBank Acc. Nos. AJ003149 and U87459), NA 17-A (PCT Publication No. WO 96/40039), Melan-A/ MART-1 (Kawakami, et al., *Proc. Nat. Acad. Sci. USA*, 91:3515 (1994); GenBank Acc. Nos. U06654 and U06452), tyrosinase (Topalian, et al., *Proc. Nat. Acad. Sci. USA*, 91:9461 (1994); GenBank Acc. No. M26729; Weber, et al., *J. Clin. Invest*, 102:1258 (1998)), Gp-100 (Kawakami, et al., *Proc. Nat. Acad. Sci. USA*, 91:3515 (1994); GenBank Acc. No. S73003, Adema, et al., *J Biol. Chem.*, 269:20126 (1994)), MAGE (van den Bruggen, et al., *Science*, 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683, 886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, *J Exp. Med.*, 121:439 (1985); GenBank Acc. Nos. M59710, M59255 and M29540), and PyLT (GenBank Acc. Nos. J02289 and J02038); p97 (melanotransferrin) (Brown, et al., *J. Immunol.*, 127:539-46 (1981); Rose, et al., *Proc. Natl. Acad. Sci. USA*, 83:1261-61 (1986)).

Additional tumor associated antigens include prostate surface antigen (PSA) (U.S. Pat. Nos. 6,677,157; 6,673, 545); β-human chorionic gonadotropin β-HCG) (McManus, et al., *Cancer Res.*, 36:3476-81 (1976); Yoshimura, et al., *Cancer*, 73:2745-52 (1994); Yamaguchi, et al., *Br. J. Cancer*, 60:382-84 (1989): Alfthan, et al., *Cancer Res.*, 52:4628-33 (1992)); glycosyltransferase β-1,4-N-acetylgalactosaminyl-transferases (GalNAc) (Hoon, et al., *Int. J. Cancer*, 43:857-62 (1989); Ando, et al., *Int. J. Cancer*, 40:12-17 (1987); Tsuchida, et al., *J. Natl. Cancer*, 78:45-54 (1987); Tsuchida, et al., *J. Natl. Cancer*, 78:55-60 (1987)); NUC18 (Lehmann, et al., *Proc. Natl. Acad. Sci. USA*, 86:9891-95 (1989); Lehmann, et al., *Cancer Res.*, 47:841-45 (1987)); melanoma antigen gp75 (Vijayasardahi, et al., *J. Exp. Med.*, 171:1375-80 (1990); GenBank Accession No. X51455); human cytokeratin 8; high molecular weight melanoma antigen (Natali, et al., *Cancer*, 59:55-63 (1987); keratin 19 (Datta, et al., *J. Clin. Oncol.*, 12:475-82 (1994)).

Tumor antigens of interest include antigens regarded in the art as "cancer/testis" (CT) antigens that are immunogenic in subjects having a malignant condition (Scanlan, et al., *Cancer Immun.*, 4:1 (2004)). CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE- 6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the fusion proteins.

Peptide Targeting Elements

The targeting element can be a peptide. Specifically, the plaque targeted peptide can be, but is not limited to, one or more of the following: RGD, iRGD(CRGDK/RGPD/EC), LyP-1, P3(CKGGRAKDC), or their combinations at various molar ratios. The targeting peptides can be covalently associated with the polymer and the covalent association can be mediated by a linker.

Antibody Targeting Elements

The targeting element can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')$_2$, dsFv, sFv, diabodies, and triabodies. In certain embodiments, the antibody is a single chain antibody.

Aptamer Targeting Elements

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

Other Targeting Moieties

The outer surface of the particle may be treated using a mannose amine, thereby mannosylating the outer surface of the particle. This treatment may cause the particle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins that can be covalently attached to particles to render them target specific to the mucin and mucosal cell layer include lectins isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus.*

The attachment of any positively charged ligand, such as polyethyleneimine or polylysine, to any particle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most particles with the appropriate chemistry, and be expected to influence the binding of particles to the gut. For example, polyclonal antibodies raised against components of mucin or else intact mucin, when covalently coupled to particles, would provide for increased bioadhesion. Similarly, antibodies directed against specific cell surface receptors exposed on the lumenal surface of the intestinal tract would increase the residence time of beads, when coupled to particles using the appropriate chemistry. The ligand affinity need not be based only on electrostatic charge, but other useful physical parameters such as solubility in mucin or else specific affinity to carbohydrate groups.

The covalent attachment of any of the natural components of mucin in either pure or partially purified form to the particles would decrease the surface tension of the bead-gut interface and increase the solubility of the bead in the mucin layer. The list of useful ligands would include but not be limited to the following: sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range would yield chains of 120 to 425 amino acid residues attached to the surface of the particles. The polyamino chains would increase bioadhesion by means of chain entanglement in mucin strands as well as by increased carboxylic charge.

4. Sheddable Polyethylene Glycol (PEG) Coatings

The HPG-coated particles can be modified by covalently attaching PEG to the surface. This can be achieved by converting the vicinyl diol groups to aldehydes and then reacting the aldehydes with functional groups on PEG, such as aliphatic amines, aromatic amines, hydrazines and thiols. The linker has end groups such as aliphatic amines, aromatic amines, hydrazines, thiols and O-substituted oxyamines. The bond inserted in the linker can be disulfide, orthoester and peptides sensitive to proteases.

PEG with a functional group or a linker can form a bond with aldehyde on PLA-HPGALD and reversed the bioadhesive (sticky) state of PLA-HPGALD to stealth state. This bond or the linker is labile to pH change or high concentration of peptides, proteins and other biomolecules. "ALD" denotes an aldehyde. After administration systematically or locally, the bond attaching the PEG to PLA-HPGALD can be reversed or cleaved to release the PEG in response to environment and exposed the PLA-HPGALD particles to the environment. Subsequently, the particles will interact with the tissue and attach the particles to the tissues or extracellular materials such as proteins. The environment can be acidic environment in tumors, reducing environment in tumors, protein rich environment in tissues.

III. Pharmaceutical Compositions

The particles can be formulated with appropriate pharmaceutically acceptable carriers into pharmaceutical compositions for administration to an individual in need thereof. The formulations can be administered enterally (e.g., oral) or parenterally (e.g., by injection or infusion). Other routes of administration include, but are not limited to, transdermal.

The compounds can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Enteral formulations are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins.

Carrier also includes all components of the coating composition which may include plasticizers, pigments, colorants, stabilizing agents, and glidants. Formulations can be prepared using one or more pharmaceutically acceptable excipients, including diluents, preservatives, binders, lubricants, disintegrators, swelling agents, fillers, stabilizers, and combinations thereof.

Controlled release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, P A: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

IV. Methods of Making Particles

A. Hyperbranched Polyglycerol (HPG)

Hyperbranched polyglycerol can be prepared using techniques known in the art. For example, an initiator having multiple reactive sites is reacted with glycidol in the presence of a base to form hyperbranched polyglycerol (HPG). Suitable initiators include, but are not limited to, polyols, e.g., triols, tetraols, pentaols, or greater and polyamines, e.g., triamines, tetraamines, pentaamines, etc. In one embodiment, the initiator is 1,1,1-trihydroxymethyl propane (THP).

B. Polymer-HPG Conjugates

Hyperbranched polyglycerol (HPG) can be covalently bound to one or more materials, such as a polymer, that form the core of the particles using methodologies known in the art. For example, HPG can be covalently coupled to a polymer having carboxylic acid groups, such as PLA, PGA, or PLGA using DIC/DMAP.

The HPG can be functionalized to introduce one or more reactive functional groups that alter the surface properties of the particles. For example, HPG-coated particles prevent non-specific adsorption of serum proteins and increase the blood circulation of the particles. Such particles are referred to as stealth particle. However, the hydroxyl groups on HPG can be chemically modified to cause the particles to stick to biological material, such as tissues, organs, cells, etc. Such functional groups include aldehydes, amines, O-substituted oximes, and combinations thereof. A synthetic scheme for such chemical conversions is shown in FIG. 1.

C. Particles

Methods of making polymeric particles are known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In some embodiments, the particles are prepared using an emulsion-based technique. In particular embodiments, the particles are prepared using a double emulsion solvent evaporation technique. For example, the amphiphilic material and the hydrophobic cationic material are dissolved in a suitable organic solvent, such as methylene chloride or dichloromethane (DCM), with or without a therapeutic agent. The siRNA is reconstituted in purified water, such as HyPure™ molecular biology grade water (Hyclone Laboratories, Inc., Logan, Utah). The siRNA solution is added dropwise to the solution of the amphiphilic material and the hydrophobic cationic material and emulsified to form a first emulsion. The emulsion is added to an aqueous solution of surfactant, such as PVA, to form a double emulsion. The final emulsion is added to water and stirred for an extended period of time (e.g., 3 hours) to allow the organic solvent to evaporate and the particles to harden. Residual organic solvent and/or unencapsulated molecules are removed by washing. Other emulsion emulsion-based procedures are described below.

1. Phase Separation Microencapsulation

In phase separation microencapsulation techniques, a polymer solution is stirred, optionally in the presence of one or more active agents to be encapsulated. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

2. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

3. Solvent Evaporation Microencapsulation

Methods for forming microspheres using solvent evaporation techniques are described in E. Mathiowitz et al., J. Scanning Microscopy, 4:329 (1990); L. R. Beck et al., Fertil. Steril., 31:545 (1979); L. R. Beck et al, Am. J Obstet. Gynecol., 135(3) (1979); S. Benita et al., J. Pharm. Sci., 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microparticles/nanoparticles. This method is useful for relatively stable polymers like polyesters and polystyrene.

4. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

5. Microfluidics

Nanoparticles can be prepared using microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution. The targeted peptides or fluorophores or drugs may be associated with the surface of, encapsulated within, surrounded by, and/or distributed throughout the polymeric matrix of the particles.

6. Particle Properties

The particles may have any zeta potential. The particles can have a zeta potential from −300 mV to +300 mV, −100 mV to +100 mV, from −50 mV to +50 mV, from −40 mV to +40 mV, from −30 mV to +30 mV, from −20 mV to +20 mV, from −10 mV to +10 mV, or from −5 mV to +5 mV. The particles can have a negative or positive zeta potential. In some embodiments the particles have a substantially neutral zeta potential, i.e. the zeta potential is approximately 0 mV. In preferred embodiments the particles have a zeta potential of approximately −30 to about 30 mV, preferably from about −20 to about 20 mV, more preferably from about −10 to about 10 mV.

The particles may have any diameter. The particles can have a diameter of between about 1 nm and about 1000 microns, about 1 nm and about 100 microns, about 1 nm and about 10 microns, about 1 nm and about 1000 nm, about 1 nm and about 500 nm, about 1 nm and about 250 nm, or about 1 nm and about 100 nm. In preferred embodiments, the particle is a nanoparticle having a diameter from about 25 nm to about 250 nm. In more preferred embodiments, the particles are nanoparticles having a diameter from about 180 nm to about 250 nm, preferably from about 180 nm to about 230 nm. Particles size typically is based on a population, wherein 60, 70, 80, 85, 90, or 95% of the population has the desired size range.

The polydispersity is from about 0.05 to 0.30, preferably from about 0.05 to about 0.25, more preferably from about 0.05 to about 0.20, more preferably from about 0.05 to about 0.15, most preferably from about 0.05 to about 0.10.

V. Methods of Using Particles

The particles described herein can be used for a variety of applications including drug delivery, tissue engineering, etc. In some embodiments, the particles are "stealth" particles, where the hydroxyl groups on HPG increase circulation in the blood stream by resisting non-specific serum-protein absorption and subsequent uptake by the MPS. This can allow targeted particles to be delivered to the desired site for drug release. Alternatively, the vicinyl diol groups can be converted to functional groups that adhere to biological materials, such as tissue, organs, cells, proteins, etc. Such particles are referred to as "sticky".

A. Drug Delivery

PEG has been widely used as a coating in biomaterials and drug delivery systems. It is commonly accepted that the properties of PEG result from a combination of its neutral charge, molecular flexibility, and hydrophilicity. The use of PEG has become so dominant in the field of particulate drug delivery, that alternatives are rarely examined.

HPG is a hyperbranched, hydrophilic polymer with a high density of hydroxyl groups on its surface: it is more hydrophilic than PEG and has been demonstrated to have better compatibility and non-specific resistance to biomolecules than PEG in certain applications. HPG is well known to have a lower intrinsic viscosity than linear PEG, which decreases the possibility of red cell aggregation when present in the circulation.

While HPG has been explored in a variety of biomedical settings, principally for coatings on implanted materials, it has never before been tested as a surface coating for drug delivery systems. The examples demonstrate that HPG has substantially improved properties compared to PEG when conjugated to NPs and that these properties result from its higher hydrophilicity leading to a better effect and more stability in suspension. Therefore, NPs coated with HPG should be more effective in clinical medicine than NPs coated with PEG.

Certain properties of the PLA-HPG conjugate are important for the observed effects. Because high molecular weight HPG has better resistance of non-specific adsorption to biomolecules, the low molecular weight components were removed from the synthesized HPG by multiple solvent precipitations and dialysis.

PLA was selected as the hydrophobic core material because it is biodegradable, has a long history of clinical use, and is the major component of a NP system that is advancing in clinical trials. To covalently attach the PLA to HPG, the previous approach was to first functionalize the HPG with an amine and then conjugate the carboxylic group on PLA to the amine. This approach is efficient but cannot be used to make HPG as surface coatings since any amines that do not react with PLA will lead to a net positive charge on the neutral HPG surface and reduce the ability of HPG to resist adsorption of other molecules on the surface. To avoid this, the approach in the examples used a one-step esterification between PLA and HPG, which maintained the charge neutral state of the HPG.

Blood circulation and biodistribution are standard methods used to examine the surface effect in vivo. NPs coated with certain coatings tend to escape the MPS and circulate longer in blood. Although it is known that PEG coatings can significantly enhance blood circulation of NPs and reduce accumulation in the liver, the majority of injected PEG-coated NPs still accumulate in the liver. In contrast, the HPG coating on PLA NPs produced much lower NP accumulation in the liver. With different markers, labeling and detection methods, the absolute value of biodistribution of NPs varies. This makes it difficult to compare the data to other NP formulations. However the liver to blood ratio of PLA-HPG NPs, approximately ⅓ at 12 hr and approximately 1 at 24 hr, is comparable to that of BIND-014, a PLA-PEG NP formulation in clinical trials, that was optimized from more than 100 NP formulations. Surprisingly, the spleen to blood ratio of PLA-HPG NPs, approximately ⅔ at 12 h and ~1 at 24 h, is even lower than that of BIND-014.

Nanoparticles accumulate in tumors through the enhanced permeability and retention (EPR) effect, which results from leaky vasculature of the tumor. Both PLA-HPG NPs and PLA-PEG NPs have a hydrodynamic diameter of 100 nm. Notably, tumor accumulation of PLA-HPG NPs is ~3 times greater than accumulation of PLA-PEG NPs. This enhanced tumor accumulation of PLA-HPG NPs over PLA-PEG NPs may be due to the enhanced blood circulation time, which is conferred by their surface coatings. Penetration of the PLA-HPG NPs was further confirmed by immunohistochemistry.

To demonstrate that PLA-HPG NPs were improved carriers for drugs, therapeutic studies of PLA-HPG NPs having encapsulated therein the chemotherapy drug camptothecin (CPT) were performed on mice bearing subcutaneous LLC tumors. CPT was selected because it is known to be effective against a wide variety of tumors, but it is limited in clinical use by very low solubility and side effects. PLA-HPG/CPT NPs provided significantly better tumor treatment than PLA-PEG/CPT NPs. In most respects, the two NPs were similar: PLA-HPG and PLA-PEG NPs had similar weight percentage of surface coating; both PLA-HPG/CPT NPs and PLA- PEG/CPT NPs had enhanced in vitro cytotoxicity; PLA-HPG/CPT NPs were similar in size to PLA-PEG/CPT NPs; PLA-HPG/CPT and PLA-PEG/CPT NPs showed similar in vitro release profiles of CPT. The most notable difference between the two NP formulations is the presence of HPG versus PEG. Therefore, it is believed that the improved therapeutic effectiveness of PLA-HPG/CPT NPs is due to the greater emulsion stability, improved blood circulation time, improved biodistribution, and improved tumor penetration that result from HPG.

The submicron size of nanoparticulates offers distinct advantages over larger systems. First, the small size enables them to extravasate through blood vessels and tissue. This is especially important for tumor vessels, which are often dilated and fenestrated with an average pore size less than a micron, compared to normal tissue. Second, solid nanoparticles made from biodegradable polymers and encapsulating drug are ideal for sustained intracellular drug delivery, especially for drugs whose targets are cytoplasmic. An example of this application with dexamethasone-loaded nanoparticles locally delivered to vascular smooth muscle cells showed greater and sustained anti-proliferative activity compared to free drug, indicating more efficient interaction of the drug with cytoplasmic glucorticoid receptors. The dosage loading varies depending on the nature of encapsulant. Up to 80% of initial total amount of agent to be incorporated can be encapsulated in the particles.

The particles are useful in drug delivery (as used herein "drug" includes therapeutic, nutritional, diagnostic and prophylactic agents), whether injected intravenously, subcutaneously, or intramuscularly, administered to the nasal or pulmonary system, administered to a mucosal surface (vaginal, rectal, buccal, sublingual), or encapsulated for oral delivery. As noted above, the term "microparticle" includes "nanoparticles" unless otherwise stated. The dosage is determined using standard techniques based on the drug to be delivered and the method and form of administration. The particles may be administered as a dry powder, as an aqueous suspension (in water, saline, buffered saline, etc.), in a hydrogel, organogel, or liposome, in capsules, tablets, troches, or other standard pharmaceutical excipient.

In a preferred embodiment for delivery to a mucosal surface, the particles are modified to include ligands for mucosal proteins or extracellular matrix as described above.

1. Restenosis and Transplantation

Percutaneous transluminal coronary angioplasty (PTCA) is a procedure in which a small balloon-tipped catheter is passed down a narrowed coronary artery and then expanded to re-open the artery. It is currently performed in approximately 250,000-300,000 patients each year. The major advantage of this therapy is that patients in which the procedure is successful need not undergo the more invasive surgical procedure of coronary artery bypass graft. A major difficulty with PTCA is the problem of post-angioplasty closure of the vessel, both immediately after PTCA (acute reocclusion) and in the long term (restenosis).

The mechanism of acute reocclusion appears to involve several factors and may result from vascular recoil with resultant closure of the artery and/or deposition of blood platelets along the damaged length of the newly opened blood vessel followed by formation of a fibrin/red blood cell thrombus. Restenosis (chronic reclosure) after angioplasty is a more gradual process than acute reocclusion: 30% of patients with subtotal lesions and 50% of patients with chronic total lesions will go on to restenosis after angioplasty. Although the exact hormonal and cellular processes promoting restenosis are still being determined, it is currently understood that the process of PTCA, besides opening the artherosclerotically obstructed artery, also injures resident coronary arterial smooth muscle cells (SMC). In response to this injury, adhering platelets, infiltrating macrophages, leukocytes, or the smooth muscle cells (SMC) themselves release cell derived growth factors with subsequent proliferation and migration of medial SMC through the internal elastic lamina to the area of the vessel intima. Further proliferation and hyperplasia of intimal SMC and, most significantly, production of large amounts of extracellular matrix over a period of 3-6 months, results in the filling in and narrowing of the vascular space sufficient to significantly obstruct coronary blood flow.

The treatment of restenosis requires additional, generally more invasive, procedures, including coronary artery bypass graft (CABG) in severe cases. Consequently, methods for preventing restenosis, or treating incipient forms, are being aggressively pursued. One possible method for preventing restenosis is the administration of anti-inflammatory compounds that block local invasion/activation of monocytes thus preventing the secretion of growth factors that may trigger SMC proliferation and migration. Other potentially anti-restenotic compounds include antiproliferative agents that can inhibit SMC proliferation, such as rapamycin and paclitaxel. Rapamycin is generally considered an immunosuppressant best known as an organ transplant rejection inhibitor. However, rapamycin is also used to treat severe yeast infections and certain forms of cancer. Paclitaxel, known by its trade name Taxol®, is used to treat a variety of cancers, most notably breast cancer.

However, anti-inflammatory and antiproliferative compounds can be toxic when administered systemically in anti-restenotic-effective amounts. Furthermore, the exact cellular functions that must be inhibited and the duration of inhibition needed to achieve prolonged vascular patency (greater than six months) are not presently known. Moreover, it is believed that each drug may require its own treatment duration and delivery rate. Therefore, in situ, or site-specific drug delivery using anti-restenotic coated stents has become the focus of intense clinical investigation. Recent human clinical studies on stent-based delivery of rapamycin and paclitaxel have demonstrated excellent short-term anti-restenotic effectiveness. Stents, however, have drawbacks due to the very high mechanical stresses, the need for an elaborate procedure for stent placement, and manufacturing concerns associated with expansion and contraction.

One of the most promising applications for targeted drug delivery using nanoparticles is in local application using interventional procedures such as catheters. Potential applications have focused on intra-arterial drug delivery to localize therapeutic agents in the arterial wall to inhibit restenosis (Labhasetwar, et al. *J Pharm Sci* 87, 1229-1234 (1998); Song, et al. *J Control Release* 54, 201-211 (1998)). Restenosis is the re-obstruction of an artery following interventional procedures such as balloon angioplasty or stenting as described above. Drug loaded nanoparticles are delivered to the arterial lumen via catheters and retained by virtue of their size, or they may be actively targeted to the arterial wall by non-specific interactions such as charged particles or particles that target the extracellular matrix. Surface-modified nanoparticles, engineered to display an overall positive charge facilitated adhesion to the negatively charged arterial wall and showed a 7 to 10-fold greater arterial localized drug levels compared to the unmodified nano-particles in different models. This was demonstrated to have efficacy in preventing coronary artery restenosis in dogs and pigs (Labhasetwar, et al. *J Pharm Sci* 87, 1229-1234 (1998)). Nanoparticles loaded with dexamethasone and passively retained in arteries showed reduction in neointimal formation after vascular injury (Guzman, et al. *Circulation* 94, 1441-1448 (1996)).

The microparticles (and/or nanoparticles) can be used in these procedures to prevent or reduce restenosis. Particles can be delivered at the time of bypass surgery, transplant surgery or angioplasty to prevent or minimize restenosis. The particles can be administered directly to the endothelial surface as a powder or suspension, during or after the angioplasty, or coated onto or as a component of a stent which is applied at the time of treatment. The particles can also be administered in conjunction with coronary artery bypass surgery. In this application, particles are prepared with appropriate agents such as anti-inflammatories or anti-proliferatives. These particles are made to adhere to the outside of the vessel graft by addition of adhesive ligands as described above. A similar approach can be used to add anti-inflammatory or immunosuppressant loaded particles to any transplanted organs or tissues.

In this embodiment, the drug to be delivered is preferably an anti-proliferative such as taxol, rapamycin, sirulimus, or other antibiotic inhibiting proliferation of smooth muscle cells, alone or in combination with an anti-inflammatory, such as the steroidal anti-inflammatory dexamethasone. The drug is encapsulated within and optionally also bound to the particles. The preferred size of the particles is less than one micron, more preferably approximately 100 nm in diameter. The polymer is preferably a polymer such as poly(lactic acid-co-glycolic acid) or polyhydroxyalkanoate which degrades over a period of weeks to months. Preferably the particles have a high density of an adhesive molecule on the surface such as one that adds charge for electrostatic adhesion, or one that binds to extracellular matrix or cellular material, or otherwise inert molecules such as an antibody to extracellular matrix component. Biotinylated particles have a higher level of adhesion to the tissue.

2. Treatment of Tumors

Tumors

BNPs and NNPs may be administered locally and/or systemically to treat tumors. Tumors to be treated may originate from different cancers, which include, but are not limited to, peritoneal cancer, vascular cancer such as multiple myeloma, adenocarcinomas and sarcomas, of bone, bladder, brain, breast, cervical, colo-rectal, esophageal, kidney, liver, lung, nasopharangeal cancer, pancreatic cancer, prostate cancer, skin cancer, stomach cancer, ovarian cancer, and uterine cancer.

Cancers to be Treated

Examples of cancers to be treated include, but are not limited to, Acute Lymphoblastic Leukemia (ALL), Acute Myeloid Leukemia (AML), Adrenocortical, Adrenal Cortex Cancer, AIDS-Related Cancers Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma, Carcinoid Tumor (Gastrointestinal), Carcinoid Tumors, Carcinoma of Unknown Primary, Cardiac (Heart) Tumors, Embryonal Tumors, Germ Cell Tumors, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal, Esthesioneuroblastoma, Ewing Sarcoma, Extracranial Germ Cell Tumor, Extragonadal Germ Cell Tumor, Eye Cancer Intraocular Melanoma, Retinoblastoma, Fallopian Tube Cancer, Fibrous Histiocytoma of Bone, Gallbladder Cancer, Gastric (Stomach) Cancer, Gastrointestinal Carcinoid Tumor, Gastrointestinal Stromal Tumors (GIST), Germ Cell Tumors Central Nervous System, Gestational Trophoblastic Disease, Gliomas, Hairy Cell Leukemia, Head and Neck Cancer, Heart Tumors, Hepatocellular (Liver) Cancer, Hodgkin Lymphoma, Hypopharyngeal Cancer, Intraocular Melanoma, Islet Cell Tumors, Pancreatic Neuroendocrine Tumors, Kaposi Sarcoma, Langerhans Cell Histiocytosis, Laryngeal Cancer and Papillomatosis, Leukemia, Lip and Oral Cavity Cancer, Liver Cancer (Primary), Lung Cancer, Lymphoma, Macroglobulinemia, Waldenström, Male Breast Cancer, Malignant Fibrous Histiocytoma of Bone and Osteosarcoma, Melanoma, Merkel Cell Carcinoma, Mesothelioma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma, Mycosis, Myelodysplastic Syndromes, Myelodysplastic/Myeloproliferative Neoplasms and Chronic Myeloproliferative Neoplasms, Myelogenous Leukemia, Chronic (CML), Myeloid Leukemia, Acute (AML), Nasal Cavity and Paranasal Sinus Cancer, Nasopharyngeal Cancer, Neuroblastoma, Non-Hodgkin Lymphoma, Non-Small Cell Lung Cancer, Oral Cancer, Lip and Oral Cavity Cancer and Oropharyngeal Cancer, Osteosarcoma and Malignant Fibrous Histiocytoma of Bone, Ovarian Cancer, Pancreatic Cancer and Pancreatic Neuroendocrine Tumors (Islet Cell Tumors), Papillomatosis, Paraganglioma, Paraganglioma, Paranasal Sinus and Nasal Cavity Cancer, Parathyroid Cancer, Penile Cancer, Pharyngeal Cancer, Pheochromocytoma, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Renal Cell (Kidney) Cancer, Retinoblastoma, Rhabdomyosarcoma, Salivary Gland Cancer, Salivary Gland Tumors, Sarcoma Ewing Sarcoma, Kaposi Sarcoma, Osteosarcoma, Rhabdomyosarcoma, Uterine Sarcoma, Vascular Tumors, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, T-Cell Lymphoma, Testicular Cancer, Throat Cancer, Thymoma and Thymic Carcinoma, Thyroid Cancer, Thyroid Tumors, Transitional Cell Cancer of the Renal Pelvis and Ureter, Unknown Primary, Carcinoma, Ureter and Renal Pelvis, Transitional Cell Cancer, Urethral Cancer, Uterine Cancer, Endometrial and Uterine Sarcoma, Vaginal Cancer, Vascular Tumors, Vulvar Cancer, Waldenström Macroglobulinemia, and Wilms Tumor.

Peritoneal and Ovarian Cancers

Peritoneal cancer develops in the peritoneum, a thin, delicate sheet that lines the inside wall of the abdomen and covers the uterus and extends over the bladder and rectum. The peritoneum is made of epithelial cells. By producing a lubricating fluid, the peritoneum helps the organs to move smoothly inside the abdomen. Peritoneal cancer looks and behaves like ovarian cancer, but the ovaries are minimally involved. Women who develop ovarian cancer after having had their ovaries previously removed likely have peritoneal cancer. Endometriosis may also proliferate into the peritoneum. Although technically not cancer, it is an abnormal overproliferation of cells that can cause sterility, pain, adhesions and other problems. It may also be treated as in the case of peritoneal and ovarian cancers.

The surface of the ovaries is made from epithelial cells. Therefore, peritoneal cancer and the most common type of ovarian cancer, epithelial cancer, produce some of the same symptoms and are often treated in the same way. Women who are at an increased risk of developing ovarian cancer, particularly due to the BRCA1 and BRCA2 genetic mutations, also are at increased risk for peritoneum cancer.

Uterine Cancers

Uterine cancer can start in different parts of the uterus. Most uterine cancers start in the endometrium (the inner lining of the uterus), and is referred to as endometrial cancer. Most endometrial cancers are adenocarcinomas (cancers that begin in cells that make mucus and other fluids). Uterine sarcoma is an uncommon form of uterine cancer that forms in the muscle and tissue that support the uterus.

Treating Tumors

The NNPs and BNPs containing therapeutic, diagnostic, prophylactic agents, and/or neutraceuticals, may be administered locally or systemically to treat disorders, or deliver nutrients.

Local administration includes parenteral, buccal, or enteral administration to a specific organ or site in a subject. Systemic administration includes intravenous administration. For example, BNPs may be administered locally or regionally by injection into a desired site or tissue, blood vessel or lymph notes leading into a tissue or region in the subject. The BNPs adhere to the surrounding proteins/cells/tissue and provide prolonged release of agents contained therein. NNPs may be administered systemically to provide prolonged release of agents contained therein.

Passive delivery of BNPs and NNPs may be used to target tumors. Aggressive tumors inherently develop leaky vasculature with 100 to 800 nm pores due to rapid formation of vessels that must serve the fast-growing tumor. This defect in vasculature coupled with poor lymphatic drainage serves to enhance the permeation and retention of nanoparticles within the tumor region. This is often called the EPR effect. This phenomenon is a form of 'passive targeting'. The basis for increased tumor specificity is the differential accumulation of drug-loaded nanoparticles in tumor tissue versus normal cells, which results from particle size rather than binding. Normal tissues contain capillaries with tight junctions that are less permeable to nanosized particles. Passive targeting can therefore result in increases in drug concentrations in solid tumors of several-fold relative to those obtained with free drugs.

Passive delivery may also be directed to lymphoid organs of the mammalian immune system, such as lymphatic vessels and spleen. These organs are finely structured and specialized in eliminating invaders that have gained entry to tissue fluids. Nanoparticles may easily penetrate into lymphatic vessels taking advantage of the thin walls and fenestrated architecture of lymphatic microvessels. Passive targeting to the spleen is via a process of filtration. Indeed the spleen filters the blood of foreign particles larger than 200 nm. This function facilitates splenic targeting with nanoparticles encapsulating drug for effective treatments against several hematological diseases.

Both liposomal and solid nanoparticles formulations have received clinical approval for delivery of anticancer drugs. Liposomal formulations include those of doxorubicin (DOXIL®1/CAELYX®1 AND MYOCET®1) and daunorubicin (DAUNOSOME®1). The mechanism of drug release from liposomes is not clear, but is thought to depend on diffusion of the drug from the carrier into the tumor interstitium. This is followed by subsequent uptake of the released drug by tumor cells. The mechanism of release is still poorly understood, which hinders advanced applications involving the addition of active ligands for cellular targeting in vivo. Recently, the FDA approved ABRAXANE®, an albumin-bound paclitaxel nanoparticles formulation as an injectable suspension for the treatment of metastatic breast cancer. In addition, other solid nanoparticle-based cancer therapies have been approved for clinical trials, for example a Phase 1 clinical trial has been approved that will evaluate the safety of hepatic arterial infusion of REXIN-G™ (a targeted nanoparticle vector system with a proprietary mutant cell-cycle control gene, i.e. anti-cancer gene) as an intervention for colorectal cancer.

The particles described herein should be efficacious in the treatment of tumors, especially those where targeting is beneficial and delivery of high doses of chemotherapeutic desirable. An important feature of targeted particle delivery is the ability to simultaneously carry a high density of drug while displaying ligands on the surface of the particle. It is well known that other drug carrier systems, such as immunotoxins or drug-immunoconjugate, which are made by tethering drug molecules to antibodies or synthetic polymers, usually deliver less than 10 drug molecules per carrier to target cells. Targeted high density nanoparticles on the other hand can deliver thousands of drug molecules on the surface, and millions of molecules in their interior.

One important target is E-selectin, which is involved in the arrest of circulating immune system cells and is differentially upregulated with inflammatory and immune processes and should be useful to enhance delivery of therapeutic agents to the vasculature including tumor blood vessels through selective targeting. A second important class of targets is receptors involved in the uptake of vitamin B12, folic acid, biotin and thiamine. These are differentially overexpressed on the surface of cancer cells creating a possible target for several types of cancer, including ovarian, breast, lung, renal and colorectal cancers. One of the most promising strategies for enhancing active immunotherapy and inducing potent vaccination is targeting of antigen-loaded nanoparticles to antigen-presenting cells such as dendritic cells (DCs). Nanoparticles incorporating toll-like receptors (TLRs) in biodegradable PLGA have shown efficient delivery of antigen to DC and potent activation of the T cell immune response.

The overall strength of nanoparticles binding to a target is a function of both affinity of the ligand-target interaction and the number of targeting ligands presented on the particle surface. Nanoparticles produced by the present techniques have many thousands of ligands on their surface. This is a particularly useful feature for ligands that in their monomer form have a weak affinity to their target receptors, such as single chain variable fragments (scFv), which in most cases must be reengineered into multimers to increase their avidity of interaction to target cells or peptide/Major histocompatibility complex (peptide/MHC), which have weak affinity to target T cell receptors. For example, multivalency increases the avidity of interaction of peptide/MHC to the T cell up to 100 fold facilitating enhanced interactions and effective drug delivery to target antigen-specific T cells.

3. Macular Degeneration

Macular degeneration (MD) is a chronic eye disease that occurs when tissue in the macula, the part of the retina that is responsible for central vision, deteriorates. Degeneration of the macula causes blurred central vision or a blind spot in the center of your visual field. Macular degeneration occurs most often in people over 60 years old, in which case it is called Age-Related Macular Degeneration (ARMD) or (AMD). AMD is the leading cause of blindness in the United States and many European countries. About 85-90% of AMD cases are the dry, atrophic, or nonexudative form, in which yellowish spots of fatty deposits called drusen appear on the macula. The remaining AMD cases are the wet form, so called because of leakage into the retina from newly forming blood vessels in the choroid, a part of the eye behind the retina. Normally, blood vessels in the choroid bring nutrients to and carry waste products away from the retina. Sometimes the fine blood vessels in the choroid underlying the macula begin to proliferate, a process called choroidal neovascularization (CNV). When those blood vessels proliferate, they leak, causing damage to cells in the macula often leading to the death of such cells. The neovascular "wet" form of AMD is responsible for most (90%) of the severe loss of vision. There is no cure available for "wet" or "dry" AMD.

The exact causes of AMD are not known, however, contributing factors have been identified. Factors that contribute to AMD include reactive oxidants which cause oxidative damage to the cells of the retina and the macula, high serum low density cholesterol lipoprotein (LDL) concentration, and neovascularization of the choroid tissue underlying the photoreceptor cells in the macula.

Treatments for wet AMD include photocoagulation therapy, photodynamic therapy, and transpupillary thermotherapy. AMD treatment with transpupillary thermotherapy (TTT) photocoagulation is a method of delivering heat to the back of the patient's eye using an 810 nm infrared laser, which results in closure of choroidal vessels. AMD treatment with photocoagulation therapy involves a laser aimed at leakage points of neovascularizations behind the retina to prevent leakage of the blood vessel. Photodynamic therapy (PDT) employs the photoreactivity of a molecule of the porphyrin type, called verteporphin or Visudyne, which can be performed on leaky subfoveal or juxtafoveal neovascularizations. MACUGEN® is an FDA approved drug that inhibits abnormal blood vessel growth by attacking a protein that causes abnormal blood vessel growth.

Other potential treatments for "wet" AMD that are under investigation include angiogenesis inhibitors, such as anti-VEGF antibody, and anti-VEGF aptamer (NX-1838), integrin antagonists to inhibit angiogenesis has also been proposed, and PKC412, an inhibitor of protein kinase C. Cytochalasin E (Cyto E), a natural product of a fungal species that inhibits the growth of new blood vessels is also being investigated to determine if it will block growth of abnormal blood vessels in humans. The role of hormone replacement therapy is being investigated for treatment of AMD in women.

There are no treatments available to reverse "dry" AMD. Treatments shown to inhibit progression of AMD include supplements containing antioxidants. The use of a gentle "sub-threshold" diode laser treatment that minimizes damage to the retina is being investigated for treatment of "dry" AMD. Another potential treatment for AMD includes rheopheresis, which is a form of therapeutic blood filtration that removes "vascular risk factor" including LDL cholesterol, fibrinogen, and lipoprotein A. Rheopheresis has not yet been FDA-approved, but is available in Canada and Europe. Other treatments for AMD under investigation include culturing and transplantation of cells of the Retinal Pigment Epithelium (RPE), metalloproteinase modulators, inhibitors of A2E, a vitamin A derivative, which accumulates in the human eye with age, and carotenoids, zeaxanthin and lutein.

There have been a number of studies indicating that macular degeneration is caused by, or associated with, a defect in complement factor H (Haines, et al. Science. 2005 308(5720):419-21; Edwards, et al. Science. 2005 15; 308 (5720):421-4; Klein, et al. Science. 2005; 308(5720):385-9). This leads to a method of treatment or prevention of the macular degeneration through administration of one of the known complement inhibitors, such as antibodies (antibody fragments, recombinant antibodies, single chain antibodies, humanized and chimeric antibodies) to C3b or a component thereof. An example is PEXELIZUMAB® (Alexion Pharmaceuticals, Inc., Cheshire, Conn., USA), a humanized, monoclonal, single-chain antibody fragment that inhibits C5, thereby blocking its cleavage into active forms. A potential inhibitor is relatively small, broad-acting C inhibitory protein (termed OmCI), described by Nunn, et al. J Immunol. 2005 15; 174(4):2084-91.

Ocular delivery of drug-loaded, sustained-release and optionally targeted nanoparticles by intravitreal administration is a promising route for eye disease because it eliminates the need for multiple injections of drug into the eye. Coupled with the problem of retention of adequate concentrations of therapeutic agent in the pre-corneal area (Mainardes, et al. Curr. Drug Targets 6, 363-371 (2005)), biodegradable nanoparticles delivered intravitreally have demonstrated localization in the retinal pigment epithelium (Bourges, et al. Invest. Ophthalmol. Vis Sci 44, 3562-3569 (2003)) and greater therapeutic efficacy in ocular disease such as autoimmune uveoretinitis (de Kozak, et al. Eur. J. Immunol. 34, 3702-3712 (2004)).

In this embodiment, the drug is encapsulated with, and optionally also bound to the particles. The preferred size of the particles is approximately 100 nm in diameter. The polymer is preferably a polymer such as poly(lactic acid-co-glycolic acid) or polyhydroxyalkanoate which degrades over a period of weeks to months.

In the preferred embodiment, degradable particles less than one micron in diameter, preferably about 100 nm in diameter, are distributed within the eye by subretinal injection or intravitreally injection, where they degrade over a period of from several weeks to several months. In the most preferred case, the particles have a high density of adhesive molecules to retinal epithelial cells. It should be noted that the particles may also be larger, in the microparticle size range.

B. Tissue Engineering Matrices and Wound Healing Dressings

The particles can be dispersed on or within a tissue engineering matrix for delivery of growth factors or modulatory compounds, as demonstrated in the examples. Many types of materials are known for use in tissue engineering, including materials formed of synthetic polymer, decellularized matrix, collagen, and decellularized tissue. These can be in the form of fibrous matrices or materials such as those used in bone repair or replacement, which consist primarily of materials such as hydroxyapatite. In another embodiment, nanoparticles delivering molecules which are used to enhance wound healing such as antibiotics, growth, angiogenesis stimulating molecules, and other types of drugs, can be applied to wound healing matrices, implants, dressings, bone cements, and other devices which are applied to the site of injury. Preferred antibiotics include vancomycin, ciprofloxacin and anti-infective peptides such as the defensin molecules. In addition, re-vascularization of these grafts can be a problem, hence VEGF, FGF and PDGF could be included in the particles.

The advantage of these particles is that they adhere to the implanted/applied material, where they are retained at the site of injury to provide sustained treatment. Mixtures releasing different amounts or different drugs at different times are particularly advantageous for treatment of wounds such as diabetic wound ulcers. Ligands can be selected to enhance the particles being retained at the site, by binding to extracellular matrix or through non-specific electrostatic binding. In addition, other ligands can be selected to enhance the interaction of particles or matrix with cells that are either added to the material prior to implantation or migrate into the material after implantation.

The present invention will be further understood by reference to the following non-limiting examples.

EXAMPLES

Example 1. Synthesis of Hyperbranched Polyglycerol

Materials and Methods for Making Polymers

Polylactic acid (Mw=20.2 kDa, Mn=12.4 kDa) was obtained from Lactel.

$H_2N$-PEG(5000)-$OCH_3$ was obtained from Laysan.

Anhydrous dimethylformide, dichloromethane, diisopropylcarboimide, dimethylaminopyridie, potassium methoxide, camptothecin, polyvinyl alcohol, paraformaldehyde, TWEEN® 80, and 1,1,1-trihydroxymethyl propane were obtained from the Sigma-Aldrich.

Anhydrous dry ether, methanol, acetonitrile and dimethylsulfoxide were obtained from J. T. Baker.

1,1'-Dioctadecyl-3,3,3',3'-Tetramethylindodicarbocyanine,4 Chlorobenzenesulfonate Salt (DiD) and DAPI stain were obtained from INVITROGEN®.

Hyperbranched polyglycerol (HPG) was synthesized by anionic polymerization. Briefly, 4.6 mmol 1,1,1-trihydroxypropane (THP) was added into an argon protected flask in a 95° C. oil bath and 1.5 mmol $KOCH_3$ was added. The system was hooked up to a vacuum pump and left under vacuum for 30 min. The system was refilled with argon and 25 ml glycidol was added by a syringe pump over 12 hours. The HPG was dissolved in methanol and precipitated by addition of acetone. HPG was purified 2-3 times with methanol/acetone precipitation. To further remove the low molecular weight HPG, 2-5 ml HPG was placed in a 10 ml dialysis tube (0.5-1 k cut-off) and dialyzed against deionized (DI) water. The water was replaced two times every 12 hours. HPG was precipitated with acetone and then dried under vacuum at 80° C. for 12 h.

Example 2. Synthesis of PLA-HPG and PLA-PEG Copolymers

PLA (5 g) and 2.15 g HPG were dissolved in dimethyl formamide (DMF) and dried over molecular sieves overnight. 0.06 ml diisopropylcarboimide (DIC) and 10 mg 4-(N,N-dimethylamino)pyridine (DMAP) were added and the reaction proceeded for 5 days at room temperature under stirring. The product was precipitated by pouring the reaction into cold diethyl ether (ether) and collecting the precipitate by centrifugation. The product was redissolved in dichloromethane (DCM) and precipitated again with a cold mixture of ether and methanol. The product was washed with a cold mixture of ether and methanol. The polymer was dried under vacuum for 2 days.

To synthesize PLA-PEG, 2.6 g PLA and 1.0 g MPEG-$NH_2$ were dissolved in DMF and dried over molecular sieves overnight. 0.038 ml DIC was added and the reaction proceeded for 2 days at room temperature under stirring. The product was precipitated by pouring the reaction into cold ether and collecting the precipitate by centrifugation. The product was redissolved in DCM and precipitated again with cold ether, washed with a cold mixture of ether and methanol and dried under vacuum for 2 days.

Example 3. Fabrication of Nanoparticles (NPs)

Fifty mg of PLA-HPG copolymer dissolved in 1.5-3.0 ml of ethyl acetate/dimethyl sulfoxide (DMSO) (4:1) was added to 4 ml DI water under vortexing and subjected to probe sonication for 3 cycles at 10 sec each. The resulting emulsion was diluted in 20 ml DI water under stirring. It was stirred for at least 5 hours or attached to a ratovapor to evaporate the ethyl acetate and then applied to an AMICO® ultra centrifuge filtration unit (100 k cut-off). The NPs were washed by filtration 2 times then suspended in a 10% sucrose solution. The NPs were kept frozen at −20° C.

The PLA-PEG NPs were made using a single emulsion technique. 50 mg PLA-PEG copolymer dissolved in 1.5-3.0 ml ethyl acetate/DMSO (4:1) was added to 4 ml DI water with 2.5% PVA under vortexing and subjected to probe sonication for 3 cycles of 10 sec each. The resulting emulsion was diluted in 20 ml DI water with 0.1% TWEEN® 80 with stirring. The emulsion was stirred for at least 5 hours or attached to a ratovapor to evaporate the ethyl acetate and then the solution was applied to an Amico ultra centrifuge filtration unit (100 k cut-off). The NPs were washed by filtration for 2 times then suspended in a 10% sucrose solution.

$^1$H NMR spectra for HPG and PLA-HPG block-copolymer were recorded on a 400 MHz Agilent instrument using DMSO-d6 as solvent. Inverse gated $^{13}$C NMR spectra for HPG were recorded on a 600 MHz Agilent instrument with methanol-d4 as solvent.

The $\overline{DP_n}$ (number-average degree of polymerization) for HPG was calculated according to the inverse gated $^{13}$C NMR spectra for HPG with the following equation:

$$\overline{DP_n} = \frac{(T + L_{13} + L_{14} + D)}{(T - D)} f_c$$

The functionality of the core molecule (TMP), $f_c$, is 3.
The Mn of HPG is calculated with the following equation:

Mn=Molecular weight of glycidol×$\overline{DP_n}$ of HPG+ molecular weight of TMP.

Both particles have a biodegradable PLA core, which can be used to load hydrophobic agents, and a hydrophilic shell of HPG or PEG. HPG was made by anionic polymerization and characterized by $^1$H NMR and $^{13}$C NMR. PLA-HPG copolymer was synthesized by esterification and the conjugation of PLA-HPG was confirmed by $^1$H NMR. The weight percentage of HPG in PLA-HPG was about 29% as calculated from the NMR results.

PLA-HPG NPs were made from a single emulsion as described above. PLA-PEG copolymer was synthesized by the conjugation of PLA-COOH with amine terminated mPEG and also characterized with $^1$H NMR. The weight percentage of PEG was about 26% as calculated from the NMR results.

Example 4. Characterization of Nanoparticles (NPs) by Transmission Electron Microscopy (TEM)

Materials and Methods

The NPs were characterized with TEM. A drop of nanoparticle suspension was applied on the top of carbon coated copper grids and most of the droplet was removed with a piece of filter paper. The thin layer of NPs suspension was dried for 5-10 min and then a droplet of uranyl acetate was applied. Most of the droplet was removed with a filter paper and left to dry for 5 min. The sample was mounted for imaging with TEM. The size distribution of NPs was analyzed in Image J. The hydrodynamic size of NPs was determined by dynamic laser scattering (DLS). NPs suspension was diluted with DI water to 0.05 mg/ml and 1 ml was loaded into the cell for detection.

To determine the concentration of the dye in NPs, 990 µL DMSO was added to 10 µL NPs in aqueous solution. The solution was vortexed and left in the dark for 10 min. The concentration of the dye was quantified with a plate reader by fluorescence of the DiD dye at 670 nm with an excitation wavelength at 644 nm.

The amount of CPT encapsulated in NPs was determined by fluorescence of CPT at 428 nm with an excitation wavelength at 370 nm. One volume of NP suspension was diluted in acidified DMSO (1N HCl:DMSO=1:100, volume ratio) at least 10 fold. The fluorescence of CPT was measured and the amount of CPT was determined by comparing to a standard curve.

Results

Figure 3:
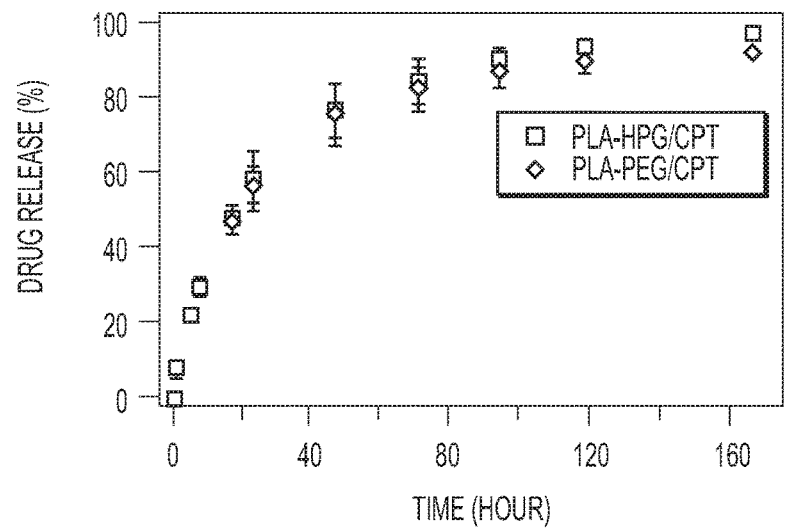
FIG. 3 is a graph showing drug release (%) as a function of time (hours) for PLA-HPG/camptothecin (CPT) and PLA-PEG/CPT nanoparticles.

Transmission electronic microscopy (TEM) confirmed the spherical shape of the PLA-HPG and PLA-PEG NPs (FIGS. 2A, 2B, 2C and 2D). The hydrodynamic diameter of NPs was 100 nm as measured by dynamic light scattering (DLS) (Table 1). In this study, CPT loading of both PLA-HPG and PLA-PEG NPs is 5%. The NPs loaded with CPT have a larger fraction in the upper size range and larger size of hydrodynamic diameters by TEM imaging. When the NPs were loaded with CPT and incubated in buffered water, the agent was released over a period of about 1 week (FIG. 3). Both NPs showed similar patterns of CPT release. After 24 hr of incubation, over half of the CPT was released from PLA-HPG (59%) and PLA-PEG (56%) NPs. The rest of the encapsulated drug was slowly released over a period of 1 week. PLA-HPG/CPT NPs remain suspended in solution significantly longer than PLA-PEG/CPT NPs, indicating greater stability of PLA-HPG/CPT NPs in suspension.

TABLE 1

Average diameter of PLA-HPG nanoparticles, PLA-PEG nanoparticles, PLA-HPG/camptothecin (CPT) nanoparticles, and PLA-PEG/CPT nanoparticles.

| NPs | Diameter (nm) |
| --- | --- |
| PLA-HPG | 102.1 ± 3.1 |
| PLA-PEG | 103.3 ± 1.0 |
| PLA-HPG/CPT | 158.4 ± 8.8 |
| PLA-PEG/CPT | 142.3 ± 5.2 |

Example 5. Evaluation of NPs In Vitro

Materials and Methods

Donkey normal serum and Rabbit-anti-CD31 antibody were obtained from ABCAM® and the Donkey-anti-rabbit secondary antibody tagged with Alexa488 fluorophore was obtained from INVITROGEN®.

Cell titer blue was obtained from PROMEGA®.

Phorbol 12-myristate 13-acetate (PMA) was from ABCAM®.

Cell Lines

Lewis lung carcinoma (LLC) cell line was obtained from the American Type Culture Collection (ATCC) (Manassas, Va.). LLC cells were maintained in Dulbecco's Modified Eagle Medium (DMEM) supplemented with 10% fetal bovine serum (FBS) and 1% penicillin-streptomycin at 37° C. under 5% CO2 humidified atmosphere. U937 was maintained in RPMI1640 supplemented with 10% FBS. Differentiation of U937 to macrophage was induced by PMA (50 ng/ml).

A suspension containing 3 mg NPs in a dialysis tube (10K cut-off) was dialyzed against 40 ml PBS. At each time point, 970 µL solution was removed and the rest was replaced with 40 ml fresh PBS. To quantify the CPT in the 970 µL dialyte, 30 µL of quantification fluid (DMSO:10% SDS:1 N HCL=1:1:1, volume ratio) was added and the CPT concentration was quantified at EX/EM 370/428 nm with a plate reader.

Microdialysis tubes were filled with 100 µL of NPs loaded with 1,1'-dioctadecyl-3,3,3',3'-tetramethylindodicarbocyanine, 4-chlorobenzenesulfonate Salt (DiD) and placed on a floater in a large beaker with 4 L PBS at 37° C. Tubes were removed in triplicates at different time points. The PBS was changed every 12 hours. The dye left in the dialysis tube was quantified by fluorescence.

180 µL of LLC cells was plated in each well of a 96 well plate at a density of 5,000/well and left in a 37° C. incubator overnight. 20 µl of free CPT or NPs in medium were added to each well. The cells were incubated for 72 h and cell viability was quantified with Cell Titer Blue.

The surface properties of PLA-HPG NPs were evaluated in vitro by measuring cell uptake by macrophages. Both PLA-HPG NPs and PLA-PEG NPs showed significantly lower cell uptake compared to that of the plain PLA NPs. PLA-HPG/CPT NPs were evaluated for cell toxicity to LLC cells. The controls chosen for this study were PLA-PEG/CPT NPs and free CPT.

Results

Figure 4A:
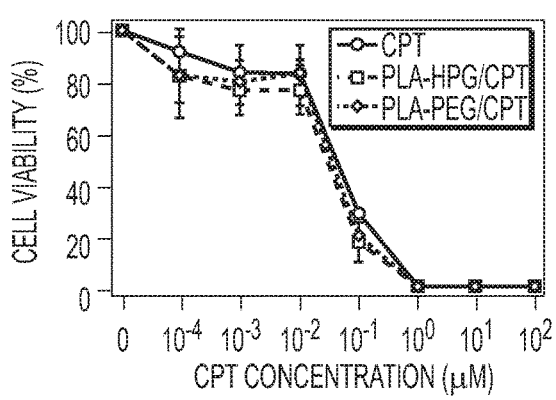
FIG. 4A is a graph showing cell viability (%) as a function of camptothecin (CPT) concentration (μM) for free CPT, PLA-HPG/CPT nanoparticles, and PLA-PEG/CPT nanoparticles.
Figure 4B:
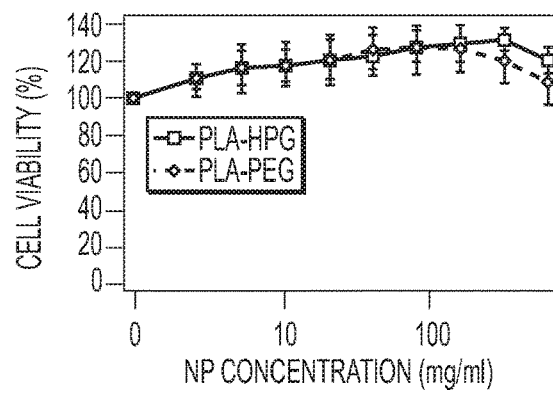
FIG. 4B is a graph showing cell viability (%) as a function of nanoparticle (NP) concentration (mg/ml) for PLA-HPG nanoparticles and PLA-PEG nanoparticles

Both NP formulations showed the significantly improved cytotoxicity profile (FIG. 4A). To show that this toxicity is due to the CPT, and not the polymers, the effect of blank NPs on LLC cells was examined: both blank NP formulations showed no toxicity (FIG. 4B).

Example 6. Evaluation of NPs in Blood Circulation and Biodistribution

Materials and Methods

All animal care and studies were approved by Yale's Institutional Animal Care and Use Committee (IACUC). Both NPs were loaded with 0.2% fluorescence dye (DiD from INVITROGEN®). 14 C57BL/6 mice (n=7 per group) received tail vein injection of 150 µL DiD loaded NPs (3 mg/ml in PBS solution). At 5 min, 15 min, 30 min, 1 hr, 2 hr, 4 hr, 8 hr, 24 hr, 48 hr and 72 hr 10-20 µL blood were collected from each mouse by tail snipping. The blood was lyophilized. To quantify the fluorescence in the blood, 100 µl of DMSO and 1 ml of acetonitrile were added and homogenized with a homogenizer. The homogenized solution was spun on a benchtop centrifuge at 13,000 RPM and then 0.8 ml supernatant was removed and added to an eppendorf tube. All the acetonitrile was evaporated with a SpeedVac and the dye in the DMSO was quantified at Ex/Em 644/670 nm with a plate reader.

The biodistribution of DiD-loaded NPs was evaluated in Balb/C mice bearing subcutaneous LLC tumors. LLC cells ($1\times10^6$ cells, 0.1 ml) were injected subcutaneously into Balb/C female mice (6 week old, Charles River Laboratories), and nanoparticle administration was started after 7 days, a time when the average tumor volume reached approximately 100 $mm^3$.

Thirty mice were divided into four groups with 7-8 animals in each group. The average size and size variation of the tumors in all groups were comparable. 150 µL DiD loaded NPs (3 mg/ml in PBS solution) were administrated intravenously through tail vein. At 12 h and 24 h, the mice were euthanized and blood was collected with cardiac puncture. After perfusion through the left ventricle with PBS, the organs were collected. The blood and organs were lyophilized.

To quantify the dye in the organs and tumors except lung and spleen, 1 ml DMSO was added and homogenized. The homogenized solution was spun on a benchtop centrifuge at 13,000 RPM and then 0.1 ml of the supernatant was added to a 96 well plate and the dye in the DMSO was quantified at Ex/Em 644/670 nm with a plate reader.

To quantify the dye in lung and spleen, 1 ml of DMSO was added and homogenized. The homogenized solution was spun on a benchtop centrifuge at 13,000 RPM and then 0.1 ml supernatant was added to 1 ml acetonitrile. The solution was spun on a benchtop centrifuge at 13,000 RPM and then 0.8 ml supernatant was removed and added to an eppendorf tube.

All the acetonitrile was evaporated with a SpeedVac and the dye was quantified in the DMSO at Ex/Ex 644/670 nm with a plate reader. One-way analysis of variance (ANOVA) was performed to determine the statistical significance of the dose distribution in organs and blood, $p<0.05$ was considered to be significant.

To demonstrate the effect of the HPG coating on the nanoparticle surface in vivo, NPs were injected intravenously and blood analyzed periodically for the presence of particles. To permit quantification of NP concentration in the blood, NPs were loaded with 0.2% 1,1'-Dioctadecyl-3,3,3', 3'-tetramethylindo-dicarbocyanine, 4-Chlorobenzenesulfonate Salt (DiD). DiD is a hydrophobic dye which has been widely used as a marker for NPs.

Results

Figure 5:
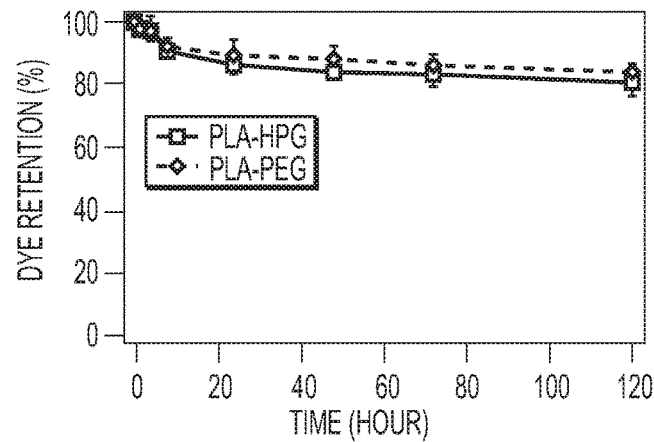
FIG. 5 is a graph showing dye retention (%) of PLA-HPG and PLA-PEG nanoparticles as a function of incubation time in PBS.
Figure 6A:
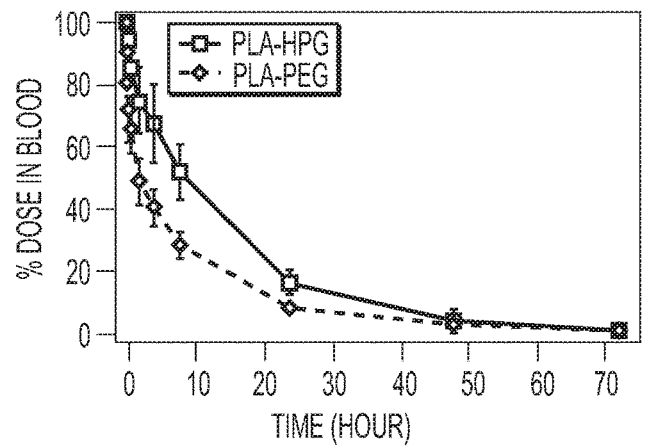
FIG. 6A is a graph showing the dose in blood (%) as a function of time (hours) for PLA-HPG and PLA-PEG nanoparticles.
Figure 6B:
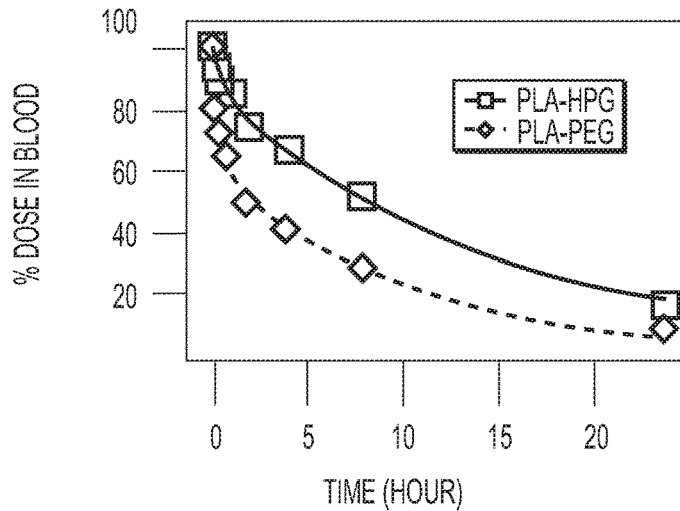
FIG. 6B is a graph showing the dose in blood (%) as a function of time (hours) for PLA-HPG and PLA-PEG nanoparticles.

DiD-loaded NPs release a minimal amount of dye (approximately 20%) over 5 days of continuous incubation in PBS (FIG. 5). Both PLA-HPG and PLA-PEG NPs were loaded with equivalent amounts of DiD. Comparing the PLA-PEG NPs, the PLA-HPG showed a longer time of circulation after administration (FIG. 6A). The elimination half-life of PLA-HPG NPs (10.3 hr) was significantly longer than PLA-PEG NPs (6.8 hr): half-lives were determined by fitting with a two-compartment model (FIG. 6B). A negligible amount of either NP was found in circulation 2 days after administration.

Figure 6C:
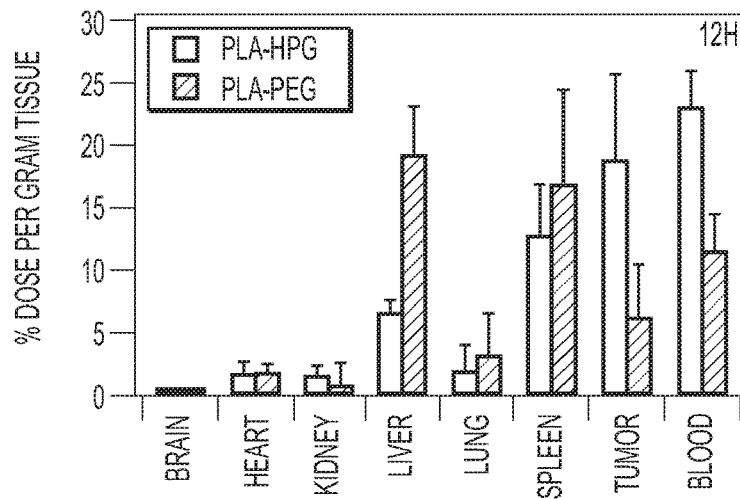
FIGS. 6C and 6D are graphs showing the dose of PLA-HPG or PLA-PEG NPs per gram tissue (%) as a function of tissue at 12 hours (FIG. 6C) and 24 hours (FIG. 6D).
Figure 6D:
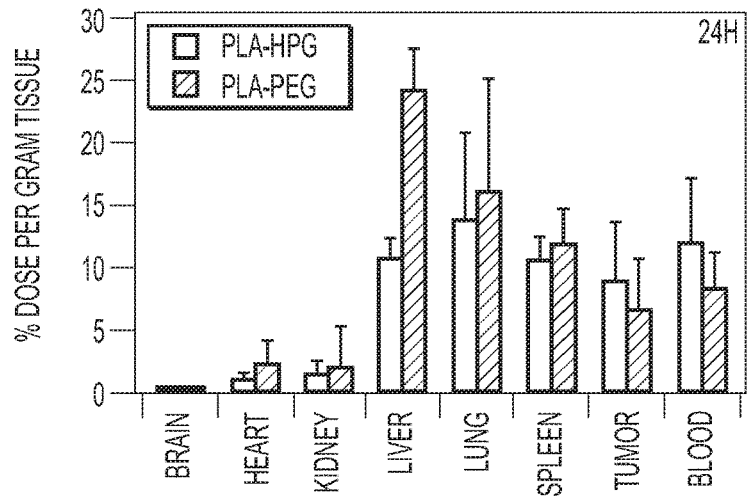
Figure 6E:
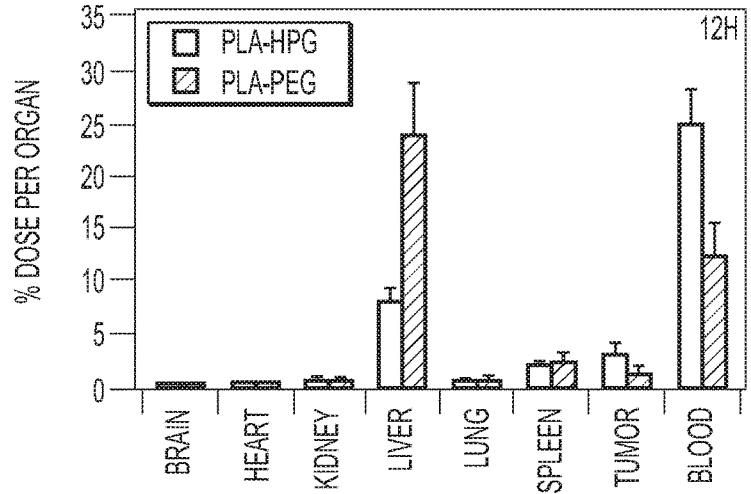
FIGS. 6E and 6F are graphs showing the dose of PLA-HPG or PLA-PEG NPs per organ (%) as a function of organ at 12 hours (FIG. 6E) and 24 hours (FIG. 6F).
Figure 6F:
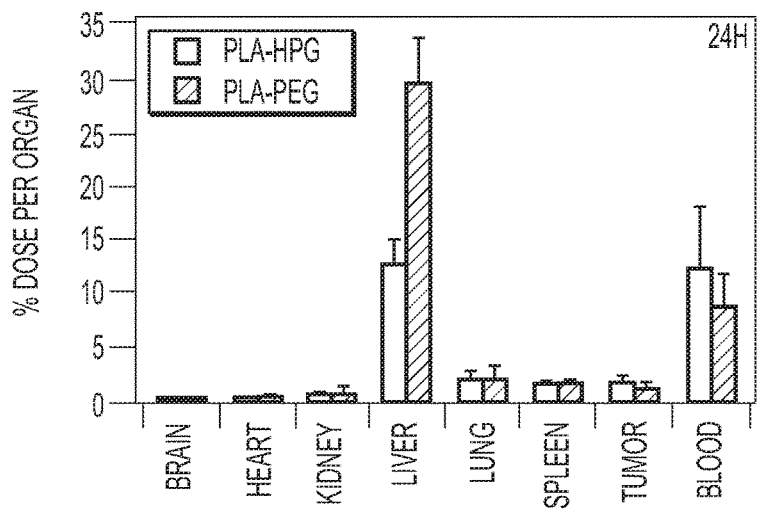

To further demonstrate the effect of the PLA-HPG NPs, the biodistribution of the NPs in mice with subcutaneous LLC tumors was studied. Fluorescence measured in tissues was normalized to percent dose/gram tissue (FIGS. 6C and 6D). There was no significant difference in the accumulation of either PLA-HPG or PLA-PEG NPs in brain, heart, kidney, lung and spleen at 12 and 24 hr. However, compared to the PLA-PEG NPs, the PLA-HPG NPs were present in significantly higher concentration in the tumor and blood, but significantly lower concentration in the liver at 12 hr after injection. These differences persisted at 24 hr (although were not statistically significant in blood and tumor). To better understand the impact of overall NP distribution the total mass of NPs in each organ was calculated, tumor and the whole blood by multiplying the percent dose/gram tissue with tissue weight (FIGS. 6E and 6F). The majority of NPs were in either liver or blood at both time points. At 12 hours, two times as many PLA-HPG NPs were present as PLA-PEG NPs in whole blood and one third as many PLA-HPG NPs, compared to PLA-PEG NPs, were present in the liver. At 24 hours, PLA-HPG accumulation in the liver was half of PLA-PEG though both NPs were present in similar quantities in blood.

Example 7. Evaluation of Tumors Treated with NPs

Materials and Methods

Nine balb/c mice (n=3 per group) bearing LLC tumors underwent tail vein injection of 150 µL NPs (3 mg/ml in PBS solution) or PBS control. At 12 hrs, animals were sacrificed. After perfusion through the left ventricle with PBS the tumors were dissected and frozen in OCT. The tumors were sectioned at 10 µm thickness and immobilized onto SUPERFROST® Microscope slides. The tumor sections were fixed in 4% paraformaldehyde in PBS for 30 min and then washed with TBS (20 mM Tris PLA-HPG 7.6, 140 mM NaCl) 3 times 5 min each. Samples were blocked in TBS with 1% BSA and 5% donkey normal serum for 1 h and then incubated with Rabbit-anti-CD31 antibody (1:50 dilution in TBS with 1% BSA and 5% donkey normal serum). The sections were washed with TBS 3 times 5 min each and then incubated with Donkey-anti-rabbit secondary antibody tagged with Alexa488 fluorophore (INVITROGEN®, 1:200 dilution in TBS with 1% BSA and 5% donkey normal serum) for 1 hour and washed again with TBS 3 times, 5 min each. Several drops of DAPI were placed on each slide and the slides were covered with a coverslip. Images were taken with a Zeiss fluorescence microscope.

Results

To visualize the penetration of NPs in tumors, immunohistochemistry on cryo-sections of tumors that were treated with PLA-HPG NPs was performed. NPs were found beyond the boundaries of blood vessel lumens, indicating that the NPs penetrated deep into the tumor tissue after extravasating through the tumor vascular after intravenous administration.

Example 8. Treatment of Tumors with NPs

Materials and Methods

Forty C57BL/6 mice (6 weeks old, Charles River Laboratories) were subcutaneously injected $1\times10^6$ LLC cells. After 7 days, a time when the average tumor volume reached approximately 100 $mm^3$, 40 mice were equally divided into 5 groups with comparable average size distribution of tumors. After grouping the mice, drug treatments were started immediately with PBS control, blank PLA-HPG NPs control and 3 CPT formulations: 1) PBS (PLA-HPG=7.4); 2) blank PLA-HPG NPs in PBS; 3) CPT DMSO solution (2.5 mg/ml, DMSO:PBS10x=9:1 volume ratio); 4) PLA-PEG/CPT NPs in PBS; 5) PLA-HPG/CPT NPs in PBS. Treatments were administrated 2 times at 7 and 11 days with a dose of CPT (5 mg/kg) each time. The tumor volumes and body weights of the mice were measured and recorded every two days. The tumor volumes were calculated with the formula Volume=LW2/2, where L and W are the long and short diameter of a tumor respectively. Animals were euthanized when the tumor size exceeded 2000 mm³, total body weight loss exceeded 20%, or when other signals of sickness, such as breathing problems, failure to eat and drink, lethargy or abnormal posture, were observed. One-way ANOVA analysis was performed to determine the statistical significance of treatment-related changes in tumour volume of animals and $p<0.05$ was considered to be significant.

Results

Figure 7A:
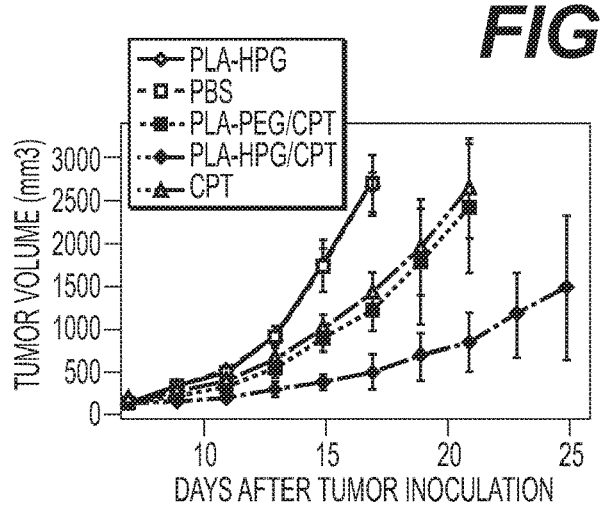
FIG. 7A is a graph showing tumor volume ($mm^3$) as a function of time after tumor inoculation (days) for PLA-HPG nanoparticles, PBS, PLA-PEG/CPT nanoparticles, PLA-HPG/CPT nanoparticles, and free CPT.
Figure 7B:
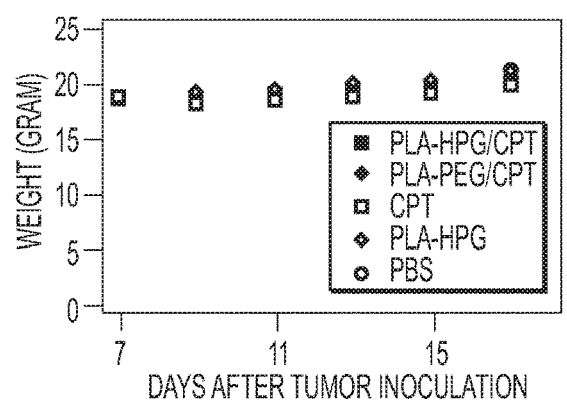
FIG. 7B is a graph showing the weight of mice (grams) as a function of time after tumor inoculation (days) for PLA-HPG nanoparticles, PBS, PLA-PEG/CPT nanoparticles, PLA-HPG/CPT nanoparticles, and free CPT.

To compare the therapeutic effect of PLA-HPG NPs with the optimized PLA-PEG NPs, CPT-loaded NPs intravenously were injected in mice bearing LLC subcutaneous tumors at a CPT dose of 5 mg/kg at 7 and 11 days after tumor inoculation (FIG. 7A). The growth rate of tumors treated with the blank PLA-HPG NPs was indistinguishable from that of tumors treated with PBS control; indicating that PLA-HPG alone has no effect on the tumor growth-. The tumor growth rate in mice given PLA-HPG/CPT NPs was significantly lower than that of the mice treated with PBS, free CPT, or PLA-PEG/CPT NPs. Interestingly, no significant in vivo toxicity was observed for all formulations (FIG. 7B)

Example 9. Synthesis of Functionalized HPG-coated Nanoparticles and Evaluation of Reversibility of Stealth Properties of Nanoparticles in Blood Circulation Materials and Methods Synthesis of Aldehyde-Functionalized Nanoparticles PLA-HPG NPs (0.1 mg/ml) in a 96-well plate (small vial) were incubated with 1 mM $NaIO_4$ and at each time point, the reactions were quenched with 2 mM $Na_2SO_3$. The NPs were washed two times with DI water in an ACROPREP® filter plate with 100 k cut-off (or AMICON® ultra filter 0.5 ml with 100 k cut-off) and then suspended in DI water.

The aldehydes on NPs were quantified with an aldehyde quantification assay kit (ABCAM®). The PLA-HPG NPs were used as a background subtraction control. The amount of aldehyde was calculated by comparing to a reference curve. The reference curve was made by using the aldehyde standard provided with the kit. The amount of aldehyde on each particle was calculated based on 100 nm hydrodynamic diameter of NPs and an assumed NP density of 1.0 g/cm³. For microarray printing, NPs load with DiD dye were suspended in PBS buffer containing 15% glycerol and 0.01% TRITON®-X100 at a concentration of 1 mg/ml in a 384-well plate. The NPs were arrayed on lysine coated slides using a SPOTBOT® microarrayer from ARRAYIT®. After 1 hour incubation in a humidity chamber, the printed slides were washed extensively with PBS 3 times, 5 min each. After a quick rinse with DI water, the slides were blow-dried with argon and subjected for imaging.

Ligand Attachment

For ligand or protein attachment, in a 96-well plate (or small vials), PLA-HPG$_{ALD}$ NPs were incubated with ligands or proteins ($NaCNBH_4$ should be added for proteins or ligands modified with amines or hydrazines) for 1 min-12 hours and the reaction was quenched with an excess amount of hydroxylamine (or ethanolamine for proteins or ligands modified with amines or hydrazines) solution in TRIS buffer (PH=7.4). The NPs were transferred to an ACROPREP® filter plate with 100 k cut-off (or AMICON® ultra filter 0.5 ml with 100 k cut-off or gel filtration for proteins and other large molecules) and washed two times with DI water or buffer.

To reduce the PLA-HPG$_{ALD}$ NPs back to PLA-HPG NPs (also referred to herein as non-bioadhesive nanoparticles, NNPs), PLA-HPG$_{ALD}$ NPs were incubated with $NaBH_4$ in $NaH_2PO_4$ (0.2M, PH=8.0) and the reaction was quenched with acetic acid and neutralized with PBS buffer. The NPs were washed with DI water twice. The blood circulation experiments were performed using the method in Example 6.

Polylysine coated glass slides were used as a tissue mimic to evaluate the bioadhesive property of PLA-HPG$_{ALD}$ NPs (BNPs). PLA-HPGA$_{ALD}$ NPs with different concentrations of aldehydes were prepared using a high-throughput procedure, where regular 96-well plates and 96-well filter plates were used to prepare the NPs and printed onto polylysine coated slides with a microarrayer.

For microarray printing, NPs load with DiD dye were suspended in PBS buffer containing 15% glycerol and 0.01% TRITON®-X100 at a concentration of 1 mg/ml in a 384-well plate. The NPs were arrayed on lysine coated slides using a SPOTBOT® microarrayer from ARRAYIT®. After 1 hour incubation in a humidity chamber, the printed slides were washed extensively with PBS 3 times, 5 min each. After a quick rinse with DI water, the slides were blow-dried with argon and subjected for imaging.

The bioadhesive property of PLA-HPG NPs on tissues was evaluated by applying suspended NPs ex vivo to the luminal surface of human umbilical vein. The umbilical cord was obtained from the Vascular Biology & Therapeutics Core Facility at Yale University and used within 12 hours.

The umbilical cord was cut into 10 cm length and washed with Ringer's buffer. The vein was perfused with 30 ml Ringer's buffer. PLA-HPG NPs and PLA-HPG$_{ALD}$ NPs (1 mg/ml) in Ringer's buffer were injected into vein and both ends of the vein were sealed. The sealed umbilical cords were immersed into Ringer's buffer and incubated at 37° C. for 2 h. After incubation, the vein in the cord was perfused with plenty of Ringer's buffer and frozen in OCT. The frozen cords were sectioned into 10-20 μm slices and mounted on glass slides. The slices were visualized with a fluorescence microscope. One-way analysis of variance (ANOVA) was performed to determine the statistical significance, $p<0.05$ was considered to be significant.

Results

Figure 8:
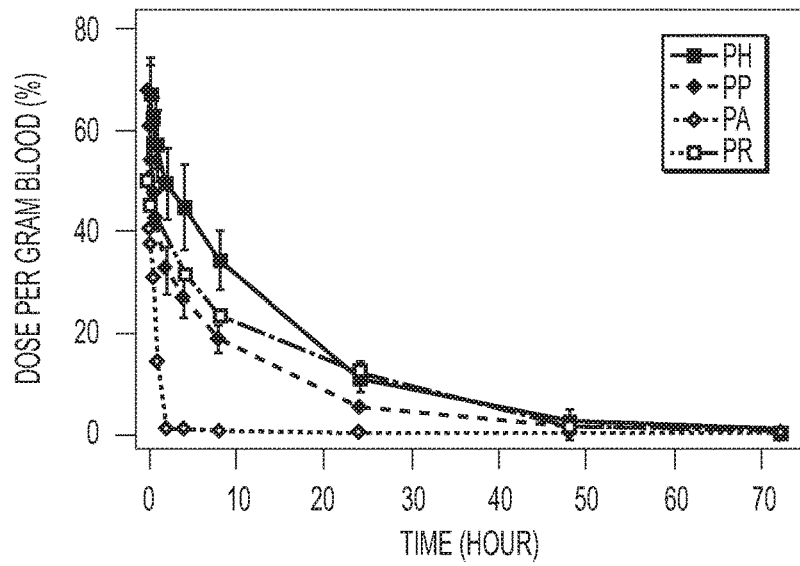
FIG. 8 is a graph showing percent dose in blood (%) as a function of time (hours) for PLA-HPG (PH), PLA-PEG (PP), PLA-HPG$_{ALD}$ (PA), and PLA-HPG$_{Reversed}$ (PLA-HPG NPs reversed from PLA-HPG$_{ALD}$ NPs) (PR) nanoparticles.

PLA-HPG$_{ALD}$ NPs (sticky, also referred to herein as bioadhesive nanoparticles, BNPs) could be reversed to PLA-HPG$_{Reversed}$ (stealth) NPs by $NaBH_4$ treatment, though one alcohol group is lost with the reduction-reversal cycle since each vicinal diol on HPG is oxidized by $NaIO_4$ to an aldehyde and each aldehyde is reduced to a single alcohol by $NaBH_4$. The results are shown in FIG. 8. The blood circulation confirmed that the PLA-HPG$_{ALD}$ NPs lost almost all their stickiness after treatment with $NaBH_4$. The back and forth tunability also demonstrated the robustness of the HPG coating on the nanoparticles.

The PLA-HPG NPs (NNPs) without $NaIO_4$ treatment did not adhere to glass slides and only background signal was detected. However, by transforming the surface property with $NaIO_4$, the amount of NPs immobilized on the glass slide increased as a function of duration of $NaIO_4$ treatment, indicating that the bioadhesive property of the PLA-HPG NPs can be tuned by control of $NaIO_4$ treatment.

Figure 9A:
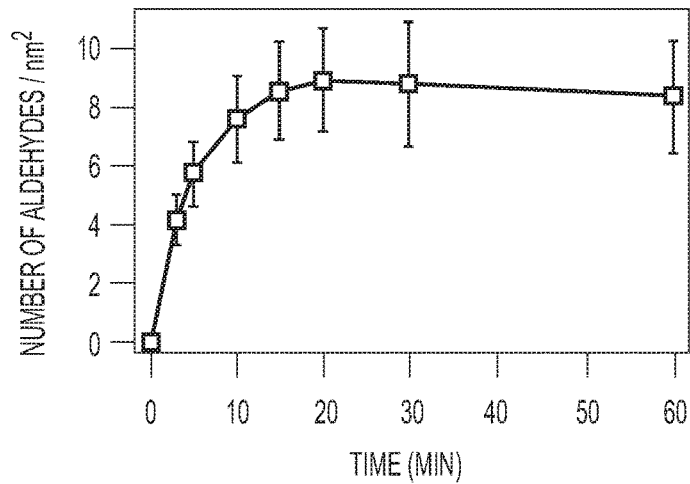
FIG. 9A is a graph showing the number of aldehyde groups/$nm^2$ on stealth NPs as a function of incubation time with $NaIO_4$. Data are shown as mean±SD (n=4).
Figure 9B:
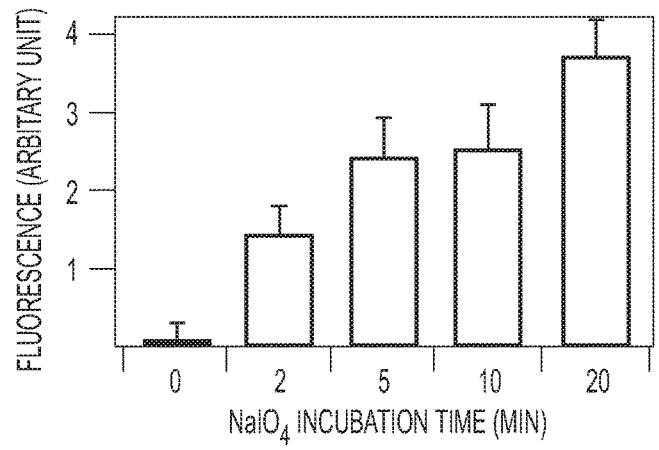
FIG. 9B is a graph showing surface immobilization of DiD loaded PLA-HPG NPs treated with $NaIO_4$ for different period of time on lysine coated slides. Data are shown as mean±SD (n=4).
Figure 9C:
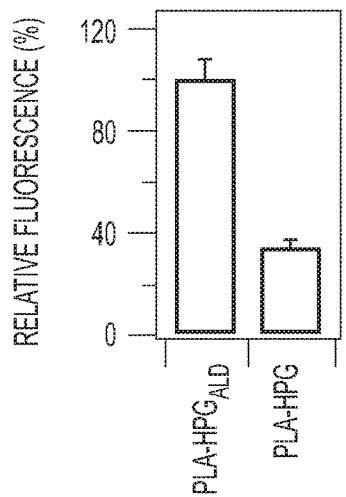
FIG. 9C is a graph showing relative fluorescence (%) obtained from sections of umbilical cord incubated with DiD-loaded PLA-HPG$_{ALD}$ and PLA-HPG NPs at 1 mg/ml on the lumen side of umbilical vein for 2 hours in Ringer's buffer at 37° C. The fluorescence was quantified and normalized to the average fluorescence of the PLA-HPG$_{ALD}$ on umbilical vein. Data are shown as mean±SD (n=6).

The results are shown in FIGS. 9A, 9B, and 9C. After incubation for 2 hours with both NPs and extensive washing, PLA-HPG$_{ALD}$ showed substantially higher retention on the luminal side of umbilical vein compared to that of PLA-HPG NPs ($P<0.05$). The fluorescence intensity was quantified from the fluorescence images.

The bioadhesive property of PLA-HPG NPs on tissues was evaluated by applying suspended NPs in vivo to the peritoneal cavity of nude mice. Six BALB/c nude mice were divided into 2 groups, 3 mice per group. IR-780 loaded PLA-HPGA$_{ALD}$ NPs (BNPs) and IR-780 loaded PLA-HPG NPs (NNPs) were administrated intraperitoneally into two groups of mice respectively. Each mouse received 100 μL NP suspensions. The fluorescence was monitored with live imaging (Xenogen Corp., Alameda, Calif.) over time. The quantification of fluorescence retained in intraperitoneal cavity over time was determined. After IP administration, the majority of PLA-HPG NPs disappeared from the IP cavity within first 24 hours. In contrast, PLA-HPG$_{ALD}$ NPs were retained in the intraperitoneal cavity for at least 5 days. Even at the end of the 10th day, PLA-HPG$_{ALD}$ NPs were still detectable at the intraperitoneal cavity. Free dye was also used as a control but it was all cleared in less than 4 hours.

This result indicates the application of PLA-HPG NPs for local delivery where an extended retention at delivery sites is needed. The density of the aldehydes on NPs can be controlled to modify the behavior of the PLA-HPGA$_{ALD}$ for local delivery.

These examples show that PLA-HPGA$_{ALD}$ NPs will interact with tissues since the bioadhesive property of PLA-HPGA$_{ALD}$ NPs is resulted from the Schiff-base bond between the aldehyde groups on PLA-HPG$_{ALD}$ NPs and the amine groups in tissue surface.

Example 10. In Vitro Cytotoxicity of Epothilone B-loaded Nanoparticles

Materials and Methods
Nanoparticle Characterization

The nanoparticles were characterized with TEM with the method described by Deng et al., *Biomaterials* 35:6595-6602 (2014). The hydrodynamic size of NPs was determined by dynamic laser scattering (DLS).

The amount of EB encapsulated in NPs was determined by HPLC with a C18 analytical column (PHENOMENEX®). Acetonitrile/water were used as mobile phase and the wavelength of the UV detector was set at 240 nm.

In Vitro Drug Release

EB loaded NPs suspension (10 mg) in a dialysis tube (10K cut-off) was dialyzed against 40 ml PBS. At each time point, PBS solution was removed and replaced with 40 ml fresh PBS. The EB released into PBS was extracted with ethylacetate (EA) twice, 5 ml each. The EA was evaporated to concentrate the extracts that were then lyophilized. The lyophilized extracts were dissolved in acetonitrile/water (50:50, volume) mixture for HPLC analysis.

In Vitro Cytotoxicity of Free EB and EB Loaded Nanoparticles.

UPSC cells (180 μL) were plated in each well of a 96 well plate at a density of 2,000/well and left in a 37° C. incubator overnight. 20 μl of free EB, EB/PLA-HPG NPs, or EB/PLA-HPG$_{ALD}$ NPs in the medium were added to each well. The cells were incubated for 72 h and cell viability was quantified with Cell Titer Blue.

Suppression of Cell Growth by EB/PLA-HPG$_{ALD}$ NPs Attached to Lysine Coated Slides.

Six lysine coated slides (25 mm×75 mm) were divided into two groups and each slide was divided to four quadrants with a pap pen (ABCAM®). For the first group, 100 μl EB/PLA-HPG$_{ALD}$ NPs (1 mg/ml), EB/PLA-HPG NPs (1 mg/ml), blank PLA-HPG$_{ALD}$ NPs (1 mg/ml) and PBS; and for the second group, PBS was applied to the quadrants of each slide. After 30 min incubation, each slide was washed extensively with plenty of PBS and placed to into a 10-cm dish filled with 20 ml medium with a density of UPSC cells at 2×10$^5$/ml. After incubation at 37° C. for 24 hours, the medium was aspirated and the slides were washed with 20 ml PBS for 4 times. The cells were stained with Hoechst (for nuclei, blue) and live/dead stain (green for live cells and red for dead cells) and then imaged under fluorescence microscope. The number of cells was counted by the number of nuclei with Image J—particles analysis.

Retention Profile of EB in Peritoneal Cavity

C57BL/6 mice (5-6 weeks old, Charles River Laboratories) were divided into three groups with 9 mice per group and one group with 3 mice. The group with 3 mice was used as a vehicle control. Either free EB (5 mg/mL stock solution in 30% PEG400/0.5% TWEEN® 80/5% propylene glycol/ 64.5% water, diluted to needed concentration with PBS before use), EB/NNPS, or EB/BNPS at an effective EB dose of 2.5 mg/kg were intraperitoneally injected into mice in each of 3 groups. At each time point (6 hr, 1 d and 3 d), 3 mice from each group and one mouse from the 3-animal vehicle control group were euthanized and the peritoneal cavities washed with 5 mL acetonitrile for 3 times. The acetonitrile samples were centrifuged and the supernatant was collected and processed for HPLC analysis. EB concentration was determined with HPLC with C18 column with methanol/water (7:3) with UV detector set at 240 nm absorbance.

Results

PLA-HPGA$_{ALD}$ NPs are useful for intraperitoneal delivery of chemotherapy drugs since the PLA-HPGA$_{ALD}$ NPs have significant extended retention in the intraperitoneal cavity (FIG. 10). Epothilone B (EB) was used as the model drug to demonstrate this use of PLA-HPG$_{ALD}$ NPs. EB was encapsulated into the PLA-HPG copolymer to make the EB/PLA-HPG NPs and then the EB/PLA-HPG NPs were oxidized by NaIO4 to EB/PLA-HPG$_{ALD}$ NPs. The encapsulation efficiency was about 50% and the loading of EB in EB/PLA-HPG NPs and EB/PLA-HPG$_{ALD}$ NPs were 2.5% and 1.2% respectively. There was no significant size or morphology difference between the EB/PLA-HPG NPs and EB/PLA-HPG$_{ALD}$ NPs from both DLS measurement (Table 2).

TABLE 2

Diameter and polydispersity index (PDI) of EB-containing nanoparticles.

| Nanoparticles | Diameter (nm) | PDI |
| --- | --- | --- |
| EB/PLA-HPG | 127 | 0.225 |
| EB/PLA-HPG$_{ALD}$ | 127 | 0.233 |

The controlled release curve was measured against PBS. The majority (about 80%) of the EB was released after eight hours and there is no significant difference between EB/PLA-HPG NPs and EB/PLA-HPG$_{ALD}$ NPs (FIG. 11A).

Figure 11B:
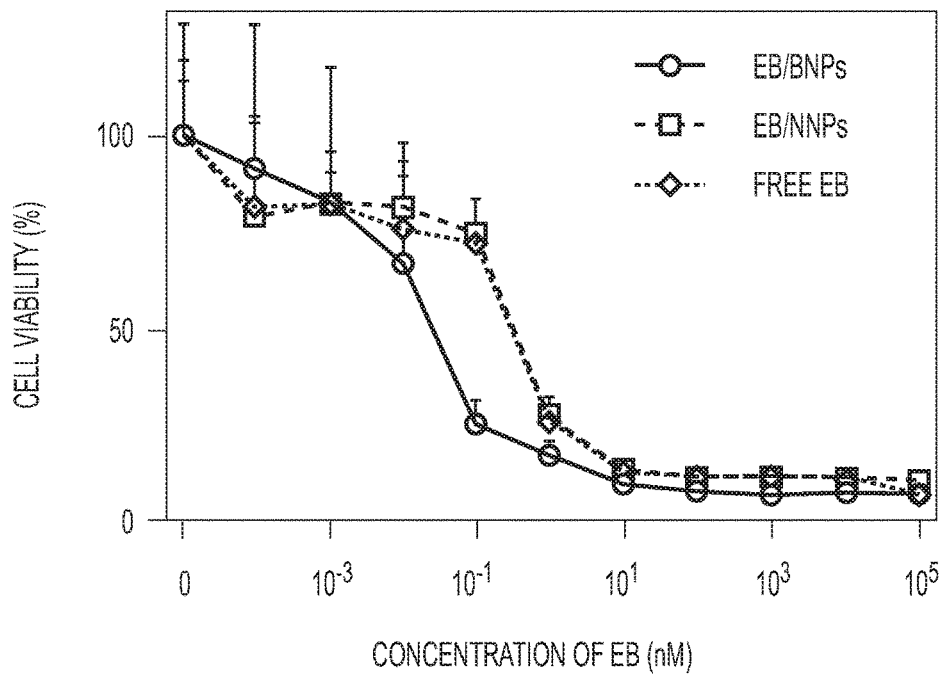
FIG. 11B is a graph of cell viability (%) of USPC cells after incubation with free EB, EB/PLA-HPG NPs (EB/NNPs) and EB/PLA-HPG$_{ALD}$ NPs (EB/BNPs) for 3 days. Data are shown as mean±SD (n=8).

The in vitro cytotoxicity of EB/PLA-HPG$_{ALD}$ NPs against uterine papillary serous carcinoma (UPSC) cells was also investigated, with EB/PLA-HPG NPs and free EB used as controls. The free EB showed the highest toxicity (FIG. 11B). The cytotoxicity of EB/PLA-HPG$_{ALD}$ NPs was comparable to that of EB/PLA-HPG NPs. The difference between the free EB and NP formulations of EB could be due to the retention of the EB in NPs, resulting in a low concentration of EB in the NP formulations compared to free EB. The enhanced toxicity of EB/PLA-HPG$_{ALD}$ NPs was due to the interaction between the PLA-HPG$_{ALD}$ NPs and the cells, resulting in much higher cell uptake of PLA-HPG$_{ALD}$ NPs compared to PLA-HPG NPs.

Figure 11C:
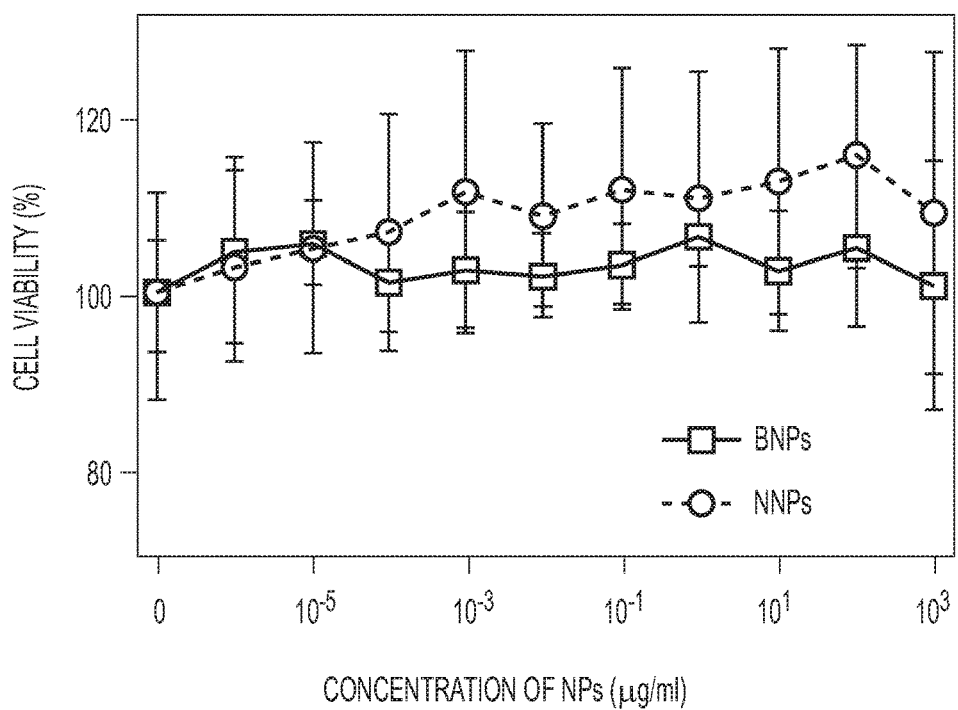
FIG. 11C is a graph of cell viability (%) of USPC cells after incubation with blank PLA-HPG$_{ALD}$ NPs (BNPs) and blank PLA-HPG NPs (NNPs) for 3 days. Data are shown as mean±SD (n=8).
Figure 11D:
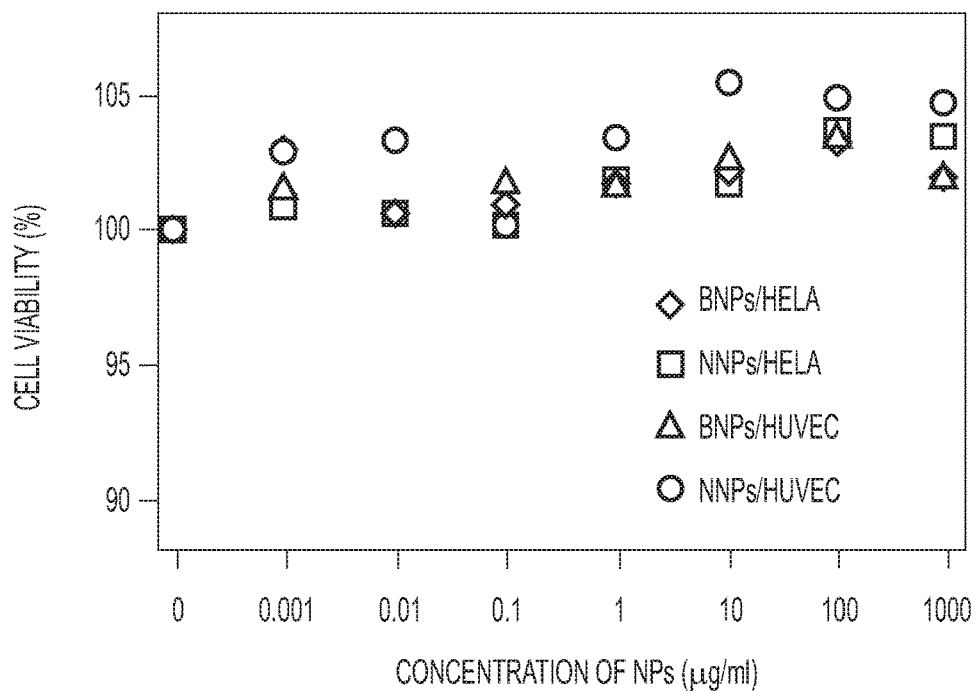
FIG. 11D is a graph of cell viability (%) of Hela and HUVEC cells after incubation with blank PLA-HPG$_{ALD}$ NPs (BNPs) and blank PLA-HPG NPs (NNPs) for 3 days. Data are shown as mean±SD (n=8).
Figure 11E:
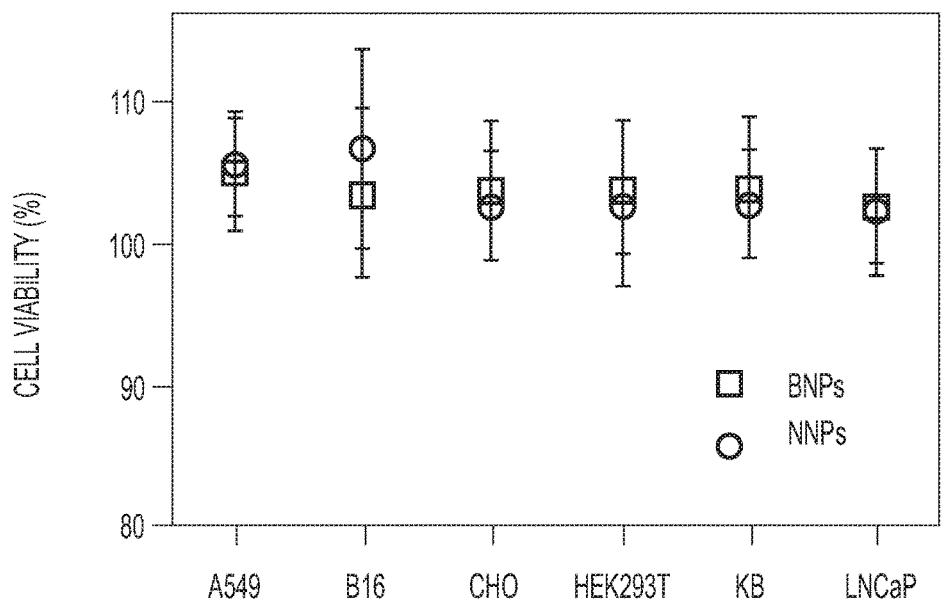
FIG. 11E is a graph of cell viability (%) of multiple cell lines after incubation with blank PLA-HPG$_{ALD}$ NPs (BNPs) and blank PLA-HPG NPs (NNPs) for 3 days. Data are shown as mean±SD (n=8).

To confirm that the cytotoxicity is due to the EB, and not the polymers, the effect of blank PLA-HPG$_{ALD}$ NPs and PLA-HPG NPs on UPSC cells was examined. Both blank NPs did not show any toxicity up to 1 mg/ml NPs, as shown in FIG. 11C (this concentration of blank NPs was much higher than the concentration of the EB loaded NPs used in above studies). To demonstrate the safety of the PLA-HPG$_{ALD}$ NPs, the cytotoxicity of blank PLA-HPG$_{ALD}$ NPs (PLA-HPG NPs was used as a control) on human umbilical vein endothelial cells (HUVEC) and Hela cells was examined. Both blank NPs did not show any toxicity (FIG. 11D). Further, the cytotoxicity of blank PLA-HPG$_{ALD}$ NPs at 1 mg/ml on variety of lab cell lines was tested and no cytotoxicity was observed on all these cell lines (FIG. 11E).

Figure 11F:
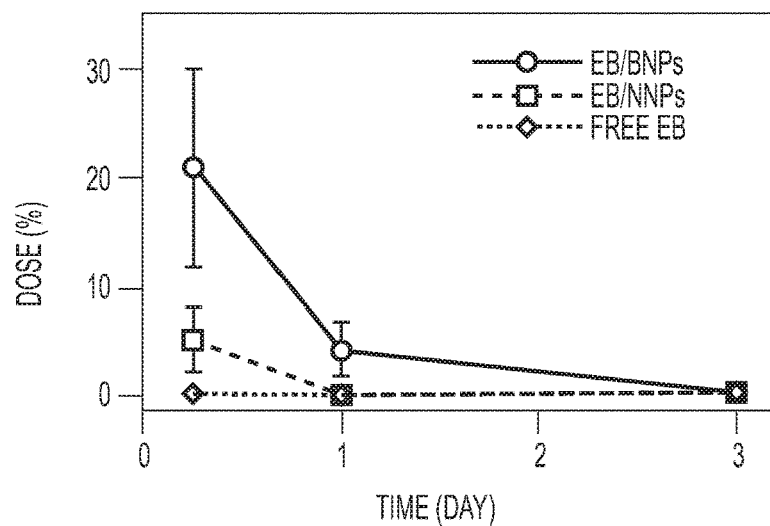
FIG. 11F is a line graph showing EB retention in the peritoneal cavity after i.p. administration of free EB, EB/NNPs, and EB/BNPs. Data are shown as means±SD (n=3).

To measure retention of EB within the peritoneal tissue, free EB, EB/BNPs, and EB/NNPs were administered intraperitoneally in nude mice. No EB was detected in mice receiving the free EB at six hours after a single dose (FIG. 11F). In contrast, detectable levels of EB were found at 6 hr with both EB/NNPs and EB/BNPs injections: the EB/BNPs treated mice had substantially higher concentrations of EB than the EB/NNPs treated mice (21% vs 5%, P<0.05, FIG. 11F). One day after IP administration, EB was still significantly higher after EB/BNPs injection when compared to EB/NNPS (P<0.05). No EB was detectable after 3 days for all formulations.

Figure 12:
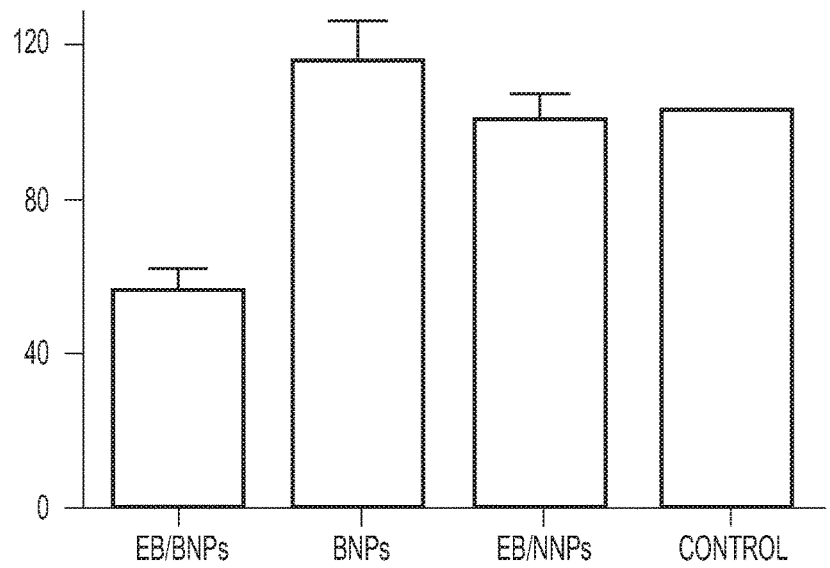
FIG. 12 is a graph of the percentage surface density (%) of USPC cells attached to slides coated with EB/PLA-HPG$_{ALD}$ NPs (EB/BNPs), PLA-HPG$_{ALD}$ NPs (BNPs), EB/PLA-HPG NPs (EB/NNPs), or PBS (Control). The surface density of cells was normalized to the PBS control. Data are shown as mean±SD (n=3).

The cytotoxic efficiency of EB/PLA-HPG$_{ALD}$ NPs was evaluated in vitro using lysine coated slides with surface-attached EB/PLA-HPG$_{ALD}$ NPs and UPSC cells. Each lysine coated slide was divided into four quadrants with a hydrophobic pen and EB/PLA-HPG$_{ALD}$ NPs, EB/PLA-HPG NPs, blank PLA-HPG$_{ALD}$ NPs and PBS were applied to each of quadrants. Control slide with PBS applied to all four quadrants were also prepared. After incubation and extensive washes, the slides were exposed to cell culture medium with UPSC. After 24 hours, the cells on each quadrant were imaged and quantified. There was no significant difference among EB/PLA-HPG NPs, blank PLA-HPG$_{ALD}$ NPs and PBS. However the cell attachment on EB/PLA-HPG$_{ALD}$ NPs coated area was significant suppressed (FIG. 12). The EB released from NPs had no effect to cells in the medium because the cell density of PBS control was similar to that of the PBS control on slides where all four quadrants were applied with PBS. This result could be due to the fact that the EB is slowly released from EB/PLA-HPG$_{ALD}$ NPs and forms a high local drug concentration around the cells closely interacted with EB/PLA-HPGA$_{ALD}$ NPs.

These studies confirmed that changing the surface property of NPs to bioadhesiveness could extend the retention of the intraperitoneally administered NPs. Further, the vehicles, the blank PLA-HPG$_{ALD}$ NPs, did not show any cytotoxicity on multiple cell lines for 3 days and up to 1 mg/ml of particles. Moreover, no weight loss or sickness was observed when the mice were injected with 5 mgs of blank PLA-HPG$_{ALD}$ NPs intraperitoneally, once a week for 3 weeks. It is believed the non-toxicity of PLA-HPG$_{ALD}$ NPs may be due to several factors: 1) aldehydes are widely present in foods, fragrances, and metabolites, so high tolerance of aldehydes is expected, which is further suggested by the wide existence of aldehyde dehydrogenase which can detoxify aldehydes efficiently (Vasiliou et al., *Chem Biol Interact* 202:2-10 (2013)); 2) aldehydes are covalently attached on nanoparticles, although the toxicity of low molecular weight free aldehydes is well known (O'Brien et al., *Crit. Rev. Toxicol.* 35:609-662 (2005)); and 3) the majority of the aldehyde interaction with proteins or other molecules is through reversible Schiff-base bonds so it cannot permanently modify or damage the biomolecules.

Both EB/PLA-HPG$_{ALD}$ NPs and EB/PLA-HPG NPs have similar size, morphology and controlled release profile. In the regular in vitro assay, both NPs show identical cytotoxicity profile. However, in the in vitro assay on lysine coated glass slides, the UPSC cell growth on EB/PLA-HPG$_{ALD}$ NPs coated lysine slides was significantly suppressed when compared to the slides treated with EB/PLA-HPG NPs, blank PLA-HPG$_{ALD}$ NPs and control lysine slides. The amount of EB/PLA-HPG$_{ALD}$ NPs attached on slides was very small and except the area containing the EB/PLA-HPGA$_{ALD}$ NPs, no other area had any effect on cell growth. Adhering to the peritoneum is a prerequisite for the disseminated cancer cells to establish peritoneal carcinomatosis ("PC") in the peritoneal cavity (Aoyagi et al., *World journal of gastroenterolog*: WJG 20:12493-12500 (2014)). In addition to slowly releasing drugs to the whole peritoneal cavity, EB/PLA-HPG$_{ALD}$ NPs could achieve a much higher local concentration of drugs on the surface of peritoneum, which could suppress the growth of the cancer cells adhered to peritoneum and thus eliminate the PC. Further, unlike microparticles, which tends to accumulate at lower abdomen, the small size of the PLA-HPGA$_{ALD}$ NPs allows the diffusion of the NPs to the whole intraperitoneal cavity.

It is important to emphasize that the unique stickiness of NPs disclosed herein to tissues or tissue mimics is the result of an interaction between the stickiness of the aldehyde group and the extremely high density of immobilized aldehydes on the NPs. The hyperbranched structure of HPG enables the ratio of aldehyde/PLA to reach 17.

Ex vivo studies confirmed the stickiness of NPs to diverse tissue surfaces, such as the luminal surface of umbilical vein. No deep penetration of NPs was observed in these settings, which suggests high localization of NPs after topical delivery. Injection of PLA-HPG$_{ALD}$ NPs into the intraperitoneal cavity or subcutaneous tissue resulted in much longer retention at these sites. IP administration of chemotherapeutic drugs such as paclitaxel has become a standard treatment for certain ovarian and colon cancers (Armstrong, et al., *ANZ J Surg*, 77:209-213 (2007); Gervais et al., *Journal of surgical oncology*, 108:438-443 (2013)). The standard IP procedure is accomplished through a surgically implanted catheter that allows passage of fluids containing dissolved or suspended chemotherapeutic drug into the abdomen of a patient. In this situation, the retention of the drug depends mainly on the duration of the infusion. PLA-HPGA$_{ALD}$ NPs encapsulated with drugs should have a great application in this area by significantly extending the retention of drugs at the administration site.

Example 11. In Vivo Cytotoxicity of Epothilone B-loaded Nanoparticles

Materials and Methods

Forty BALB/c Nude mice (5-6 weeks old, Charles River Laboratories) were intraperitoneally injected with 1×10$^6$ UPSC cells. After 1 week, drug treatments were started with PBS control, blank PLA-HPG$_{ALD}$ control and 3 EB formulations. The injected formulations were as follows: 1) PBS (PH=7.4); 2) blank PLA-HPG$_{ALD}$ in PBS; 3) free EB solution (5 mg/ml stock solution in 30% PEG400/0.5% TWEEN® 80/5% propylene glycol/64.5% water, diluted to needed concentration with PBS before use); 4) EB/PLA-HPG NPs in PBS; 5) EB/PLA-HPG$_{ALD}$ NPs in PBS. Treatments were administrated intraperitoneally with a dose of EB (0.5 mg/kg) every week for 5 weeks. The body weights of the mice were measured twice a week. Animals were euthanized when the body weight loss exceeded 20%, or when other signals of sickness, such as breathing problems, failure to eat and drink, lethargy or abnormal posture, were observed.

Results

Figure 13:
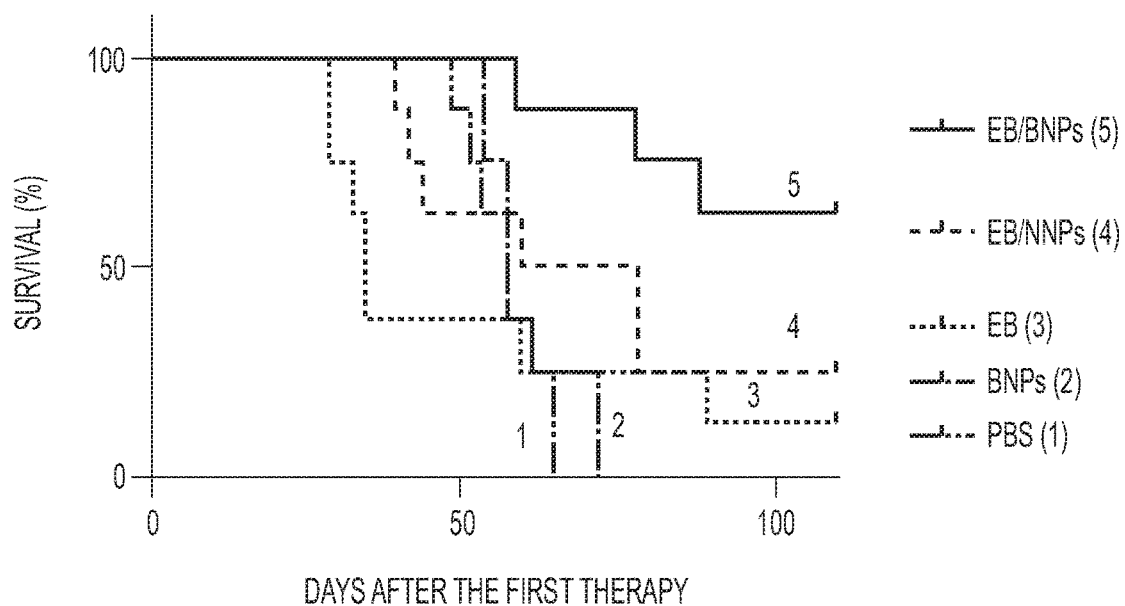
FIG. 13 is a Kaplan Meier survival curve of mice bearing intraperitoneal USPC tumors and treated with intraperitoneal injection of PBS (1), PLA-HPG$_{ALD}$ NPs in PBS (BNPs, (2)), free EB (3), EB/PLA-HPG NPs in PBS (EB/NNPs, (4)), and EB/PLA-HPG$_{ALD}$ NPs in PBS (EB/BNPs, (5)).

The Kaplan-Meier survival curve reelecting the efficacy of each of the treatment formulations is presented in FIG. 13.

In addition to the introduction of a new delivery vehicle, this study demonstrates that a new PC animal model could be established by IP inoculation of UPSC cells. The highly aggressive characteristics of UPSC include early peritoneal or lymphatic spread as well as inborn resistance to chemotherapy. The USPC cell line used in this study is a primary cell line from a patient. Due to the overexpression of β-tubulin III, this cell line is resistant to platinum/Taxane but not to EB (Rogue et al., Cancer, 119(14):2582-2592 (2013)). EB, a macrocyclic polyketide, has shown a significantly improved potency for killing UPSC when compared to paclitaxel. However, the effect of IP administration EB for treatment of PC is transient because it is a small molecule drug. Therefore, a vehicle with controlled release profile of EB is disclosed herein could achieve better bioavailability of EB for IP delivery.

Example 12. Flexibility, Retention, and Biodistribution Properties of NNPs and BNPs Materials and Methods IR-780 iodide, glycerol, $NaIO_4$, $Na_2SO_3$ and Bovine serum albumin (BSA) were obtained from Sigma-Aldrich. 1,1'-Dioctadecyl-3,3,3',3'-Tetramethylindodicarbocyanine,4 Chlorobenzenesulfonate Salt (DiD) was ordered from INVITROGEN®. The primary uterine serous carcinoma (USC) cell line (USC-Ark-2) used in this study was collected at the time of primary debulking surgery from a patient harboring stage IV USC and maintained in RPMI 1640 medium with 10% fetal bovine serum.

Nanoparticle Fabrication and Characterization

Nanoparticle fabrication and characterization was conducted as described in Example 9, and as detailed below.

For DiD/NNPs, IR-780/NNPs or EB/NNPs, PLA-HPG polymer and DiD, IR-780 or EB in certain ratio (total mass of 50-100 mg) were dissolved in a mixture of 2.4 mL ethyl acetate and 0.6 mL DMSO and subsequently added into 4 mL of DI water under vortexing. The resulting emulsion was further emulsified under probe sonication for three cycles at 10 sec each. The resulting fine emulsion was diluted in 20 ml DI water under stirring. The solution was connected to a rotavapor to evaporate the ethyl acetate and then applied to an AMICON® ultra centrifuge filtration unit (100 k cut-off). The nanoparticles were washed by filtration two times and then suspended in DI water. The nanoparticle suspension in water can be kept in frozen at −20° C. for a year. The dye or drug loaded BNPs were oxidized from NNPs loaded with dye or drug by $NaIO_4$ treatment with a method described described in Example 9.

To reduce the BNPs back to NNPs-R, BNPs were incubated with $NaBH_4$ in $NaH_2PO_4$ (0.2M, pH=8.0) and the reaction was quenched with acetic acid[44] and neutralized with PBS buffer. The NPs were washed with DI water twice.

The nanoparticles were characterized with TEM. The hydrodynamic size of nanoparticles was determined by dynamic light scattering (DLS). To determine the concentration of the IR-780 in NPs, 990 μL DMSO was added to 10 μL nanoparticles in aqueous solution. The concentration of the IR-780 dye was quantified with a plate reader by absorbance at 650 nm. EB loading in nanoparticles was determined by high-performance liquid chromatography (HPLC) with a C18 analytical column (PHENOMENEX®). The aldehydes on nanoparticles were quantified with an aldehyde quantification assay (ABCAM®) as described in Example 9.

The Retention of BNPs in Lysine Coated Well Plate or USC Cells

All DiD/BNPs, DiD/NNPs and DiD/NNPs-R were loaded with 0.2% DiD dye. Nanoparticles suspended in PBS (0.05 mg/ml) were incubated in lysine coated 96-well plate for 30 min. After incubation, the place was washed with PBS. After removing all the liquid, 100 μL DMSO was added. The plate was wrapped with aluminum foil and placed on an orbital shaker for 10 min and the fluorescence measured. For cell assay, USC cells were grown in 24 well plates to confluence and the cells were washed with cold PBS and then the plate was refilled with cold PBS suspended with nanoparticles at 0.05 mg/ml. After incubation in ice for 15 min, the cells were washed with cold PBS 4 times, 5 min each. After removing all the liquid, 300 μL DMSO was added, and the fluorescence measured.

Evaluation of in vitro drug release from the nanoparticles was conducted as described in Example 10.

Evaluation of in vitro cytotoxicity of the nanoparticles was conducted as described in Example 10.

Blood circulation of DiD-loaded nanoparticles was measured as described in Example 6.

Results

Figure 14A:
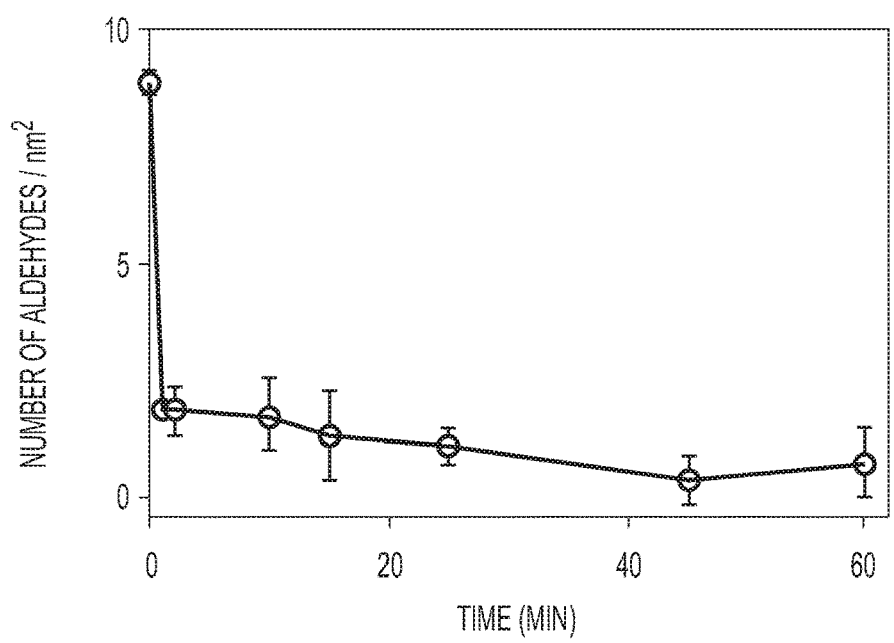
FIG. 14A is a line graph showing the surface density of aldehydes (Number of aldehydes/$nm^2$) on BNPs as a function of incubation time with $NaBH_4$.

It was determined that nanoparticles can be converted from a nonadhesive to a strongly bioadhesive state and back again by regulating the density of the aldehydes on the nanoparticle surface. To illustrate this flexibility, nanoparticles were converted by a cycle of oxidation and reduction, between the hydroxyl-rich NNP state, the aldehyde-rich BNP state, and a reduced NNP state (NNP-R). The aldehydes were reduced to alcohols by treatment with a common reducing agent (Hermanson G. T. *Bioconjugate techniques*, Edn. Third edition. (Elsevier/AP, London; Waltham, Mass.; (2013)), $NaBH_4$ (FIGS. 1A-1C). The concentration of aldehyde groups on BNPs was monitored as a function of duration of $NaBH_4$ treatment; most aldehyde groups were converted after 2 min of treatment (FIG. 14A). It is important to note that $NaBH_4$ treatment cannot reduce the aldehydes to the original vicinal diols, because one carbon is truncated by the initial conversion of vicinal diols to aldehydes (FIGS. 1A-1C).

Figure 14B:
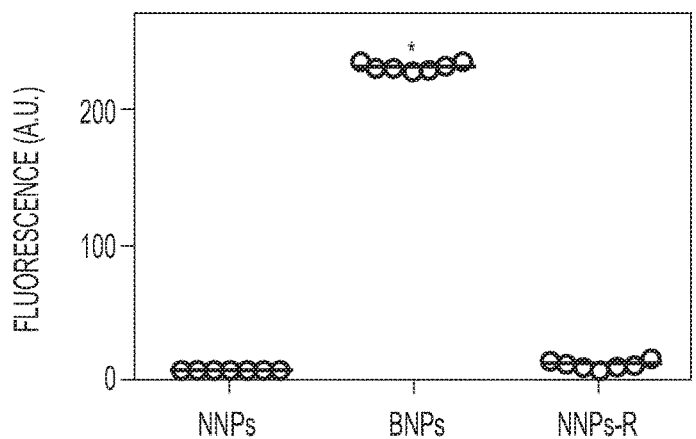
FIG. 14B is a graph showing retention (Fluorescence (A.U.)) of BNPs on (poly-L-lysine)-coated plates compared with NNPs and NNP-Rs.
Figure 14C:
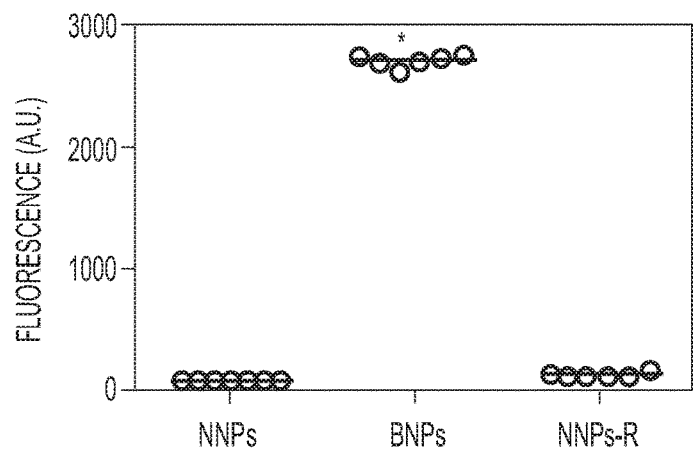
FIG. 14C is a graph showing retention (Fluorescence (A.U.)) of BNPs on USC cell monolayers compared with NNPs and NNP-Rs.
Figure 14D:
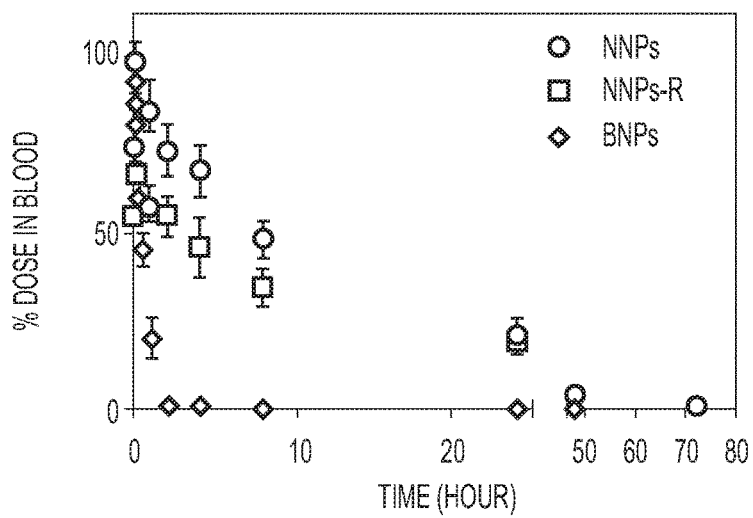
FIG. 14D is a graph showing the percentage dose in blood of DiD/NNPs, DiD/BNPs, and DiD/NNP-Rs as a function of time (hours) after i.v. injection in mice.

BNP, NNP, and NNP-R were identical in shape by transmission electron microscopy and hydrodynamic size measured by DLS (Table 3), suggesting oxidation and reduction cycles had no detrimental effect to the nanoparticles. To quantitate bioadhesion, nanoparticles at various states of aldehyde activation were tested by examining attachment to poly(L-lysine)-coated plates and USC cells (FIGS. 14B and 14C). To facilitate quantification of their bioadhesive properties, all nanoparticles were loaded with 0.2% DiD dye. First, the bioadhesive property of the three nanoparticles on poly(L-lysine) coated surfaces was evaluated. After incubation and extensive washing, the BNPs showed much higher retention on the poly(L-lysine) coated plates (FIG. 14B). The BNPs also showed much higher attachment to USC cells (FIG. 14C). The retention of NNPs or NNPs-R on both poly(L-lysine) surfaces or USC cell monolayers was negligible (FIGS. 14B and 14C). The nanoparticles for blood circulation times after intravenous injection in mice was also tested. The percent dose of BNPs dropped to 1.5% after 2 hours whereas significant numbers of NNPs (21.3%) were still circulating after 24 hours (FIG. 14D). NNP-Rs circulated with similar duration as the NNPs, reflecting the chemical similarity of their surfaces.

TABLE 3

Nanoparticle size measurements.

| Nanoparticles | Diameter (nm) | Polydispersity Index (PDI) |
|---|---|---|
| EB/NNPs | 127 | 0.225 |
| EB/BNPs | 127 | 0.233 |
| DiD/NNPs | 121 | 0.215 |
| DiD/BNPs | 117 | 0.232 |
| DiD/NNP-Rs | 97 | 0.213 |
| IR-780/NNPs | 131 | 0.331 |
| IR-780/BNPs | 128 | 0.297 |

Example 13. Intraperitoneal Retention of BNPs

Materials and Methods
In Vitro Dye Retention

One hundred (100) µl of NNPs loaded with IR-780 were suspended in PBS solution supplemented with BSA (10, 20, or 40 g/L), placed in microdialysis tubes (100 kDa cut-off), and floated in a large beaker containing 4 L of PBS solution supplemented with the same concentration of BSA (10, 20, or 40 g/L). At each time point, microdialysis tubes were removed in triplicate. The PBS solution supplemented with albumin was replaced with fresh buffer every 24 h. The dye left in each tube was quantified with a plate reader as described in Example 11.

Retention and Distribution of NPs after Intraperitoneal Administration

IR-780/BNPs and IR-780/NNPs were administrated intraperitoneally into two groups of mice respectively. Each mouse received 100 µL of the nanoparticle suspension at 10 mg/mL. The fluorescence was monitored with live imaging (Xenogen, Alameda, Calif.) over time. For the study of the distribution of the BNPs, 100 µL R-780/BNPs at 10 mg/mL was injected intraperitoneally to each mouse. After 18 hr, the fluorescence was visualized with live imaging and then the mice were euthanized. The peritoneal cavity of each mouse was imaged before and after all organs were removed.

Suppression of Cell Growth on EB/BNPs Attached Lysine Coated Slides.

Each PLL coated slide was divided into five blocks with a pap pen (ABCAM®). To each block was individually added 100 µL EB/BNPs (1 mg nanoparticles/mL and 0.025 mg EB/mL), EB/NNPs (1 mg NPs/mL and 0.025 mg EB/mL), EB (0.025 mg/mL), blank BNPs (1 mg/mL), and PBS. After 30 min incubation at room temperature, each slide was washed and placed into a 10-cm dish filled with 20 mL medium containing USC cells at a density of $2.0 \times 10^5$/mL. After incubation at 37° C. for 24 hr, the medium was aspirated and the slides were washed. The cells were stained with Hoechst (for nuclei, blue) and live/dead stain (green for live cells and red for dead cells, THERMO FISHER SCIENTIFIC®) and then imaged by fluorescence microscopy. The number of cells was counted by nuclei with Image J particle analysis. The viability was determined by normalizing the cell density to the control considered 100% viable.

Therapeutic Studies

BALB/c Nude mice (5-6 weeks old, Charles River Laboratories) were intraperitoneally injected with $1 \times 10^6$ USC cells. After 1 week, drug treatments were started with 8 animals in each group. In one experiment, three groups were compared: 1) PBS (400 µL); 2) free EB solution (5 mg/stock solution in 30% PEG400/0.5% TWEEN®80/5% propylene glycol/64.5% water, diluted to needed concentration with PBS before use, 400 µL); 3) EB/BNPs suspended in PBS (400 µL). In this experiment, treatments were administrated intraperitoneally with a 2.5 mg/kg dose of EB every week for 3 weeks. In another experiment, five groups were compared as described in Example 11.

The body weights of the mice were measured as described in Example 11.

Results

Studies were conducted to determine if BNPs interact and adhere strongly with mesothelial cells layering the abdominal cavity after IP delivery (FIG. 15), and whether this interaction of the BNPs with abdominal tissue will extend the retention of the BNPs after IP injection, therefore significantly improving the bioavailability of encapsulated drug and the efficacy of IP chemotherapy.

The effectiveness of this approach for IP delivery of patupilone (epothilone B, EB), a microtubule-stabilizing agent that targets class III Beta-tubulin, was tested. Importantly, EB has been shown to be 3 to 20 fold more effective than paclitaxel (PTX) in vitro against multiple PTX sensitive and resistant human tumor cell lines (Mozzetti et al., *Cancer Research*, 68, 10197-10204 (2008); Nobili et al., *Medicinal Research Reviews*, 32, 1220-1262 (2012); Paik et al., *Gynecologic Oncology*, 119, 140-145 (2010); and Roque et al., *Cancer*, 119, 2582-2592 (2013)). Unfortunately, the clinical use of EB in patients with recurrent disease is limited due to high toxicity, including severe diarrhea, vomiting, increased risk of bowel obstruction, and fatigue (Peereboom et al., *Neuro-oncology*, 16, 579-583 (2014); de Jonge et al., *Journal of Clinical Oncology: Official Journal of The American Society of Clinical Oncology* 23, 9048-9050 (2005)).

BNPs loaded with EB were used to test whether strongly adhesive nanoparticles will improve the efficacy of IP chemotherapy to PTX-resistant peritoneal metastasis. IP xenograft models derived from the primary USC cell line, USC-ARK-2, were developed. This cell line was selected because of its high expression of P-glycoprotein and tubulin-β-III, characteristics that have been recently shown by to confer PTX resistance while showing extreme sensitivity to EB Roque et al., *Cancer*, 119, 2582-2592 (2013), and because this cell line has been successfully used in prior work to generate consistent IP tumors in mice.

Figure 16:
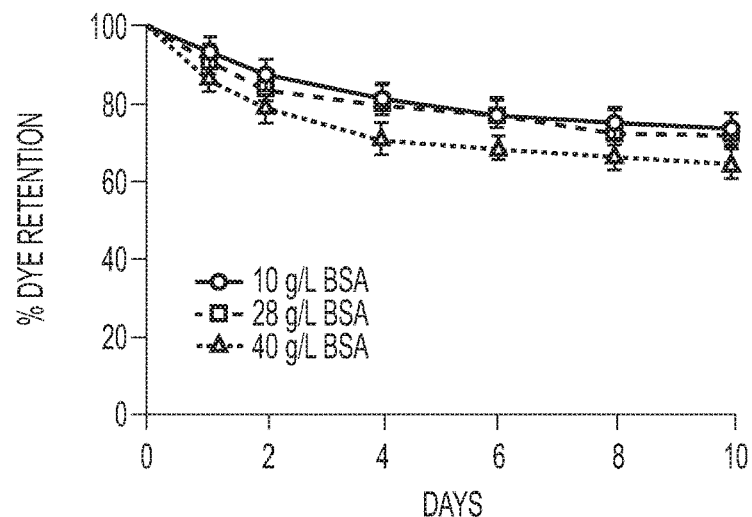
FIG. 16 is a line graph showing in vitro retention (% Dye Retention) of IR-780 dye in NNPs over time (days) in buffer simulating i.p. fluid. Data are shown as means±SD (n=3).

The retention of nanoparticles within the peritoneum after IP administration in mice was evaluated. BNPs and NNPs were loaded with 0.5% of IR-780 dye to facilitate imaging. At this loading, only a small fraction of the IR-780 dye is slowly released from the NPs over 10 days of incubation in buffered saline supplemented with physiological levels of protein (FIG. 16). Therefore, the dye molecule serves as a reliable marker for the presence of nanoparticles. As shown with other NNP/BNP combinations, the conversion of IR-780/NNPs to IR-780/BNPs by treatment with $NaIO_4$ had no apparent effect on nanoparticle size and morphology as observed by TEM nor hydrodynamic size as measured by DLS (Table 3). After IP injection of NNPs, most of the fluorescent signal, which was initially strong (5 min), was lost by the end of the first day. In contrast, after IP injection of BNPs, a strong fluorescent signal was observed to last up to 5 days. At the end of the 10th day, BNPs were still detectable in the area of the initial injection (FIG. 16). Remarkably, accumulation of BNPs in the lower abdomen, which is commonly seen after microparticle IP delivery (Steinbacher et al., *Small*, 6, 2678-2682 (2010)) was not observed with administration of BNPs; the majority of the BNPs adhered to the parietal peritoneum of the mice.

Example 10, and FIGS. 11A-11F, demonstrate the drug release from, and cell cytotoxicity and EB drug retention in peritoneal cavity of EB/BNPs and EB/NNPs.

Figure 15:
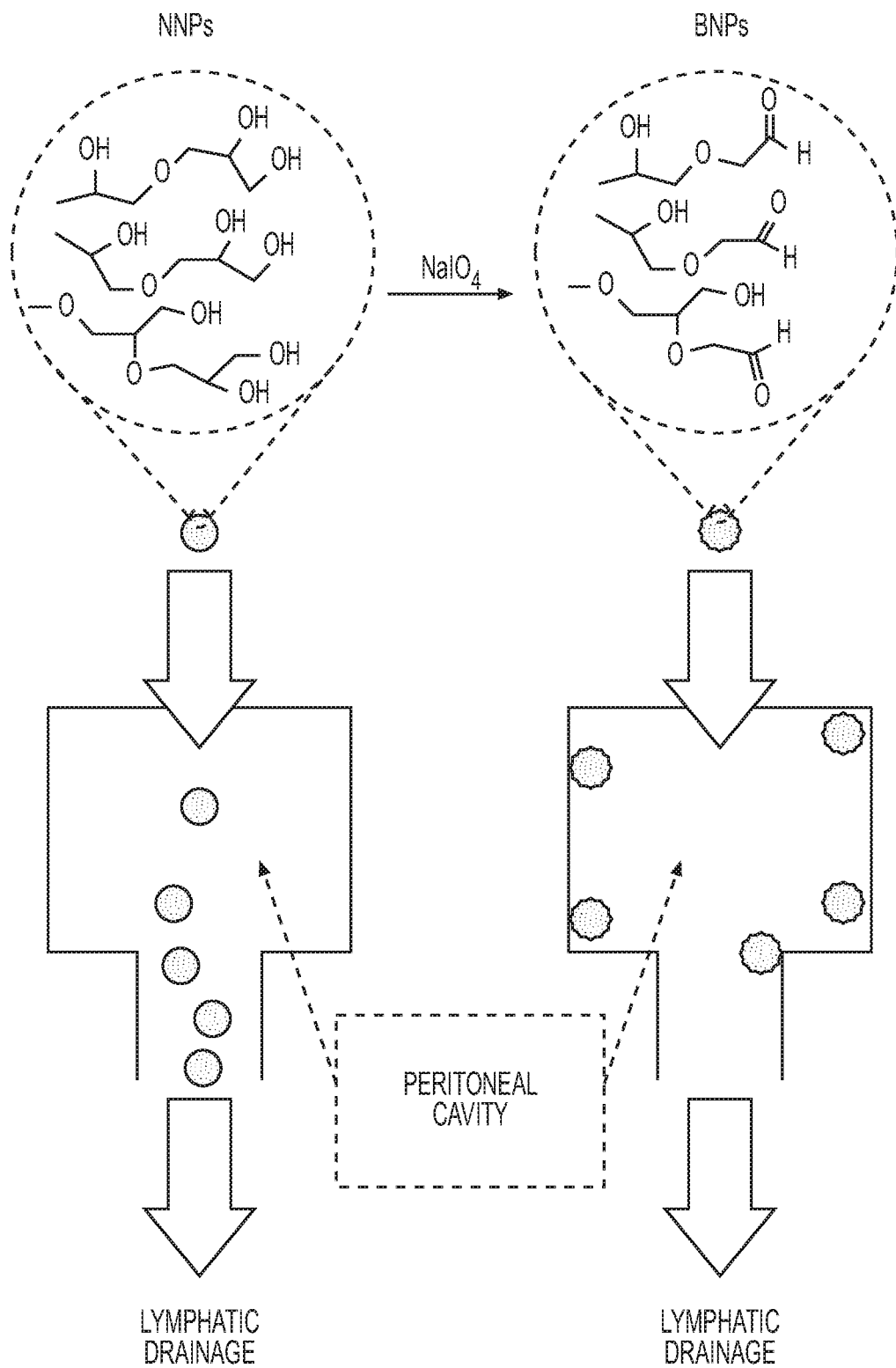
FIG. 15 is a diagram showing the conversion of BNPs to NNPs and the fate of NNPs and BNPs after i.p. administration. After i.p. administration, (Left) NNPs are cleared by lymphatic drainage, but (Right) BNPs are retained in the peritoneal cavity because of their bioadhesive property.
Figure 17:
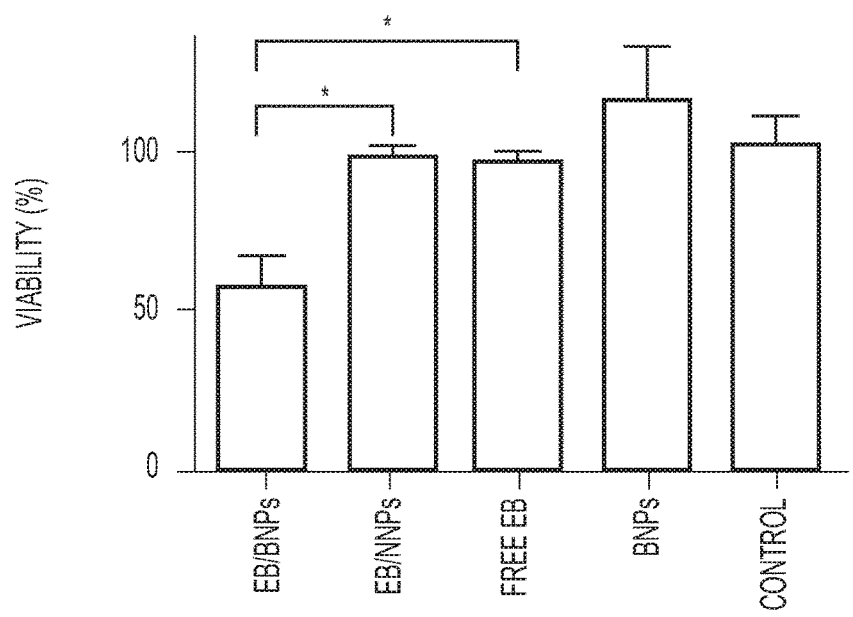
FIG. 17 is a bar graph showing viability (%) of USC cells grown on a glass slide divided into five blocks, each block incubated with EB/BNPs, EB/NNPs, free EB, BNPs, or PBS for 30 min, prior to washing and cell seeding. The surface density of the cells was quantified with ImageJ and normalized to the PBS control. Data are shown as means±SD (n=3). *$P<0.05$.

Therefore, EB/BNPs can protect the peritoneum against the attachment of floating cancer cells in the peritoneal fluid; this protection is provided by BNP retention on protein-rich peritoneal surfaces and their ability to deliver EB locally to treat adherent cells (FIG. 15). To simulate the microenvironment in which it is expected for the nanoparticles to reside after IP injection, the in vitro efficacy of surface immobilized EB/BNPs to suppress the growth of USC cells was evaluated. Microscope slides coated with poly(L-lysine) and incubated them with either free EB, unloaded nanoparticles, or EB-loaded nanoparticles were used. Significant suppression of tumor cell growth only in slide regions pretreated with EB/BNPs was observed (FIG. 17). No suppression of tumor growth was observed on surfaces treated with either blank BNPs or EB/NNPs. These results indicate that BNPs are retained on the lysine-coated surface of the slides due to their bioadhesive properties, and are able to deliver EB locally to adjacent cells, more effectively than any of the other nanoparticle preparations.

Figure 18A:
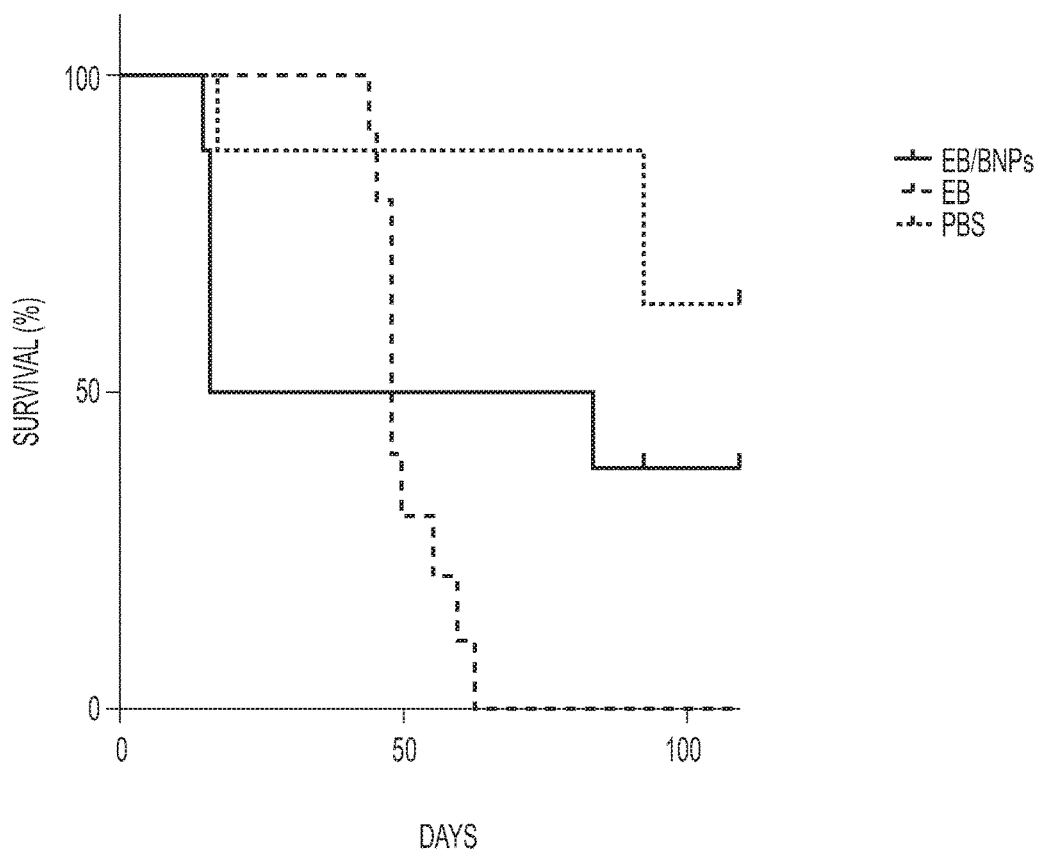
FIG. 18A is graph showing Kaplan-Meier survival curves of mice bearing i.p. USC tumors and treated with 2.5 mg/kg EB. Lower line shows survival of mice treated with PBS only, middle line shows survival of mice treated with EB only, and the upper line shows survival of mice treated with EB/BNPs.
Figure 18B:
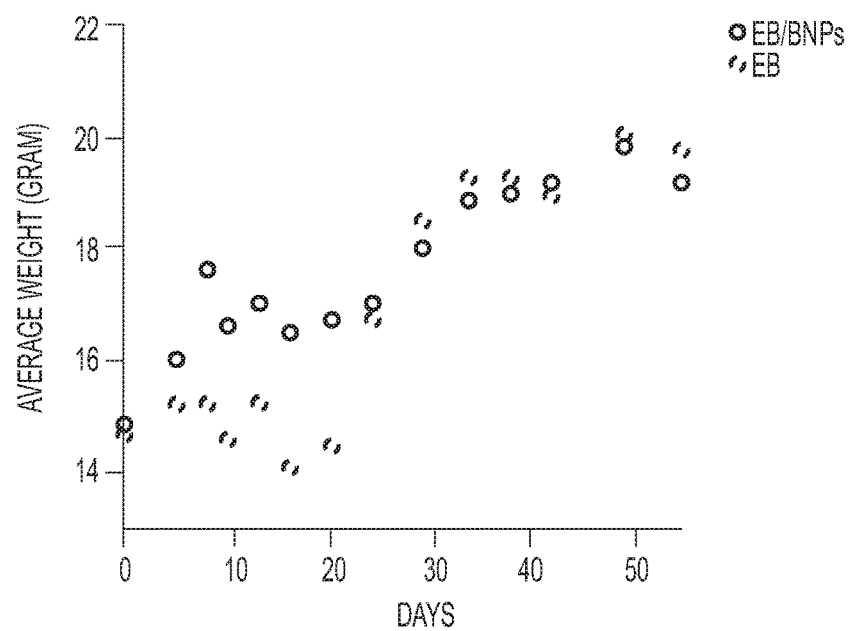
FIG. 18B is a dot plot of average weight (gram) of mice treated as in FIG. 18A.
Figure 18C:
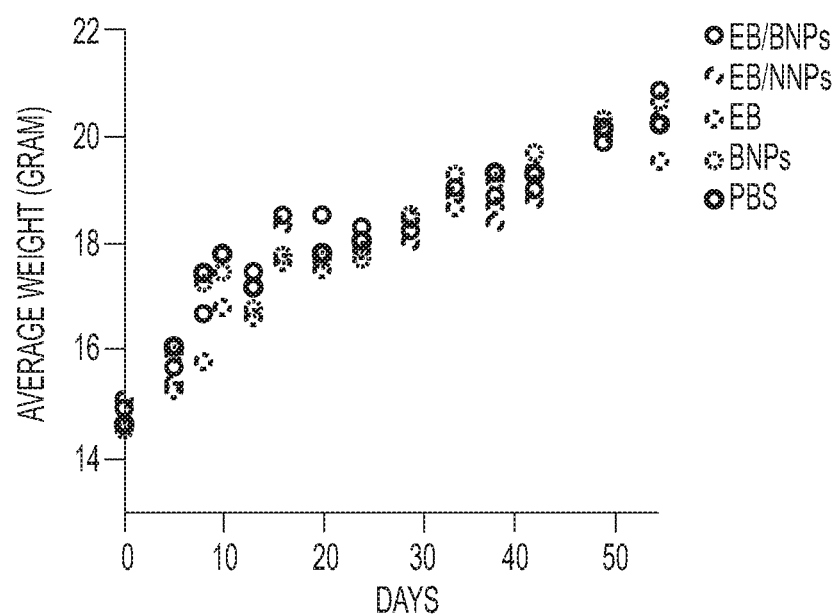
FIG. 18C is a dot plot of average weight (gram) of mice treated as in FIG. 13. Mice were weight twice a week.

The safety and efficacy of EB treatments in nude mice harboring class III Beta-tubulin overexpressing USC xenografts in the peritoneal cavity was tested. One week after tumor inoculation, EB/BNPS, EB/NNPS or free EB were administered weekly at an EB dose of 2.5 mg/kg (FIGS. 18A and 18B) or 0.5 mg/kg (FIGS. 13 and 18C). Animals receiving the higher dose of free EB (2.5 mg/kg) experienced weight loss (FIG. 18B) and early death due to EB toxicity (FIG. 18A), so all animals in the high dose (2.5 mg/kg) experiment were treated for only 3 weeks. At both doses, mice treated with EB/BNPs survived on average significantly longer than control animals treated with PBS (P=0.0006, 2.5 mg/kg; P=0.0005, 0.5 mg/kg), but in mice treated with free EB, only mice treated with the lower dosage showed significance (P=0.17, 2.5 mg/kg; P=0.01, 0.5 mg/kg) (FIGS. 18A and 13). Mice treated with EB/BNPs (0.5 mg/kg) survived on average significantly longer than mice treated with EB/NNPs (P=0.03) or EB, with 60% of the animals surviving longer than 110 days (FIG. 13). T the survival rate for mice treated with blank BNP was indistinguishable from mice treated with PBS (P=0.83) (FIG. 13). No significant difference was observed between mice treated with EB/NNPs and free EB (P=0.32), both with approximately 10% of the animals surviving to 110 days.

The diameter of the lymphatic ducts in the peritoneal cavity is about 1 μm. Microparticles, which typically have diameters larger than 4 μm, can escape the lymphatic drainage, resulting in long-lasting retention after IP administration (Tsai et al., *Pharmaceutical Research*, 24, 1691-1701 (2007); and Yang et al., *Drug Delivery and Translational Research* 4, 203-209 (2014)). However, microparticles tend to accumulate in the lower abdomen, due to gravitational forces Steinbacher et al., *Small*, 6, 2678-2682 (2010), likely leading to regions of high and low drug concentration. This heterogeneous distribution may also cause potential serious side effects including inflammation and peritoneal adhesion (Armstrong et al., *Gynecologic Oncology*, 103, 391-396 (2006); Kohane et al., *Journal of Biomedical Materials Research, Part A* 77, 351-361 (2006); and Lu et al., *The Journal of Pharmacology and Experimental Therapeutics*, 327, 673-682 (2008)), limiting their clinical application. Although multiple studies have demonstrated the advantages of nanoparticles in the delivery of drugs and biologic agents, the use of nanoparticles in the abdominal cavity is limited due to their rapid clearance due to their small size (approximately 100 nm) (Bajaj et al., *Pharmaceutical Research* 27, 735-738 (2010)). The Examples show that the addition of a dense coating of aldehyde groups on the particle surface confers bioadhesive properties to the nanoparticles (converting them into BNPs). This adhesive property promotes nanoparticle interaction with tissues, extending their retention in the abdomen following IP injection.

The results in an in vitro model show that the prolonged retention of BNPs led to improved treatment of disseminated tumors in the abdominal cavity. Consistent with this observation, free EB and EB/NNPs were rapidly cleared from the peritoneal cavity whereas EB was retained much longer when administered in EB/BNPs (FIG. 11F). The measurement of release from BNPs in vitro (~90% released in 24 hr, FIG. 11A) is consistent with the drug retention observed in vivo (~5% retained at 24 hr, FIG. 11F), despite the fact that the in vitro release was measured in an artificial system in which the nanoparticles were suspended in buffered saline, which is not identical to the conditions experienced by BNPs in the peritoneal space. The slow EB release over 24 hr leads to the reduced EB toxicity and enhanced EB effectiveness (FIGS. 18A and 13). The prolonged retention time for BNPs (some particles are retained for 5-10 d, FIG. 16) may be useful in other applications: for example, for BNPs loaded with other drugs that are released over longer periods.

When not loaded with drug agents, the BNPs are not toxic. In cell cultures, BNPs did not show any cytotoxicity even at high concentration (i.e., up to 1 mg/ml) and mice treated with BNPs (IP injection of 5 mg BNPs, once a week for 5 weeks) had no evidence of weight loss or behavioral changes. In addition, the repeated IP injection of BNPs did not appear to lead to any non-specific responses that affected tumor growth or animal health. This was attributable to the low toxicity of BNPs due to several factors: 1) although free low molecular weight aldehydes can be toxic (O'Brien et al., *Critical Reviews In Toxicology*, 35, 609-662 (2005)), the surface aldehyde groups are covalently attached to BNPs, limiting their dispersion; 2) high tolerance to aldehydes is expected since they are widely present in foods, fragrances, and metabolites, and can be efficiently detoxified by the enzyme aldehyde dehydrogenase (Vasiliou et al., *Chemico-Biological Interactions* 202, 2-10 (2013)).

In summary, the results demonstrate the effectiveness of these EB formulations by measuring the survival of mice with PTX-resistant USC xenografts. To further limit EB toxicity in animals, a 5-fold lower dose of EB compared to previous studies in nude mice with human multiple myeloma xenografts (Lin et al., *Blood*, 105, 350-357 (2005)) was used. Even at this lower dose of EB, however, significant toxicity (i.e., weight loss, diarrhea, bowel dilation) was observed in mice treated with free EB. Remarkably, very little toxicity was observed in the mice treated with EB/BNPs (FIG. 18B). This difference in toxicity is attributable to two factors associated with EB/BNPs: the gradual release of EB from the BNPs (FIG. 11A), which likely reduces peak drug levels, and the strong adhesion of BNPs to the peritoneal tissue, which were detectable even after 5 days of administration. This reduces EB doses to non-target tissues and vital organs by fast lymphatic drainage. EB was quickly cleared from the abdominal cavity, likely by diffusion through the peritoneal membrane into capillaries and transport through the hepatic portal system (De Bree et al., *Annals of Gastroenterology*, 16, 20-33 (2003)), which would be expected to lead to side effects and significantly lower bioavailability (Goodin et al., *Journal of Clinical Oncology: Official Journal of The American Society of Clinical Oncol-* ogy, 22, 2015-2025 (2004)). The main side effect caused by EB in the study was gastrointestinal toxicity, which is in agreement with the known toxicity profile of EB (Peereboom et al., *Neuro-Oncology*, 16, 579-583 (2014); Colombo et al., *Journal of Clinical Oncology: Official Journal of The American Society of Clinical Oncology*, 30, 3841-3847 (2012); and Forster et al., *Clinical Cancer Research: An Official Journal of The American Association For Cancer Research*, 13, 4178-4184 (2007)).

The EB/BNPS treated mice demonstrated significantly improved survival when compared to the controls (P<0.05), with 60% of the animals alive at the end of the experiment (110 days). This is attributable to the enhanced effectiveness of the EB/BNPs due to their bioadhesion and slow release. As evidence for the importance of bioadhesion, EB in non-adhesive particles (EB/NNPs) were not as effective as EB/BNPs.

Studies have shown strong activity of small molecules that selectively target the Her2/PI3K/Akt/mTor pathway against USCs. However, treatments with a single agent were only transiently effective and tumors rapidly acquired resistance in vivo. Preclinical data suggest that dual-targeting of HER2/PIK3CA with a Pan-HER inhibitor (Neratinib) and a PIK3CA inhibitor (Taselisib) may be synergistic and able to achieve durable regression of USC xenografts in mice. However this strategy is only applicable for the treatment of patients whose USC tumors harbor the amplification of the c-erbB2 gene and the concomitant amplification or oncogenic mutations in the PI3KCA gene. Therefore, alternate strategies are likely needed. It is shown here that nanoparticles loaded with EB treated USC tumors following local/regional (IP) administration. This strategy takes advantage of the chemical properties of the nanoparticles and of the extreme sensitivity of USCs to the EB and may therefore be used for the treatment of the vast majority of USC patients, regardless the genetic landscape of their tumors (Cross et al., *American Journal of Obstetrics and Gynecology*, 203, 162 e161-168 (2010)).

The Examples represent the first demonstration that IP administration of bioadhesive nanoparticles encapsulating EB can enhance survival of mice with intraperitoneal tumors formed from USC xenografts. The EB/BNPs exhibits higher therapeutic efficacy and lower toxicity than free EB and EB/NNPS. Since the bioadhesive property of BNPs is based on the general interaction between aldehydes on NPs and proteins on tissue, this approach is applicable to other strategies for local delivery of active agents.

We claim:

1. Particles comprising
   (a) a core comprising one or more hydrophobic polymers; and
   (b) a shell comprising hyperbranched polyglycerol comprising a plurality of surface hydroxyl groups,
   wherein the hyperbranched polyglycerol is covalently bound to the hydrophobic polymers of the core,
   wherein a plurality of the surface hydroxyl groups are functionalized with one or more surface reactive functional groups selected from the group consisting of aldehydes, amines, O-substituted oximes, and combinations thereof; and/or targeting moieties are bound to the surface reactive functional groups,
   wherein the surface reactive functional groups and the targeting moieties render the shell of the particles bioadhesive, and
   one or more agents selected from the group consisting of therapeutic agents, diagnostic agents, prophylactic agents, nutraceutical agents, and combinations thereof are encapsulated within the particle, associated with the surface of the particle, or a combination thereof.

2. The particles of claim 1, wherein the hydrophobic polymer is biodegradable.

3. The particles of claim 2, wherein the biodegradable polymer is an aliphatic polyester.

4. The particles of claim 3, wherein the aliphatic polyester is selected from the group consisting of poly(lactic acid), poly(glycolic acid), and copolymers thereof.

5. The particles of claim 4, wherein the aliphatic polyester is polylactic acid.

6. The particles of claim 1, wherein the one or more surface reactive functional groups adhere to tissue, cells, proteins, or combinations thereof.

7. The particles of claim 1, comprising therapeutic agents.

8. The particles of claim 1, wherein the one or more agents are associated with the surface of the particle.

9. The particles of claim 1, wherein the one or more agents are encapsulated within the particle.

10. The particles of claim 1, wherein the targeting moieties are covalently bound to the surface reactive functional groups.

11. The particles of claim 1, wherein the particles are nanoparticles.

12. A pharmaceutical composition comprising the particles of claim 1 and one or more pharmaceutically acceptable carriers.

13. The composition of claim 12, wherein the one or more carriers are suitable for parenteral administration.

14. The composition of claim 12, wherein the one or more carriers are suitable for enteral administration.

15. A method of delivering one or more agents selected from the group consisting of therapeutic agents, diagnostic agents, prophylactic agents, or nutraceutical agents comprising administering the particles of claim 1 to an individual in need thereof.

16. The method of claim 15, wherein the particles are administered by injection, locally or regionally.

17. The method of claim 15, wherein the particles are administered orally.

18. The method of claim 15, comprising administering the particles comprising the therapeutic or prophylactic agents to an individual with cancer.

19. The method of claim 18, wherein cancer is selected from the group consisting of peritoneal cancer, uterine cancer, endometrial cancer, ovarian cancer, bladder cancer, colorectal cancer, prostate cancer, and testicular cancer.

20. The particles of claim 1, wherein the surface hydroxyl groups are comprised of vicinal diol groups.

21. The particles of claim 1, wherein the surface hydroxyl group density is at least about 1, 2, 3, 4, 5, 6, 7, or 8 hydroxyl groups/nm$^2$.

22. The particles of claim 1, wherein the surface reactive functional group density is at least about 1, 2, 3, 4, 5, 6, 7, or 8 surface reactive functional groups/nm$^2$.

23. The particles of claim 10, wherein the targeting moieties are present at a density on the shell of at least about 1, 2, 3, 4, 5, 6, 7, or 8 targeting moieties/nm$^2$.

24. The particles of claim 1, wherein the targeting moieties bind to one or more targets associated with an organ, tissue, cell, or extracellular matrix.

* * * * *